US008551937B2

(12) United States Patent
Wakabayashi et al.

(10) Patent No.: US 8,551,937 B2
(45) Date of Patent: Oct. 8, 2013

(54) PEPTIDE HAVING AN EXTENDING ACTION FOR HALF-LIFE OF OBJECT PEPTIDE IN PLASMA

(75) Inventors: Naomi Wakabayashi, Gunma (JP); Seiji Sato, Gunma (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 238 days.

(21) Appl. No.: 12/675,961

(22) PCT Filed: May 22, 2009

(86) PCT No.: PCT/JP2009/059464
§ 371 (c)(1),
(2), (4) Date: Mar. 16, 2010

(87) PCT Pub. No.: WO2009/142307
PCT Pub. Date: Nov. 26, 2009

(65) Prior Publication Data
US 2010/0305031 A1    Dec. 2, 2010

(30) Foreign Application Priority Data

May 23, 2008    (JP) ................................. 2008-136106

(51) Int. Cl.
*A61K 38/02*    (2006.01)

(52) U.S. Cl.
USPC .............................. 514/1.1; 530/300; 530/324

(58) Field of Classification Search
None
See application file for complete search history.

(56) References Cited

U.S. PATENT DOCUMENTS

| 6,034,231 | A | * | 3/2000 | Tanaka et al. | ............... | 536/23.51 |
| 7,385,026 | B1 | | 6/2008 | Kangawa et al. | | |
| 2009/0181888 | A1 | | 7/2009 | Murakami et al. | | |
| 2009/0305969 | A1 | | 12/2009 | Murakami et al. | | |

FOREIGN PATENT DOCUMENTS

| EP | 2 052 738 | 4/2009 |
| EP | 2 070 549 | 6/2009 |
| WO | WO 01/07475 | 2/2001 |
| WO | WO-03/020746 A1 | 3/2003 |
| WO | WO-2008/043822 A2 | 4/2008 |

OTHER PUBLICATIONS

Callebaut, C et al, Virology 1996 vol. 218 p. 181-192.*
Protamine Sulfate, package insert. Produced by PPC (Pharmaceutical Partners of Canada), Apr. 2009.*
Kurukulasuriya, Ravi et al; "Xanthine mimetics as potent dipeptidyl peptidase IV inhibitors." Bioorg. and Med. Chem. Lett. (2006) 16 p. 6226-6230.*
Mojsov, Svetlana et al., "Insulinotropin: Glucagon-like Peptide I (7-37) Co-encoded in the Glucagon Gene is a Potent Stimulator of Insulin Release in the Perfused Rat Pancreas," J. Clinical Investigation, vol. 79, Feb. 1987, pp. 616-619.
Nauck, Michael A. et al., "Preserved Incretin Activity of Glucagon-like Peptide 1 [7-36 Amide] but Not of Synthetic Human Gastric Inhibitory Polypeptide in Patients with Type-2 Diabetes Mellitus," J. Clinical Investigation, vol. 91, Jan. 1993, pp. 301-307.
O'Harte, Finbarr P.M. et al., "N-terminally modified glucagon-like peptide-1(7-36) amide exhibits resistance to enzymatic degradation while maintaining its antihyperglycaemic activity in vivo," Biochimica et Biophysica Acta 1474 (2000), pp. 13-22.
Madsbad, Sten et al., "Improved Glycemic Control With No Weight Increase in Patients With Type 2 Diabetes After Once-Daily Treatment With the Long-Acting Glucagon-Like Peptide 1 Analog Liraglutide (NN2211)," Diabetes Care, vol. 27, No. 6, Jun. 2004, pp. 1335-1342.
Defronzo, Ralph A., "Effects of Exenatide (Exendin-4) on Glycemic Control and Weight Over 30 Weeks in Metformin-Treated Patients With Type 2 Diabetes," Diabetes Care, vol. 28, No. 5, May 2005, pp. 1092-1100.
Kim, Jung-Guk, "Development and Characterization of a Glucagon-Like Peptide 1-Albumin Conjugate—The Ability to Activate the Glucagon-Like Peptide 1 Receptor In Vivo," Diabetes, vol. 52, Mar. 2003, pp. 751-759.
Kojima, Masayasu et al., "Ghrelin is a growth-hormone-releasing acylated peptide from stomach," Nature, vol. 402, Dec. 9, 1999, pp. 656-660.
Neary, M. Nicola et al., "Ghrelin Increases Energy Intake in Cancer Patients with Impaired Appetite: Acute, Randomized, Placebo-Controlled Trial," The Journal of Clinical Endocrinology & Metabolism 89(6), 2004, pp. 2832-2836.
Akamizu, Takashi et al., "Repeated administration of ghrelin to patients with functional dyspepsia: its effects on food intake and appetite," European Journal of Endocrinology (2008), vol. 158, pp. 491-498.
Nagaya, Noritoshi et al., "Hemodynamic and hormonal effects of human ghrelin in healthy volunteers," Am J Physiol Regulatory Integrative Comp Physiol 280, pp. R1483-R1487, 2001.
Nagaya, Noritoshi et al., "Hemodynamic, Renal, and Hormonal Effects of Ghrelin Infusion in Patients with Chronic Heart Failure," The Journal of Clinical Endocrinology & Metabolism 86(12), pp. 5854-5859; 2001.

(Continued)

*Primary Examiner* — Cecilia J Tsang
*Assistant Examiner* — Fred Reynolds
(74) *Attorney, Agent, or Firm* — Drinker Biddle & Reath LLP

(57) ABSTRACT

An isolated chimeric peptide consisting of one or two added peptides and an object peptide wherein the added peptide is bonded to the N-terminus, the C-terminus or both of the object peptide, wherein if the added peptides are bound to both terminals, the two added peptides may be the same or different; and physiological activity of the object peptide is still retained, wherein the object peptide is a natural physiologically active peptide selected from the group consisting of an atrial natriuretic peptide, a brain natriuretic peptide, a C-type natriuretic peptide, motilin, a glucagon-like peptide 1, parathyroid hormone, and calcitonin, or a derivative of any thereof, wherein the derivative has one or more amino acid(s) deleted from the amino acid sequence of a natural physiologically active peptide and has the desired physiological activity.

33 Claims, 13 Drawing Sheets

(56) References Cited

OTHER PUBLICATIONS

Nagaya, Noritoshi et al., "Chronic Administration of Ghrelin Improves Left Ventricular Dysfunction and Attenuates Development of Cardiac Cachexia in Rats With Heart Failure," Circulation 2001; vol. 104; pp. 1430-1435.

Korbonits, Márta et al., "Ghrelin—a hormone with multiple functions," Frontiers in Neuroendocrinology, vol. 25, 2004, pp. 27-68.

Choi, Kichoon et al., "The Role of Ghrelin and Growth Hormone Secretagogues Receptor on Rat Adipogenesis," Endocrinology 144(3), pp. 754-759, 2003.

Kojima, Masayasu et al., "Structure and Function of Ghrelin," Seikagaku (2007), vol. 79, No. 9, pp. 853-867 (English Abstract).

International Preliminary Report on Patentability issued Jan. 11, 2011 in Application No. PCT/JP2009/059464, filed May 22, 2009.

Dong, Jesse. Z. et al., "GHS-1A Receptor Agonists that are Highly Effective in Stimulating Body Weight Gain and Food Intake," *Biopolymers*, 2005, vol. 80, No. 4, pp. 578-579.

Pemberton, Chris J. et al., "Biochemistry of Ghrelin Precursor Peptides," In Vitamins and Hormones, 2007. 12, vol. 77, pp. 13-30 (Elsevier Inc.).

Magota Koji, Gene & Medicine Mook, "Synthesis of Post-translationally Modified Peptide—Preparation of Ghrelin by Semisynthesis" 2007. 07, No. 8, pp. 232-238 (along with partial English translation).

International Search Report dated Jul. 7, 2009 for International PCT Application No. PCT/JP2009/059464 filed May 22, 2009.

Supplementary European Search Report mailed Jul. 22, 2011 issued in EP Application No. 09750669.5.

Dennis et al., "Albumin Binding as a General Strategy for Improving the Pharmacokenetics of Proteins", *The Journal of Biochemical Chemistry*, vol. 277, No. 38, Sep. 20, 2002, pp. 35035-35043.

Nguyen et al., "The pharmacokenetics of an albumin-binding FAB (AB.Fab) can be modulated as a function of affinity for albumin", *Protein Engineering, Design & Selection*, vol. 19, No. 7, Apr. 18, 2006, pp. 291-297.

\* cited by examiner (Mean Value/Standard Deviation, N=3)

(Mean Value/Standard Deviation, N=3)

(Mean Value/Standard Deviation, N=3)

(Mean Value/Standard Deviation, N=3)

Day 30: the final dosing day
* p<0.05 by Tukey-Kramer HSD test (Mean Value/Standard Deviation, N=10)

(Mean Value/Standard Deviation, N=3)

(Mean Value/Standard Deviation, N=3)

(Mean Value/Standard Deviation, N=3)

(Mean Value/Standard Deviation, N=3)

SEQUENCE LISTING

```
<160> NUMBER OF SEQ ID NOS: 171

<210> SEQ ID NO 1
<211> LENGTH: 28
<212> TYPE: PRT
<213> ORGANISM: Homo sapiens

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Homo sapiens

<400> SEQUENCE: 2

Gly Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 3
<211> LENGTH: 28
<212> TYPE: PRT
<213> ORGANISM: Unknown
```

-continued

```
<220> FEATURE:
<223> OTHER INFORMATION: Description of Unknown: Simian peptide

<400> SEQUENCE: 3

Gly Ser Ser Phe Leu Ser Pro Glu His Gln Arg Ala Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 27
<212> TYPE: PRT
<213> ORGANISM: Unknown
<220> FEATURE:
<223> OTHER INFORMATION: Description of Unknown: Bovine peptide

<400> SEQUENCE: 4

Gly Ser Ser Phe Leu Ser Pro Glu His Gln Lys Leu Gln Arg Lys Glu
1               5                   10                  15

Ala Lys Lys Pro Ser Gly Arg Leu Lys Pro Arg
            20                  25

<210> SEQ ID NO 5
<211> LENGTH: 27
<212> TYPE: PRT
<213> ORGANISM: Unknown
<220> FEATURE:
<223> OTHER INFORMATION: Description of Unknown: Bovine peptide

<400> SEQUENCE: 5

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 6
<211> LENGTH: 28
<212> TYPE: PRT
<213> ORGANISM: Unknown
<220> FEATURE:
<223> OTHER INFORMATION: Description of Unknown: Equine peptide

<400> SEQUENCE: 6

Gly Ser Ser Phe Leu Ser Pro Glu His His Lys Val Gln His Arg Lys
1               5                   10                  15

Glu Ser Lys Lys Pro Pro Ala Lys Leu Lys Pro Arg
            20                  25

<210> SEQ ID NO 7
<211> LENGTH: 28
<212> TYPE: PRT
<213> ORGANISM: Unknown
<220> FEATURE:
<223> OTHER INFORMATION: Description of Unknown: Porcine peptide

<400> SEQUENCE: 7

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 8
<211> LENGTH: 28
<212> TYPE: PRT
<213> ORGANISM: Unknown
```

```
<220> FEATURE:
<223> OTHER INFORMATION: Description of Unknown: Canine peptide

<400> SEQUENCE: 8

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 9
<211> LENGTH: 27
<212> TYPE: PRT
<213> ORGANISM: Unknown
<220> FEATURE:
<223> OTHER INFORMATION: Description of Unknown: Cervidae peptide

<400> SEQUENCE: 9

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 10
<211> LENGTH: 27
<212> TYPE: PRT
<213> ORGANISM: Unknown
<220> FEATURE:
<223> OTHER INFORMATION: Description of Unknown: Cervidae peptide

<400> SEQUENCE: 10

Gly Ser Ser Phe Leu Ser Pro Asp His Gln Lys Leu Gln Arg Lys Glu
1               5                   10                  15

Pro Lys Lys Pro Ser Gly Arg Leu Lys Pro Arg
            20                  25

<210> SEQ ID NO 11
<211> LENGTH: 27
<212> TYPE: PRT
<213> ORGANISM: Ovis sp.

<400> SEQUENCE: 11

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 12
<211> LENGTH: 27
<212> TYPE: PRT
<213> ORGANISM: Unknown
<220> FEATURE:
<223> OTHER INFORMATION: Description of Unknown: Goat peptide

<400> SEQUENCE: 12

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 13
<211> LENGTH: 27
<212> TYPE: PRT
<213> ORGANISM: Unknown
<220> FEATURE:
<223> OTHER INFORMATION: Description of Unknown: Feline peptide
```

```
<400> SEQUENCE: 13

Gly Ser Ser Phe Leu Ser Pro Glu His Gln Lys Val Gln Arg Lys Glu
1               5                   10                  15

Ser Lys Lys Pro Pro Ala Lys Leu Gln Pro Arg
            20                  25

<210> SEQ ID NO 14
<211> LENGTH: 28
<212> TYPE: PRT
<213> ORGANISM: Unknown
<220> FEATURE:
<223> OTHER INFORMATION: Description of Unknown: Rabbit peptide

<400> SEQUENCE: 14

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 15
<211> LENGTH: 28
<212> TYPE: PRT
<213> ORGANISM: Rattus sp.

<400> SEQUENCE: 15

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 16
<211> LENGTH: 27
<212> TYPE: PRT
<213> ORGANISM: Rattus sp.

<400> SEQUENCE: 16

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 17
<211> LENGTH: 28
<212> TYPE: PRT
<213> ORGANISM: Rattus sp.

<400> SEQUENCE: 17

Gly Ser Ser Phe Leu Ser Pro Glu His Gln Lys Thr Gln Gln Arg Lys
1               5                   10                  15

Glu Ser Lys Lys Pro Pro Ala Lys Leu Gln Pro Arg
            20                  25

<210> SEQ ID NO 18
<211> LENGTH: 26
<212> TYPE: PRT
<213> ORGANISM: Suncus murinus

<400> SEQUENCE: 18

Gly Ser Ser Phe Leu Ser Pro Glu His Gln Lys Gly Pro Lys Lys Asp
1               5                   10                  15

Pro Arg Lys Pro Pro Lys Leu Gln Pro Arg
            20                  25
```

<210> SEQ ID NO 19
<211> LENGTH: 27
<212> TYPE: PRT
<213> ORGANISM: Unknown
<220> FEATURE:
<223> OTHER INFORMATION: Description of Unknown: Whale peptide

<400> SEQUENCE: 19

Gly Ser Ser Phe Leu Ser Pro Glu His Gln Lys Leu Gln Arg Lys Glu
1               5                   10                  15

Ala Lys Lys Pro Ser Gly Arg Leu Lys Pro Arg
            20                  25

<210> SEQ ID NO 20
<211> LENGTH: 28
<212> TYPE: PRT
<213> ORGANISM: Meleagris sp.

<400> SEQUENCE: 20

Gly Ser Ser Phe Leu Ser Pro Ala Tyr Lys Asn Ile Gln Gln Gln Lys
1               5                   10                  15

Asp Thr Arg Lys Pro Thr Ala Arg Leu His Pro Arg
            20                  25

<210> SEQ ID NO 21
<211> LENGTH: 28
<212> TYPE: PRT
<213> ORGANISM: Gallus gallus domesticus

<400> SEQUENCE: 21

Gly Ser Ser Phe Leu Ser Pro Thr Tyr Lys Asn Ile Gln Gln Gln Lys
1               5                   10                  15

Asp Thr Arg Lys Pro Thr Ala Arg Leu His Arg Arg
            20                  25

<210> SEQ ID NO 22
<211> LENGTH: 26
<212> TYPE: PRT
<213> ORGANISM: Gallus gallus domesticus

<400> SEQUENCE: 22

Gly Ser Ser Phe Leu Ser Pro Thr Tyr Lys Asn Ile Gln Gln Gln Lys
1               5                   10                  15

Asp Thr Arg Lys Pro Thr Ala Arg Leu His
            20                  25

<210> SEQ ID NO 23
<211> LENGTH: 24
<212> TYPE: PRT
<213> ORGANISM: Gallus gallus domesticus

<400> SEQUENCE: 23

Gly Ser Ser Phe Leu Ser Pro Thr Tyr Lys Asn Ile Gln Gln Gln Lys
1               5                   10                  15

Asp Thr Arg Lys Pro Thr Ala Arg
            20

<210> SEQ ID NO 24
<211> LENGTH: 27
<212> TYPE: PRT
<213> ORGANISM: Unknown
<220> FEATURE:
<223> OTHER INFORMATION: Description of Unknown: Turtle peptide

```
<400> SEQUENCE: 24

Gly Ser Ser Phe Leu Ser Pro Glu Tyr Gln Asn Thr Gln Gln Arg Lys
1               5                   10                  15

Asp Pro Lys Lys His Thr Lys Leu Asn Arg Arg
            20                  25

<210> SEQ ID NO 25
<211> LENGTH: 30
<212> TYPE: PRT
<213> ORGANISM: Unknown
<220> FEATURE:
<223> OTHER INFORMATION: Description of Unknown: Frog peptide

<400> SEQUENCE: 25

Gly Leu Thr Phe Leu Ser Pro Ala Asp Met Gln Lys Ile Ala Glu Arg
1               5                   10                  15

Gln Ser Gln Asn Lys Leu Arg His Gly Asn Met Asn Arg Arg
            20                  25                  30

<210> SEQ ID NO 26
<211> LENGTH: 28
<212> TYPE: PRT
<213> ORGANISM: Unknown
<220> FEATURE:
<223> OTHER INFORMATION: Description of Unknown: Frog peptide

<400> SEQUENCE: 26

Gly Leu Thr Phe Leu Ser Pro Ala Asp Met Gln Lys Ile Ala Glu Arg
1               5                   10                  15

Gln Ser Gln Asn Lys Leu Arg His Gly Asn Met Asn
            20                  25

<210> SEQ ID NO 27
<211> LENGTH: 27
<212> TYPE: PRT
<213> ORGANISM: Unknown
<220> FEATURE:
<223> OTHER INFORMATION: Description of Unknown: Frog peptide

<400> SEQUENCE: 27

Gly Leu Thr Phe Leu Ser Pro Ala Asp Met Gln Lys Ile Ala Glu Arg
1               5                   10                  15

Gln Ser Gln Asn Lys Leu Arg His Gly Asn Met
            20                  25

<210> SEQ ID NO 28
<211> LENGTH: 24
<212> TYPE: PRT
<213> ORGANISM: Unknown
<220> FEATURE:
<223> OTHER INFORMATION: Description of Unknown: Eel peptide

<400> SEQUENCE: 28

Gly Ser Ser Phe Leu Ser Pro Ser Gln Arg Pro Gln Gly Lys Asp Lys
1               5                   10                  15

Lys Pro Pro Arg Val Gly Arg Arg
            20

<210> SEQ ID NO 29
<211> LENGTH: 21
<212> TYPE: PRT
<213> ORGANISM: Unknown
<220> FEATURE:
<223> OTHER INFORMATION: Description of Unknown: Eel peptide
```

```
<220> FEATURE:
<223> OTHER INFORMATION: C-terminus amidated

<400> SEQUENCE: 29

Gly Ser Ser Phe Leu Ser Pro Ser Gln Arg Pro Gln Gly Lys Asp Lys
1               5                   10                  15

Lys Pro Pro Arg Val
            20

<210> SEQ ID NO 30
<211> LENGTH: 25
<212> TYPE: PRT
<213> ORGANISM: Unknown
<220> FEATURE:
<223> OTHER INFORMATION: Description of Unknown: Catfish peptide

<400> SEQUENCE: 30

Gly Ser Ser Phe Leu Ser Pro Thr Gln Lys Pro Gln Asn Arg Gly Asp
1               5                   10                  15

Arg Lys Pro Pro Arg Val Gly Arg Arg
            20                  25

<210> SEQ ID NO 31
<211> LENGTH: 23
<212> TYPE: PRT
<213> ORGANISM: Unknown
<220> FEATURE:
<223> OTHER INFORMATION: Description of Unknown: Catfish peptide

<400> SEQUENCE: 31

Gly Ser Ser Phe Leu Ser Pro Thr Gln Lys Pro Gln Asn Arg Gly Asp
1               5                   10                  15

Arg Lys Pro Pro Arg Val Gly
            20

<210> SEQ ID NO 32
<211> LENGTH: 22
<212> TYPE: PRT
<213> ORGANISM: Unknown
<220> FEATURE:
<223> OTHER INFORMATION: Description of Unknown: Catfish peptide
<220> FEATURE:
<223> OTHER INFORMATION: C-terminus amidated

<400> SEQUENCE: 32

Gly Ser Ser Phe Leu Ser Pro Thr Gln Lys Pro Gln Asn Arg Gly Asp
1               5                   10                  15

Arg Lys Pro Pro Arg Val
            20

<210> SEQ ID NO 33
<211> LENGTH: 26
<212> TYPE: PRT
<213> ORGANISM: Unknown
<220> FEATURE:
<223> OTHER INFORMATION: Description of Unknown: Shark peptide

<400> SEQUENCE: 33

Gly Val Ser Phe His Pro Arg Leu Lys Glu Lys Asp Asp Asn Ser Ser
1               5                   10                  15

Gly Asn Ser Arg Lys Ser Asn Pro Lys Arg
            20                  25

<210> SEQ ID NO 34
<211> LENGTH: 17
```

```
<212> TYPE: PRT
<213> ORGANISM: Homo sapiens

<400> SEQUENCE: 34

Val Gln Gln Arg Lys Glu Ser Lys Lys Pro Pro Ala Lys Leu Gln Pro
1               5                   10                  15
Arg

<210> SEQ ID NO 35
<211> LENGTH: 16
<212> TYPE: PRT
<213> ORGANISM: Homo sapiens

<400> SEQUENCE: 35

Val Gln Arg Lys Glu Ser Lys Lys Pro Pro Ala Lys Leu Gln Pro Arg
1               5                   10                  15

<210> SEQ ID NO 36
<211> LENGTH: 17
<212> TYPE: PRT
<213> ORGANISM: Unknown
<220> FEATURE:
<223> OTHER INFORMATION: Description of Unknown: Simian peptide

<400> SEQUENCE: 36

Ala Gln Gln Arg Lys Glu Ser Lys Lys Pro Pro Ala Lys Leu Gln Pro
1               5                   10                  15
Arg

<210> SEQ ID NO 37
<211> LENGTH: 16
<212> TYPE: PRT
<213> ORGANISM: Unknown
<220> FEATURE:
<223> OTHER INFORMATION: Description of Unknown: Bovine peptide

<400> SEQUENCE: 37

Leu Gln Arg Lys Glu Ala Lys Lys Pro Ser Gly Arg Leu Lys Pro Arg
1               5                   10                  15

<210> SEQ ID NO 38
<211> LENGTH: 16
<212> TYPE: PRT
<213> ORGANISM: Unknown
<220> FEATURE:
<223> OTHER INFORMATION: Description of Unknown: Bovine peptide

<400> SEQUENCE: 38

Leu Gln Arg Lys Glu Pro Lys Lys Pro Ser Gly Arg Leu Lys Pro Arg
1               5                   10                  15

<210> SEQ ID NO 39
<211> LENGTH: 17
<212> TYPE: PRT
<213> ORGANISM: Unknown
<220> FEATURE:
<223> OTHER INFORMATION: Description of Unknown: Equine peptide

<400> SEQUENCE: 39

Val Gln His Arg Lys Glu Ser Lys Lys Pro Pro Ala Lys Leu Lys Pro
1               5                   10                  15
Arg

<210> SEQ ID NO 40
<211> LENGTH: 17
```

```
<212> TYPE: PRT
<213> ORGANISM: Unknown
<220> FEATURE:
<223> OTHER INFORMATION: Description of Unknown: Porcine peptide

<400> SEQUENCE: 40

Val Gln Gln Arg Lys Glu Ser Lys Lys Pro Ala Ala Lys Leu Lys Pro
1               5                   10                  15

Arg

<210> SEQ ID NO 41
<211> LENGTH: 17
<212> TYPE: PRT
<213> ORGANISM: Unknown
<220> FEATURE:
<223> OTHER INFORMATION: Description of Unknown: Canine peptide

<400> SEQUENCE: 41

Leu Gln Gln Arg Lys Glu Ser Lys Lys Pro Pro Ala Lys Leu Gln Pro
1               5                   10                  15

Arg

<210> SEQ ID NO 42
<211> LENGTH: 16
<212> TYPE: PRT
<213> ORGANISM: Unknown
<220> FEATURE:
<223> OTHER INFORMATION: Description of Unknown: Cervidae peptide

<400> SEQUENCE: 42

Leu Gln Arg Lys Glu Pro Lys Lys Pro Ser Gly Arg Leu Lys Pro Arg
1               5                   10                  15

<210> SEQ ID NO 43
<211> LENGTH: 16
<212> TYPE: PRT
<213> ORGANISM: Unknown
<220> FEATURE:
<223> OTHER INFORMATION: Description of Unknown: Cervidae peptide

<400> SEQUENCE: 43

Leu Gln Arg Lys Glu Pro Lys Lys Pro Ser Gly Arg Leu Lys Pro Arg
1               5                   10                  15

<210> SEQ ID NO 44
<211> LENGTH: 16
<212> TYPE: PRT
<213> ORGANISM: Ovis sp.

<400> SEQUENCE: 44

Leu Gln Arg Lys Glu Pro Lys Lys Pro Ser Gly Arg Leu Lys Pro Arg
1               5                   10                  15

<210> SEQ ID NO 45
<211> LENGTH: 16
<212> TYPE: PRT
<213> ORGANISM: Unknown
<220> FEATURE:
<223> OTHER INFORMATION: Description of Unknown: Goat peptide

<400> SEQUENCE: 45

Leu Gln Arg Lys Glu Pro Lys Lys Pro Ser Gly Arg Leu Lys Pro Arg
1               5                   10                  15

<210> SEQ ID NO 46
<211> LENGTH: 16
```

```
<212> TYPE: PRT
<213> ORGANISM: Unknown
<220> FEATURE:
<223> OTHER INFORMATION: Description of Unknown: Feline peptide

<400> SEQUENCE: 46

Val Gln Arg Lys Glu Ser Lys Lys Pro Pro Ala Lys Leu Gln Pro Arg
1               5                   10                  15

<210> SEQ ID NO 47
<211> LENGTH: 17
<212> TYPE: PRT
<213> ORGANISM: Unknown
<220> FEATURE:
<223> OTHER INFORMATION: Description of Unknown: Rabbit peptide

<400> SEQUENCE: 47

Val Gln Gln Arg Lys Glu Ser Lys Lys Pro Ala Ala Lys Leu Lys Pro
1               5                   10                  15

Arg

<210> SEQ ID NO 48
<211> LENGTH: 17
<212> TYPE: PRT
<213> ORGANISM: Rattus sp.

<400> SEQUENCE: 48

Ala Gln Gln Arg Lys Glu Ser Lys Lys Pro Pro Ala Lys Leu Gln Pro
1               5                   10                  15

Arg

<210> SEQ ID NO 49
<211> LENGTH: 16
<212> TYPE: PRT
<213> ORGANISM: Rattus sp.

<400> SEQUENCE: 49

Ala Gln Arg Lys Glu Ser Lys Lys Pro Pro Ala Lys Leu Gln Pro Arg
1               5                   10                  15

<210> SEQ ID NO 50
<211> LENGTH: 17
<212> TYPE: PRT
<213> ORGANISM: Rattus sp.

<400> SEQUENCE: 50

Thr Gln Gln Arg Lys Glu Ser Lys Lys Pro Pro Ala Lys Leu Gln Pro
1               5                   10                  15

Arg

<210> SEQ ID NO 51
<211> LENGTH: 15
<212> TYPE: PRT
<213> ORGANISM: Suncus murinus

<400> SEQUENCE: 51

Gly Pro Lys Lys Asp Pro Arg Lys Pro Lys Leu Gln Pro Arg
1               5                   10                  15

<210> SEQ ID NO 52
<211> LENGTH: 16
<212> TYPE: PRT
<213> ORGANISM: Unknown
<220> FEATURE:
<223> OTHER INFORMATION: Description of Unknown: Whale peptide
```

```
<400> SEQUENCE: 52

Leu Gln Arg Lys Glu Ala Lys Lys Pro Ser Gly Arg Leu Lys Pro Arg
1               5                   10                  15

<210> SEQ ID NO 53
<211> LENGTH: 17
<212> TYPE: PRT
<213> ORGANISM: Meleagris sp.

<400> SEQUENCE: 53

Ile Gln Gln Gln Lys Asp Thr Arg Lys Pro Thr Ala Arg Leu His Pro
1               5                   10                  15

Arg

<210> SEQ ID NO 54
<211> LENGTH: 17
<212> TYPE: PRT
<213> ORGANISM: Gallus gallus domesticus

<400> SEQUENCE: 54

Ile Gln Gln Gln Lys Asp Thr Arg Lys Pro Thr Ala Arg Leu His Arg
1               5                   10                  15

Arg

<210> SEQ ID NO 55
<211> LENGTH: 15
<212> TYPE: PRT
<213> ORGANISM: Gallus gallus domesticus

<400> SEQUENCE: 55

Ile Gln Gln Gln Lys Asp Thr Arg Lys Pro Thr Ala Arg Leu His
1               5                   10                  15

<210> SEQ ID NO 56
<211> LENGTH: 13
<212> TYPE: PRT
<213> ORGANISM: Gallus gallus domesticus

<400> SEQUENCE: 56

Ile Gln Gln Gln Lys Asp Thr Arg Lys Pro Thr Ala Arg
1               5                   10

<210> SEQ ID NO 57
<211> LENGTH: 16
<212> TYPE: PRT
<213> ORGANISM: Unknown
<220> FEATURE:
<223> OTHER INFORMATION: Description of Unknown: Turtle peptide

<400> SEQUENCE: 57

Thr Gln Gln Arg Lys Asp Pro Lys Lys His Thr Lys Leu Asn Arg Arg
1               5                   10                  15

<210> SEQ ID NO 58
<211> LENGTH: 20
<212> TYPE: PRT
<213> ORGANISM: Unknown
<220> FEATURE:
<223> OTHER INFORMATION: Description of Unknown: Frog peptide

<400> SEQUENCE: 58

Gln Lys Ile Ala Glu Arg Gln Ser Gln Asn Lys Leu Arg His Gly Asn
1               5                   10                  15
```

Met Asn Arg Arg
            20

<210> SEQ ID NO 59
<211> LENGTH: 18
<212> TYPE: PRT
<213> ORGANISM: Unknown
<220> FEATURE:
<223> OTHER INFORMATION: Description of Unknown: Frog peptide

<400> SEQUENCE: 59

Gln Lys Ile Ala Glu Arg Gln Ser Gln Asn Lys Leu Arg His Gly Asn
1               5                   10                  15

Met Asn

<210> SEQ ID NO 60
<211> LENGTH: 17
<212> TYPE: PRT
<213> ORGANISM: Unknown
<220> FEATURE:
<223> OTHER INFORMATION: Description of Unknown: Frog peptide

<400> SEQUENCE: 60

Gln Lys Ile Ala Glu Arg Gln Ser Gln Asn Lys Leu Arg His Gly Asn
1               5                   10                  15

Met

<210> SEQ ID NO 61
<211> LENGTH: 13
<212> TYPE: PRT
<213> ORGANISM: Unknown
<220> FEATURE:
<223> OTHER INFORMATION: Description of Unknown: Eel peptide

<400> SEQUENCE: 61

Gln Gly Lys Asp Lys Lys Pro Pro Arg Val Gly Arg Arg
1               5                   10

<210> SEQ ID NO 62
<211> LENGTH: 10
<212> TYPE: PRT
<213> ORGANISM: Unknown
<220> FEATURE:
<223> OTHER INFORMATION: Description of Unknown: Eel peptide

<400> SEQUENCE: 62

Gln Gly Lys Asp Lys Lys Pro Pro Arg Val
1               5                   10

<210> SEQ ID NO 63
<211> LENGTH: 14
<212> TYPE: PRT
<213> ORGANISM: Unknown
<220> FEATURE:
<223> OTHER INFORMATION: Description of Unknown: Catfish peptide

<400> SEQUENCE: 63

Gln Asn Arg Gly Asp Arg Lys Pro Pro Arg Val Gly Arg Arg
1               5                   10

<210> SEQ ID NO 64
<211> LENGTH: 12
<212> TYPE: PRT
<213> ORGANISM: Unknown
<220> FEATURE:
<223> OTHER INFORMATION: Description of Unknown: Catfish peptide

```
<400> SEQUENCE: 64

Gln Asn Arg Gly Asp Arg Lys Pro Pro Arg Val Gly
 1               5                  10

<210> SEQ ID NO 65
<211> LENGTH: 11
<212> TYPE: PRT
<213> ORGANISM: Unknown
<220> FEATURE:
<223> OTHER INFORMATION: Description of Unknown: Catfish peptide

<400> SEQUENCE: 65

Gln Asn Arg Gly Asp Arg Lys Pro Pro Arg Val
 1               5                  10

<210> SEQ ID NO 66
<211> LENGTH: 18
<212> TYPE: PRT
<213> ORGANISM: Unknown
<220> FEATURE:
<223> OTHER INFORMATION: Description of Unknown: Shark peptide

<400> SEQUENCE: 66

Lys Glu Lys Asp Asp Asn Ser Ser Gly Asn Ser Arg Lys Ser Asn Pro
 1               5                  10                  15

Lys Arg

<210> SEQ ID NO 67
<211> LENGTH: 17
<212> TYPE: PRT
<213> ORGANISM: Homo sapiens

<400> SEQUENCE: 67

Arg Pro Gln Leu Lys Ala Pro Pro Lys Lys Ser Glu Lys Arg Gln Gln
 1               5                  10                  15

Val

<210> SEQ ID NO 68
<211> LENGTH: 16
<212> TYPE: PRT
<213> ORGANISM: Homo sapiens

<400> SEQUENCE: 68

Arg Pro Gln Leu Lys Ala Pro Pro Lys Lys Ser Glu Lys Arg Gln Val
 1               5                  10                  15

<210> SEQ ID NO 69
<211> LENGTH: 17
<212> TYPE: PRT
<213> ORGANISM: Simian

<400> SEQUENCE: 69

Arg Pro Gln Leu Lys Ala Pro Pro Lys Lys Ser Glu Lys Arg Gln Gln
 1               5                  10                  15

Ala

<210> SEQ ID NO 70
<211> LENGTH: 16
<212> TYPE: PRT
<213> ORGANISM: Unknown
<220> FEATURE:
<223> OTHER INFORMATION: Description of Unknown: Bovine peptide

<400> SEQUENCE: 70
```

-continued

Arg Pro Lys Leu Arg Gly Ser Pro Lys Ala Glu Lys Arg Gln Leu
1               5                   10                  15

<210> SEQ ID NO 71
<211> LENGTH: 16
<212> TYPE: PRT
<213> ORGANISM: Unknown
<220> FEATURE:
<223> OTHER INFORMATION: Description of Unknown: Bovine peptide

<400> SEQUENCE: 71

Arg Pro Lys Leu Arg Gly Ser Pro Lys Pro Glu Lys Arg Gln Leu
1               5                   10                  15

<210> SEQ ID NO 72
<211> LENGTH: 17
<212> TYPE: PRT
<213> ORGANISM: Unknown
<220> FEATURE:
<223> OTHER INFORMATION: Description of Unknown: Equine peptide

<400> SEQUENCE: 72

Arg Pro Lys Leu Lys Ala Pro Pro Lys Lys Ser Glu Lys Arg His Gln
1               5                   10                  15

Val

<210> SEQ ID NO 73
<211> LENGTH: 17
<212> TYPE: PRT
<213> ORGANISM: Unknown
<220> FEATURE:
<223> OTHER INFORMATION: Description of Unknown: Porcine peptide

<400> SEQUENCE: 73

Arg Pro Lys Leu Lys Ala Ala Pro Lys Lys Ser Glu Lys Arg Gln Gln
1               5                   10                  15

Val

<210> SEQ ID NO 74
<211> LENGTH: 17
<212> TYPE: PRT
<213> ORGANISM: Unknown
<220> FEATURE:
<223> OTHER INFORMATION: Description of Unknown: Canine peptide

<400> SEQUENCE: 74

Arg Pro Gln Leu Lys Ala Pro Pro Lys Lys Ser Glu Lys Arg Gln Gln
1               5                   10                  15

Leu

<210> SEQ ID NO 75
<211> LENGTH: 16
<212> TYPE: PRT
<213> ORGANISM: Unknown
<220> FEATURE:
<223> OTHER INFORMATION: Description of Unknown: Cervidae peptide

<400> SEQUENCE: 75

Arg Pro Lys Leu Arg Gly Ser Pro Lys Pro Glu Lys Arg Gln Leu
1               5                   10                  15

<210> SEQ ID NO 76
<211> LENGTH: 16
<212> TYPE: PRT
<213> ORGANISM: Unknown
<220> FEATURE:

<223> OTHER INFORMATION: Description of Unknown: Cervidae peptide

<400> SEQUENCE: 76

Arg Pro Lys Leu Arg Gly Ser Pro Lys Lys Pro Glu Lys Arg Gln Leu
1               5                   10                  15

<210> SEQ ID NO 77
<211> LENGTH: 16
<212> TYPE: PRT
<213> ORGANISM: Ovis sp.

<400> SEQUENCE: 77

Arg Pro Lys Leu Arg Gly Ser Pro Lys Lys Pro Glu Lys Arg Gln Leu
1               5                   10                  15

<210> SEQ ID NO 78
<211> LENGTH: 16
<212> TYPE: PRT
<213> ORGANISM: Unknown
<220> FEATURE:
<223> OTHER INFORMATION: Description of Unknown: Goat peptide

<400> SEQUENCE: 78

Arg Pro Lys Leu Arg Gly Ser Pro Lys Lys Pro Glu Lys Arg Gln Leu
1               5                   10                  15

<210> SEQ ID NO 79
<211> LENGTH: 16
<212> TYPE: PRT
<213> ORGANISM: Unknown
<220> FEATURE:
<223> OTHER INFORMATION: Description of Unknown: Feline peptide

<400> SEQUENCE: 79

Arg Pro Gln Leu Lys Ala Pro Pro Lys Lys Ser Glu Lys Arg Gln Val
1               5                   10                  15

<210> SEQ ID NO 80
<211> LENGTH: 17
<212> TYPE: PRT
<213> ORGANISM: Unknown
<220> FEATURE:
<223> OTHER INFORMATION: Description of Unknown: Rabbit peptide

<400> SEQUENCE: 80

Arg Pro Lys Leu Lys Ala Ala Pro Lys Lys Ser Glu Lys Arg Gln Gln
1               5                   10                  15
Val

<210> SEQ ID NO 81
<211> LENGTH: 17
<212> TYPE: PRT
<213> ORGANISM: Rattus sp.

<400> SEQUENCE: 81

Arg Pro Gln Leu Lys Ala Pro Pro Lys Lys Ser Glu Lys Arg Gln Gln
1               5                   10                  15
Ala

<210> SEQ ID NO 82
<211> LENGTH: 16
<212> TYPE: PRT
<213> ORGANISM: Rattus sp.

<400> SEQUENCE: 82

```
Arg Pro Gln Leu Lys Ala Pro Pro Lys Ser Glu Lys Arg Gln Ala
1               5                   10                  15
```

<210> SEQ ID NO 83
<211> LENGTH: 17
<212> TYPE: PRT
<213> ORGANISM: Rattus sp.

<400> SEQUENCE: 83

```
Arg Pro Gln Leu Lys Ala Pro Pro Lys Lys Ser Glu Lys Arg Gln Gln
1               5                   10                  15

Thr
```

<210> SEQ ID NO 84
<211> LENGTH: 15
<212> TYPE: PRT
<213> ORGANISM: Suncus murinus

<400> SEQUENCE: 84

```
Arg Pro Gln Leu Lys Pro Pro Lys Arg Pro Asp Lys Lys Pro Gly
1               5                   10                  15
```

<210> SEQ ID NO 85
<211> LENGTH: 16
<212> TYPE: PRT
<213> ORGANISM: Unknown
<220> FEATURE:
<223> OTHER INFORMATION: Description of Unknown: Whale peptide

<400> SEQUENCE: 85

```
Arg Pro Lys Leu Arg Gly Ser Pro Lys Lys Ala Glu Lys Arg Gln Leu
1               5                   10                  15
```

<210> SEQ ID NO 86
<211> LENGTH: 17
<212> TYPE: PRT
<213> ORGANISM: Meleagris sp.

<400> SEQUENCE: 86

```
Arg Pro His Leu Arg Ala Thr Pro Lys Arg Thr Asp Lys Gln Gln Gln
1               5                   10                  15

Ile
```

<210> SEQ ID NO 87
<211> LENGTH: 17
<212> TYPE: PRT
<213> ORGANISM: Gallus gallus domesticus

<400> SEQUENCE: 87

```
Arg Arg His Leu Arg Ala Thr Pro Lys Arg Thr Asp Lys Gln Gln Gln
1               5                   10                  15

Ile
```

<210> SEQ ID NO 88
<211> LENGTH: 15
<212> TYPE: PRT
<213> ORGANISM: Gallus gallus domesticus

<400> SEQUENCE: 88

```
His Leu Arg Ala Thr Pro Lys Arg Thr Asp Lys Gln Gln Gln Ile
1               5                   10                  15
```

<210> SEQ ID NO 89
<211> LENGTH: 13

```
<212> TYPE: PRT
<213> ORGANISM: Gallus gallus domesticus

<400> SEQUENCE: 89

Arg Ala Thr Pro Lys Arg Thr Asp Lys Gln Gln Gln Ile
1               5                   10

<210> SEQ ID NO 90
<211> LENGTH: 16
<212> TYPE: PRT
<213> ORGANISM: Unknown
<220> FEATURE:
<223> OTHER INFORMATION: Description of Unknown: Turtle peptide

<400> SEQUENCE: 90

Arg Arg Asn Leu Lys Thr His Lys Lys Pro Asp Lys Arg Gln Gln Thr
1               5                   10                  15

<210> SEQ ID NO 91
<211> LENGTH: 20
<212> TYPE: PRT
<213> ORGANISM: Unknown
<220> FEATURE:
<223> OTHER INFORMATION: Description of Unknown: Frog peptide

<400> SEQUENCE: 91

Arg Arg Asn Met Asn Gly His Arg Leu Lys Asn Gln Ser Gln Arg Glu
1               5                   10                  15

Ala Ile Lys Gln
            20

<210> SEQ ID NO 92
<211> LENGTH: 18
<212> TYPE: PRT
<213> ORGANISM: Unknown
<220> FEATURE:
<223> OTHER INFORMATION: Description of Unknown: Frog peptide

<400> SEQUENCE: 92

Asn Met Asn Gly His Arg Leu Lys Asn Gln Ser Gln Arg Glu Ala Ile
1               5                   10                  15

Lys Gln

<210> SEQ ID NO 93
<211> LENGTH: 17
<212> TYPE: PRT
<213> ORGANISM: Unknown
<220> FEATURE:
<223> OTHER INFORMATION: Description of Unknown: Frog peptide

<400> SEQUENCE: 93

Met Asn Gly His Arg Leu Lys Asn Gln Ser Gln Arg Glu Ala Ile Lys
1               5                   10                  15

Gln

<210> SEQ ID NO 94
<211> LENGTH: 13
<212> TYPE: PRT
<213> ORGANISM: Unknown
<220> FEATURE:
<223> OTHER INFORMATION: Description of Unknown: Eel peptide

<400> SEQUENCE: 94

Arg Arg Gly Val Arg Pro Pro Lys Lys Asp Lys Gly Gln
1               5                   10
```

```
<210> SEQ ID NO 95
<211> LENGTH: 10
<212> TYPE: PRT
<213> ORGANISM: Unknown
<220> FEATURE:
<223> OTHER INFORMATION: Description of Unknown: Eel peptide

<400> SEQUENCE: 95

Val Arg Pro Pro Lys Lys Asp Lys Gly Gln
1               5                   10

<210> SEQ ID NO 96
<211> LENGTH: 14
<212> TYPE: PRT
<213> ORGANISM: Unknown
<220> FEATURE:
<223> OTHER INFORMATION: Description of Unknown: Catfish peptide

<400> SEQUENCE: 96

Arg Arg Gly Val Arg Pro Pro Lys Arg Asp Gly Arg Asn Gln
1               5                   10

<210> SEQ ID NO 97
<211> LENGTH: 12
<212> TYPE: PRT
<213> ORGANISM: Unknown
<220> FEATURE:
<223> OTHER INFORMATION: Description of Unknown: Catfish peptide

<400> SEQUENCE: 97

Gly Val Arg Pro Pro Lys Arg Asp Gly Arg Asn Gln
1               5                   10

<210> SEQ ID NO 98
<211> LENGTH: 11
<212> TYPE: PRT
<213> ORGANISM: Unknown
<220> FEATURE:
<223> OTHER INFORMATION: Description of Unknown: Catfish peptide

<400> SEQUENCE: 98

Val Arg Pro Pro Lys Arg Asp Gly Arg Asn Gln
1               5                   10

<210> SEQ ID NO 99
<211> LENGTH: 18
<212> TYPE: PRT
<213> ORGANISM: Unknown
<220> FEATURE:
<223> OTHER INFORMATION: Description of Unknown: Shark peptide

<400> SEQUENCE: 99

Arg Lys Pro Asn Ser Lys Arg Ser Asn Gly Ser Ser Asn Asp Asp Lys
1               5                   10                  15

Glu Lys

<210> SEQ ID NO 100
<211> LENGTH: 28
<212> TYPE: PRT
<213> ORGANISM: Homo sapiens
<220> FEATURE:
<221> NAME/KEY: DISULFID
<222> LOCATION: (7)..(23)
<223> OTHER INFORMATION: Cyclic peptide

<400> SEQUENCE: 100

Ser Leu Arg Arg Ser Ser Cys Phe Gly Gly Arg Met Asp Arg Ile Gly
```

```
                1               5                  10                 15
Ala Gln Ser Gly Leu Gly Cys Asn Ser Phe Arg Tyr
            20                  25

<210> SEQ ID NO 101
<211> LENGTH: 22
<212> TYPE: PRT
<213> ORGANISM: Homo sapiens
<220> FEATURE:
<221> NAME/KEY: DISULFID
<222> LOCATION: (6)..(22)
<223> OTHER INFORMATION: Cyclic peptide

<400> SEQUENCE: 101

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 102
<211> LENGTH: 22
<212> TYPE: PRT
<213> ORGANISM: Homo sapiens

<400> SEQUENCE: 102

Phe Val Pro Ile Phe Thr Tyr Gly Glu Leu Gln Arg Met Gln Glu Lys
1               5                   10                  15

Glu Arg Asn Lys Gly Gln
            20

<210> SEQ ID NO 103
<211> LENGTH: 30
<212> TYPE: PRT
<213> ORGANISM: Homo sapiens
<220> FEATURE:
<223> OTHER INFORMATION: C-terminus amidated

<400> SEQUENCE: 103

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 104
<211> LENGTH: 34
<212> TYPE: PRT
<213> ORGANISM: Homo sapiens

<400> SEQUENCE: 104

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 105
<211> LENGTH: 32
<212> TYPE: PRT
<213> ORGANISM: Homo sapiens
<220> FEATURE:
<223> OTHER INFORMATION: C-terminus amidated

<400> SEQUENCE: 105

Cys Gly Asn Leu Ser Thr Cys Met Leu Gly Thr Tyr Thr Gln Asp Phe
```

```
                1               5              10              15
Asn Lys Phe His Thr Phe Pro Gln Thr Ala Ile Gly Val Gly Ala Pro
                20              25              30
```

<210> SEQ ID NO 106
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (1)..(17)
<223> OTHER INFORMATION: Cyclic peptide

<400> SEQUENCE: 106

```
Cys Phe Gly Gly Arg Met Asp Arg Ile Gly Ala Gln Ser Gly Leu Gly
1               5                   10                  15
Cys Asn Ser Phe Arg Tyr Val Gln Gln Arg Lys Glu Ser Lys Lys Pro
                20                  25                  30
Pro Ala Lys Leu Gln Pro Arg
        35
```

<210> SEQ ID NO 107
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (18)..(34)
<223> OTHER INFORMATION: Cyclic peptide

<400> SEQUENCE: 107

```
Val Gln Gln Arg Lys Glu Ser Lys Lys Pro Pro Ala Lys Leu Gln Pro
1               5                   10                  15
Arg Cys Phe Gly Gly Arg Met Asp Arg Ile Gly Ala Gln Ser Gly Leu
                20                  25                  30
Gly Cys Asn Ser Phe Arg Tyr
        35
```

<210> SEQ ID NO 108
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (18)..(34)
<223> OTHER INFORMATION: Cyclic peptide

<400> SEQUENCE: 108

```
Arg Pro Gln Leu Lys Ala Pro Pro Lys Lys Ser Glu Lys Arg Gln Gln
1               5                   10                  15
Val Cys Phe Gly Gly Arg Met Asp Arg Ile Gly Ala Gln Ser Gly Leu
                20                  25                  30
Gly Cys Asn Ser Phe Arg Tyr
        35
```

<210> SEQ ID NO 109
<211> LENGTH: 34

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (18)..(34)
<223> OTHER INFORMATION: Cyclic peptide

<400> SEQUENCE: 109

Arg Pro Gln Leu Lys Ala Pro Pro Lys Lys Ser Glu Lys Arg Gln Gln
1               5                   10                  15

Val Cys Phe Gly Leu Lys Leu Asp Arg Ile Gly Ser Met Ser Gly Leu
            20                  25                  30

Gly Cys

<210> SEQ ID NO 110
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (1)..(17)
<223> OTHER INFORMATION: Cyclic peptide

<400> SEQUENCE: 110

Cys Phe Gly Leu Lys Leu Asp Arg Ile Gly Ser Met Ser Gly Leu Gly
1               5                   10                  15

Cys Val Gln Gln Arg Lys Glu Ser Lys Lys Pro Pro Ala Lys Leu Gln
            20                  25                  30

Pro Arg

<210> SEQ ID NO 111
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Phe Val Pro Ile Phe Thr Tyr Gly Glu Leu Gln Arg Ser Pro Glu His
1               5                   10                  15

Gln Arg Val Gln Gln Arg Lys Glu Ser Lys Lys Pro Pro Ala Lys Leu
            20                  25                  30

Gln Pro Arg
        35

<210> SEQ ID NO 112
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Phe Val Pro Ile Phe Thr Tyr Gly Glu Leu Gln Arg Glu His Gln Arg
1               5                   10                  15

Val Gln Gln Arg Lys Glu Ser Lys Lys Pro Pro Ala Lys Leu Gln Pro
            20                  25                  30
```

Arg

<210> SEQ ID NO 113
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Phe Val Pro Ile Phe Thr Tyr Gly Glu Leu Gln Arg Gln Arg Val Gln
1               5                   10                  15

Gln Arg Lys Glu Ser Lys Lys Pro Pro Ala Lys Leu Gln Pro Arg
            20                  25                  30
```

<210> SEQ ID NO 114
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

```
Phe Val Pro Ile Phe Thr Tyr Gly Glu Leu Gln Arg Val Gln Gln Arg
1               5                   10                  15

Lys Glu Ser Lys Lys Pro Pro Ala Lys Leu Gln Pro Arg
            20                  25
```

<210> SEQ ID NO 115
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Phe Val Pro Ile Phe Thr Tyr Gly Glu Leu Gln Arg Gln Arg Lys Glu
1               5                   10                  15

Ser Lys Lys Pro Pro Ala Lys Leu Gln Pro Arg
            20                  25
```

<210> SEQ ID NO 116
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

```
Phe Val Pro Ile Phe Thr Tyr Gly Glu Leu Gln Arg Lys Glu Ser Lys
1               5                   10                  15

Lys Pro Pro Ala Lys Leu Gln Pro Arg
            20                  25
```

<210> SEQ ID NO 117
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117
```

Phe Val Pro Ile Phe Thr Tyr Gly Glu Leu Gln Arg Ser Lys Lys Pro
1               5                   10                  15

Pro Ala Lys Leu Gln Pro Arg
            20

<210> SEQ ID NO 118
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Phe Val Pro Ile Phe Thr Tyr Gly Glu Leu Gln Arg Val Gln Gln Arg
1               5                   10                  15

Lys Glu Ser Lys Lys Pro Pro Ala Lys Leu Gln
            20                  25

<210> SEQ ID NO 119
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Phe Val Pro Ile Phe Thr Tyr Gly Glu Leu Gln Arg Val Gln Gln Arg
1               5                   10                  15

Lys Glu Ser Lys Lys Pro Pro Ala Lys
            20                  25

<210> SEQ ID NO 120
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Phe Val Pro Ile Phe Thr Tyr Gly Glu Leu Gln Arg Val Gln Gln Arg
1               5                   10                  15

Lys Glu Ser Lys Lys Pro Pro
            20

<210> SEQ ID NO 121
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Phe Val Pro Ile Phe Thr Tyr Gly Glu Leu Gln Arg Val Gln Gln Arg
1               5                   10                  15

Lys Glu Ser Lys Lys
            20

<210> SEQ ID NO 122
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 122

Phe Val Pro Ile Phe Thr Tyr Gly Glu Leu Gln Arg Val Gln Gln Arg
1               5                   10                  15

Lys Glu Ser

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Phe Val Pro Ile Phe Thr Tyr Gly Glu Leu Gln Arg Val Gln Gln Arg
1               5                   10                  15

Lys

<210> SEQ ID NO 124
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (1)..(17)
<223> OTHER INFORMATION: Cyclic peptide

<400> SEQUENCE: 124

Cys Phe Gly Leu Lys Leu Asp Arg Ile Gly Ser Met Ser Gly Leu Gly
1               5                   10                  15

Cys Val Gln Gln Arg Lys Glu Ser Lys Lys Pro Pro Ala Lys Leu Gln
            20                  25                  30

Pro Arg

<210> SEQ ID NO 125
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (6)..(22)
<223> OTHER INFORMATION: Cyclic peptide

<400> SEQUENCE: 125

Gly Leu Ser Lys Gly Cys Phe Gly Leu Lys Leu Asp Arg Ile Gly Ser
1               5                   10                  15

Met Ser Gly Leu Gly Cys Val Gln Gln Arg Lys Glu Ser Lys Lys Pro
            20                  25                  30

Pro Ala Lys Leu Gln Pro Arg
        35

<210> SEQ ID NO 126
<211> LENGTH: 51
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: DISULFID
<222> LOCATION: (18)..(34)
<223> OTHER INFORMATION: Cyclic peptide

<400> SEQUENCE: 126

Val Gln Gln Arg Lys Glu Ser Lys Lys Pro Pro Ala Lys Leu Gln Pro
1               5                   10                  15

Arg Cys Phe Gly Leu Lys Leu Asp Arg Ile Gly Ser Met Ser Gly Leu
            20                  25                  30

Gly Cys Val Gln Gln Arg Lys Glu Ser Lys Lys Pro Pro Ala Lys Leu
        35                  40                  45

Gln Pro Arg
    50

<210> SEQ ID NO 127
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Arg Pro Gln Leu Lys Ala Pro Pro Lys Lys Ser Glu Lys Arg Gln Gln
1               5                   10                  15

Val Cys Phe Gly Leu Lys Leu Asp Arg Ile Gly Ser Met Ser Gly Leu
            20                  25                  30

Gly Cys Val Gln Gln Arg Lys Glu Ser Lys Lys Pro Pro Ala Lys Leu
        35                  40                  45

Gln Pro Arg
    50

<210> SEQ ID NO 128
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (18)..(34)
<223> OTHER INFORMATION: Cyclic peptide

<400> SEQUENCE: 128

Val Gln Gln Arg Lys Glu Ser Lys Lys Pro Pro Ala Lys Leu Gln Pro
1               5                   10                  15

Arg Cys Phe Gly Leu Lys Leu Asp Arg Ile Gly Ser Met Ser Gly Leu
            20                  25                  30

Gly Cys

<210> SEQ ID NO 129
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (18)..(34)
<223> OTHER INFORMATION: Cyclic peptide
```

```
<400> SEQUENCE: 129

Arg Pro Gln Leu Lys Ala Pro Pro Lys Lys Ser Glu Lys Arg Gln Gln
1               5                   10                  15

Val Cys Phe Gly Leu Lys Leu Asp Arg Ile Gly Ser Met Ser Gly Leu
            20                  25                  30

Gly Cys

<210> SEQ ID NO 130
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: DISULFID
<222> LOCATION: (18)..(34)
<223> OTHER INFORMATION: Cyclic peptide
<220> FEATURE:
<223> OTHER INFORMATION: C-terminus amidated

<400> SEQUENCE: 130

Cys Phe Gly Leu Lys Leu Asp Arg Ile Gly Ser Met Ser Gly Leu Gly
1               5                   10                  15

Cys Val Gln Gln Arg Lys Glu Ser Lys Lys Pro Pro Ala Lys Leu Gln
            20                  25                  30

Pro Arg

<210> SEQ ID NO 131
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Phe Val Pro Ile Phe Thr Tyr Gly Glu Leu Gln Arg Val Gln Gln Arg
1               5                   10                  15

Lys Glu Lys Lys Pro Pro Ala Lys Leu Gln Pro Arg
            20                  25

<210> SEQ ID NO 132
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Phe Val Pro Ile Phe Thr Tyr Gly Glu Leu Gln Arg Val Gln Gln Arg
1               5                   10                  15

Lys Glu Phe Lys Lys Pro Pro Ala Lys Leu Gln Pro Arg
            20                  25

<210> SEQ ID NO 133
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133
```

```
Phe Val Pro Ile Phe Thr Tyr Gly Glu Leu Gln Arg Val Gln Gln Arg
1               5                   10                  15

Lys Glu Thr Lys Lys Pro Pro Ala Lys Leu Gln Pro Arg
            20                  25
```

<210> SEQ ID NO 134
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

```
Phe Val Pro Ile Phe Thr Tyr Gly Glu Leu Gln Arg Val Gln Gln Arg
1               5                   10                  15

Lys Glu Pro Lys Lys Pro Pro Ala Lys Leu Gln Pro Arg
            20                  25
```

<210> SEQ ID NO 135
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

```
Phe Val Pro Ile Phe Thr Tyr Gly Glu Leu Gln Arg Val Gln Gln Arg
1               5                   10                  15

Lys Glu Leu Lys Lys Pro Pro Ala Lys Leu Gln Pro Arg
            20                  25
```

<210> SEQ ID NO 136
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

```
Phe Val Pro Ile Phe Thr Tyr Gly Glu Leu Gln Arg Val Gln Gln Arg
1               5                   10                  15

Lys Glu Ala Lys Lys Pro Pro Ala Lys Leu Gln Pro Arg
            20                  25
```

<210> SEQ ID NO 137
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

```
Phe Val Pro Ile Phe Thr Tyr Gly Glu Leu Gln Arg Val Gln Gln Arg
1               5                   10                  15

Lys Asn Ser Lys Lys Pro Pro Ala Lys Leu Gln Pro Arg
            20                  25
```

<210> SEQ ID NO 138
<211> LENGTH: 29
<212> TYPE: PRT
<213> ORGANISM: Artificial Sequence
<220> FEATURE:

<223> OTHER INFORMATION: Description of Artificial Sequence: Synthetic
       peptide

<400> SEQUENCE: 138

Phe Val Pro Ile Phe Thr Tyr Gly Glu Leu Gln Arg Val Gln Gln Arg
1               5                   10                  15

Lys Gln Ser Lys Lys Pro Pro Ala Lys Leu Gln Pro Arg
            20                  25

<210> SEQ ID NO 139
<211> LENGTH: 29
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 139

Phe Val Pro Ile Phe Thr Tyr Gly Glu Leu Gln Arg Val Gln Gln Arg
1               5                   10                  15

Lys Asp Ser Lys Lys Pro Pro Ala Lys Leu Gln Pro Arg
            20                  25

<210> SEQ ID NO 140
<211> LENGTH: 27
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 140

Phe Val Pro Ile Phe Thr Tyr Gly Glu Leu Gln Arg Val Gln Gln Arg
1               5                   10                  15

Lys Lys Lys Pro Pro Ala Lys Leu Gln Pro Arg
            20                  25

<210> SEQ ID NO 141
<211> LENGTH: 29
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 141

Phe Val Pro Ile Phe Thr Tyr Gly Glu Leu Gln Arg Val Gln Gln Lys
1               5                   10                  15

Arg Asp Ser Arg Arg Pro Pro Ala Lys Leu Gln Pro Arg
            20                  25

<210> SEQ ID NO 142
<211> LENGTH: 29
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 142

Phe Val Pro Ile Phe Thr Tyr Gly Glu Leu Gln Arg Val Gln Gln Lys
1               5                   10                  15

Lys Ser Glu Lys Arg Pro Pro Ala Lys Leu Gln Pro Arg
            20                  25

```
<210> SEQ ID NO 143
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Phe Val Pro Ile Phe Thr Tyr Gly Glu Leu Gln Arg Val Gln Gln Arg
1               5                   10                  15

Lys Gly Glu Ser Lys Lys Pro Pro Ala Lys Leu Gln Pro Arg
            20                  25                  30

<210> SEQ ID NO 144
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Phe Val Pro Ile Phe Thr Tyr Gly Glu Leu Gln Arg Val Gln Gln Arg
1               5                   10                  15

Lys Glu Ser Gly Lys Lys Pro Pro Ala Lys Leu Gln Pro Arg
            20                  25                  30

<210> SEQ ID NO 145
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Phe Val Pro Ile Phe Thr Tyr Gly Glu Leu Gln Arg Val Gln Gln Arg
1               5                   10                  15

Lys Gly Gly Glu Ser Lys Lys Pro Pro Ala Lys Leu Gln Pro Arg
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Phe Val Pro Ile Phe Thr Tyr Gly Glu Leu Gln Arg Val Gln Gln Arg
1               5                   10                  15

Lys Gly Gly Glu Ser Gly Lys Lys Pro Pro Ala Lys Leu Gln Pro Arg
            20                  25                  30

<210> SEQ ID NO 147
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Phe Val Pro Ile Phe Thr Tyr Gly Glu Leu Gln Arg Val Gln Gln Arg
1               5                   10                  15
```

-continued

Lys Glu Ser Lys Lys Ala Lys Leu Gln Pro Arg
            20                  25

<210> SEQ ID NO 148
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Phe Val Pro Ile Phe Thr Tyr Gly Glu Leu Gln Arg Val Gln Gln Arg
1               5                   10                  15

Lys Glu Ser Lys Lys Ala Lys Leu Ala Ala Leu Lys Ala
            20                  25

<210> SEQ ID NO 149
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Phe Val Pro Ile Phe Thr Tyr Gly Glu Leu Gln Arg Val Gln Gln Arg
1               5                   10                  15

Lys Glu Ser Lys Lys Pro Pro Ala Lys Leu Ala Ala Leu Lys Ala
            20                  25                  30

<210> SEQ ID NO 150
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Phe Val Pro Ile Phe Thr Tyr Gly Glu Leu Gln Arg Val Gln Gln Arg
1               5                   10                  15

Lys Glu Ser Lys Lys Pro Pro Ala Glu Leu Ala Ala Leu Glu Ala
            20                  25                  30

<210> SEQ ID NO 151
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Phe Val Pro Ile Phe Thr Tyr Gly Glu Leu Gln Arg Val Gln Gln Arg
1               5                   10                  15

Lys Glu Ser Lys Lys Pro Pro Ala Glu Leu Ala Ala Leu Lys Ala
            20                  25                  30

<210> SEQ ID NO 152
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 152

Phe Val Pro Ile Phe Thr Tyr Gly Glu Leu Gln Arg Val Gln Gln Arg
1               5                   10                  15

Lys Glu Ser Lys Lys Met Ile Thr Ile Arg
            20                  25

<210> SEQ ID NO 153
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Phe Val Pro Ile Phe Thr Tyr Gly Glu Leu Gln Arg Val Gln Gln Arg
1               5                   10                  15

Lys Glu Ser Lys Lys Pro Pro Met Ile Thr Ile Arg
            20                  25

<210> SEQ ID NO 154
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Phe Val Pro Ile Phe Thr Tyr Gly Glu Leu Gln Arg Lys Glu Ser Lys
1               5                   10                  15

Lys Pro Pro Ala Lys Leu Ala Ala Leu Lys Ala
            20                  25

<210> SEQ ID NO 155
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Phe Val Pro Ile Phe Thr Tyr Gly Glu Leu Gln Arg Val Gln Gln Lys
1               5                   10                  15

Lys Ala Tyr Ser Pro Asp Lys Glu Arg Lys Pro Pro Ala Leu Gln Pro
            20                  25                  30

Arg

<210> SEQ ID NO 156
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Phe Val Pro Ile Phe Thr Tyr Gly Glu Leu Gln Arg Val Gln Gln Lys
1               5                   10                  15

Lys Ala Tyr Ser Pro Asp Lys Glu Arg Lys Pro Pro Ala Lys Leu Gln
            20                  25                  30

Pro Arg

<210> SEQ ID NO 157
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gly Leu Ser Lys Gly Cys Phe Gly Leu Lys Leu Asp Arg Ile Gly Ser
1               5                   10                  15

Met Ser Gly Leu Gly Cys Val Gln Gln Arg Lys Asp Ser Lys Lys Pro
            20                  25                  30

Pro Ala Lys Leu Gln Pro Arg
        35

<210> SEQ ID NO 158
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Cys Phe Gly Leu Lys Leu Asp Arg Ile Gly Ser Met Ser Gly Leu Gly
1               5                   10                  15

Cys Ala Gly Ser Val Asp His Lys Gly Lys Gln Arg Lys Val Val Asp
            20                  25                  30

His Pro Lys Arg
        35

<210> SEQ ID NO 159
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
    50

<210> SEQ ID NO 160
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ser Pro Lys Met Val Gln Gly Ser Gly Cys Phe Gly Arg Lys Met Asp
1               5                   10                  15

Arg Ile Ser Ser Ser Gly Leu Gly Cys Lys Val Leu Arg Arg His
            20                  25                  30

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ala Gly Ser Val Asp His Lys Gly Lys Gln
1               5                   10

<210> SEQ ID NO 162
<211> LENGTH: 6
<212> TYPE: PRT
<213> ORGANISM: Unknown
<220> FEATURE:
<223> OTHER INFORMATION: Description of Unknown: Core sequence peptide

<400> SEQUENCE: 162

Arg Lys Glu Ser Lys Lys
1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Lys Lys Ser Glu Lys Arg
1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Lys Lys Ala Tyr Ser Pro Lys
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Glu
<220> FEATURE:
<221> NAME/KEY: MOD_RES
<222> LOCATION: (7)..(7)
<223> OTHER INFORMATION: Lys or Glu

<400> SEQUENCE: 165

Ala Xaa Leu Ala Ala Leu Xaa Ala
1               5

<210> SEQ ID NO 166

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Lys Lys Pro Pro Ala Lys Leu Gln Pro Arg
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Pro Pro Ala Glu Leu Ala Ala Leu Glu Ala
1               5                   10

<210> SEQ ID NO 168
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Glu Ser Lys Lys
1

<210> SEQ ID NO 169
<211> LENGTH: 58
<212> TYPE: PRT
<213> ORGANISM: Homo sapiens

<400> SEQUENCE: 169

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
                20                  25                  30

Leu Ser Lys Gly Gly Leu Ser Lys Gly Cys Phe Gly Leu Lys Leu Asp
        35                  40                  45

Arg Ile Gly Ser Met Ser Gly Leu Gly Cys
    50                  55

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Arg Lys Tyr Lys Gly Ala Asn Lys Lys
1               5

<210> SEQ ID NO 171
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 171

Gly Leu Ser Lys Gly Cys Phe Gly Leu Lys Leu Asp Arg Ile Gly Ser
1               5                   10                  15

Met Ser Gly Leu Gly Cys Val Gln Gln Arg Lys Asp Ser Lys Lys Pro
            20                  25                  30

Pro Ala Lys Leu Gln Pro Arg
            35
```

PEPTIDE HAVING AN EXTENDING ACTION FOR HALF-LIFE OF OBJECT PEPTIDE IN PLASMA

CROSS REFERENCE TO RELATED APPLICATIONS

This application is the National Stage of International Application No. PCT/JP2009/059464, filed May 22, 2009, and claims benefit of Japanese Application Nos. 2008-136106, filed May 23, 2008, both of which are herein incorporated by reference in their entirety.

SEQUENCE LISTING

The instant application contains a sequence listing which has been submitted in ASCII format via EFS-Web and is hereby incorporated by reference in its entirety. Said ASCII copy, created on Jun. 22, 2012, is named 2587US21.txt and is 55,725 bytes in size.

TECHNICAL FIELD

The present invention relates to a peptide which is able to give therapeutic usefulness by improving the pharmacokinetics in vivo of the object peptide and giving the pharmacokinetics in vivo meeting the treating object, to a chimeric peptide where the pharmacokinetics in vivo is improved and the physiological activity of the object peptide is available, to a pharmaceutical composition containing the chimeric peptide and to a process for producing the chimeric peptide.

BACKGROUND ART

Even when a physiologically peptide which is able to be applied as a drug is present, some of the peptide has a short half-life in plasma and, in its application for therapeutic purpose, it is necessary to attempt the achievement by means of the continuous administration by intravenous or subcutaneous means or by administration of a DDS preparation of a sustained release type. Therefore, much time and cost for a long period of time are necessary for actual application.

For example, as an example where the half-life in plasma of the physiologically active peptide is extended and development as a drug is conducted, there is a case of glucagons-like peptide-1 (Non-Patent Document 1). In clinical studies for clarifying the action of the physiologically active peptide, a sustained release intravenous administration has been much used (Non-Patent Document 2) and, for the treatment of type 2 diabetes mellitus, a peptide where half-like is extended whereby a bolus subcutaneous administration is possible has been created. As such, in order to develop as an actual treating agent, there is a case where development of derivatives where a half-life is extended is necessary and, in such a case, physiologically active peptide derivatives are chemically synthesized or, even in the case of different type of natural peptide, that having a long half-life has been developed (Non-Patent Documents 3 to 5).

When a physiologically active peptide having a short half-life is to be applied as a drug, there is an attempt where it is bonded to a protein having a long half-life so that the half-life of the physiologically active peptide is made near the half-life of the protein. For example, an attempt such as that the object physiologically active protein and the protein are bonded via a spacer having a bonding group to a serum albumin has been in a testing stage (Non-Patent Document 6).

Accordingly, for subjecting the physiologically active peptide having a short half-life to a practical use, it has been expected that the pharmacokinetics in vivo is improved by adding a substance which is able to extent the half-life whereby the physiologically active peptide which was unable to exhibit a therapeutic effect by the prior art is applied to a medical purpose.

Attempts where the physiologically active peptide having a short half-like is modified so as to apply it as a drug have been widely carried out already. It has been attempted to stabilize the peptide, to give a sustaining property by an improvement in the preparation, etc. and examples where the practical implementation was successful have been known as well.

On the other hand, ghrelin is a hormone which was found in the stomach in 1999, has an amino acid sequence comprising 28 residues and is a peptide having a very unusual chemical structure where the third amino acid from the amino terminal of the sequence is acylated with fatty acid (Non-Patent Document 6 and Patent Document 1). Ghrelin is an endogenous brain- and digestive tract-hormone (Non-Patent Document 7) which acts on a growth hormone secretagogue-receptor 1a (GHS-R1a) (Non-Patent Document 7) to promote the secretion of growth hormone (GH) from pituitary gland.

Further, ghrelin was firstly isolated and purified from rats as an endogenous GHS for GHS-R1a. Moreover, ghrelin having the similar primary structure has been also isolated from vertebrate animals other than rat such as human, mouse, swine, domestic fowl, eel, cattle, horse, sheep, frog, rainbow trout or dog and the amino acid sequence thereof has been known already (Patent Document 1 and Non-Patent Document 8). All of the above ghrelin is a peptide where a side-chain hydroxyl group of the serine residue or threonine residue at 3-position is acylated by fatty acid such as octanoic acid or decanoic acid and, with regard to the physiologically active peptide having such a hydrophobically modified structure, there has been no example of being isolated from living body except ghrelin.

In the recent studies, it has been clarified that ghrelin promotes the appetite, that a subcutaneous administration of ghrelin increases body weight and body fat (Non-Patent Documents 9 to 11) and that an action such as improving the cardiac function is available (Non-Patent Documents 12 to 14). Further, ghrelin has a promoting action for GH secretion and a promoting action for appetite and it has been expected that an action where fat is burned via the action of GH so as to convert into energy or an effect where anabolic action of GH is expressed so as to potentiate the muscle is able to be more effectively brought out by promotion of appetite (Non-Patent Document 15).

However, the current status is that, although the active center of ghrelin is shown to be an N-terminal moiety having an acyl group (Patent Document 1), there are still ambiguous points for the physiological significance of the C terminal moiety.

CITATION LIST

[Patent Literature]
[PTL 1] WO 01/07475
[Non-Patent Literatures]
[NPL 1] Mojsov S, Weir G C, Habener J F. J Clin Invest. 1987, 79(2):616-619.
[NPL 2] Nauck M A, Heimesaat M M, Orskov C, Hoist J J, Ebert R, Creutzfeldt W., J Clin Invest. 1993, 91(1):301-307.
[NPL 3] O'Harte F P, Mooney M H, Lawlor A, Flatt P R., Biochim Biophys Acta. 2000, 6:1474(1):13-22.

[NPL 4] Madsbad S, Schmitz O, Ranstam J, Jakobsen G, Matthews D R., Diabetes Care. 2004, 27(6):1335-1342.

[NPL 5] DeFronzo R A, Ratner R E, Han J, Kim D D, Fineman M S, Baron A D., Diabetes Care. 2005, 28(5):1092-1100.

[NPL 6] Kim J G, Baggio L L, Bridon D P, Castaigne J P, Robitaille M F, Jetté L, Benquet C, Drucker D J., Diabetes. 2003, 52(3):751-759.

[NPL 7] Kojima M, Hosoda H, Date Y, Nakazato M, Matsuo H, Kangawa K., 1: Nature. 1999, 9:402(6762):656-660.

[NPL 8] Kojima M, Samukawa K., Seikagaku. 2007, 79(9):853-867.

[NPL 9] Choi K, Roh S G, Hong Y H, Shrestha Y B, Hishikawa D, Chen C, Kojima M, Kangawa K, Sasaki S., Endocrinology. 2003, 144(3):754-9.

[NPL 10] Neary N M, Small C J, Wren A M, Lee J L, Druce M R, Palmieri C, Frost G S, Ghatei M A, Coombes R C, Bloom S R., J Clin Endocrinol Metab. 2004, 89(6):2832-6.

[NPL 11] Akamizu T, Iwakura H, Ariyasu H, Hosoda H, Murayama T, Yokode M, Teramukai S, Seno H, Chiba T, Noma S, Nakai Y, Fukunaga M, Nakai Y, Kangawa K., FD Clinical Study Team. Eur J. Endocrinol. 2008, 158(4):491-8.

[NPL 12] Nagaya N, Kojima M, Uematsu M, Yamagishi M, Hosoda H, Oya H, Hayashi Y, Kangawa K., Am J Physiol Regul Integr Comp Physiol. 2001, 80(5):R1483-7.

[NPL 13] Nagaya N, Miyatake K, Uematsu M, Oya H, Shimizu W, Hosoda H, Kojima M, Nakanishi N, Mori H, Kangawa K., 1: J Clin Endocrinol Metab. 2001, 86(12):5854-5859.

[NPL 14] Nagaya N, Uematsu M, Kojima M, Ikeda Y, Yoshihara F, Shimizu W, Hosoda H, Hirota Y, Ishida H, Mori. H, Kangawa K., Circulation. 2001, 18; 104(12):1430-1435.

[NPL 15] Korbonits M, Goldstone A P, Gueorquiev M, Grossman A B, Front Neuroendocrinol., 2004, 25:27-68.

SUMMARY OF INVENTION

Technical Problem

An object of the present invention is to provide a peptide having an action of extending the half-life of a physiologically active peptide which is not suitable as a drug due to its short half-life in plasma; a chimeric peptide having a physiological activity of the object peptide and being able to be practically used as a drug due to its extension of half-life in plasma; and a process for producing the chimeric peptide, etc.

Solution to Problem

The present inventors have attempted to develop a peptide which is able to extend its half-life in plasma by addition of a peptide having an aimed physiological activity (hereinafter, it will be called the object peptide) which had to be intravenously or subcutaneously injected continuously for applying as a drug due to its short half-like in plasma and have found an amino acid sequence which is to become a half-life-extension motive in the C terminal moiety of the amino acid sequence of ghrelin. The peptide having an amino acid sequence which is able to extent the half-life is called a half-life-extension peptide in the present invention.

Thus, it has been found that, when the half-life-extension peptide is bonded to an N terminal side, C terminal side or both terminals of the object peptide (such as atrial natriuretic peptide (ANP), C type natriuretic peptide (CNP) or motilin), the half-life in plasma is able to be extended while the physiological activity of the object peptide is still retained. In the present invention, a peptide which is produced by bonding the half-life-extension peptide with the object peptide and has an extended half-life in plasma as compared with the object peptide where the physiological activity of the object peptide is still able to be retained is called a chimeric peptide.

It has been also found that the amino acid sequence concerning the half-life-extension peptide is able to be used not only in the case based on the natural amino acid sequence but also in the case based on the reversed sequence where the N terminal and C terminal thereof are reversed or on the case based on the sequence in which the N terminal and the C terminal are partly reversed.

It has been further found that the chimeric peptide has resistance to an enzyme which decomposes the object peptide (such as neutral endopeptidase) and, the same as in the case of an object peptide of a native, it does not show an antigenic property even upon repeated administrations but is able to be safely used.

Furthermore, when the object peptide of a native and the chimeric peptide are administered to individuals in the same dose and the same method of use, a sufficient aimed physiological action is able to be achieved in living body if a half-life-extension peptide is bonded to the peptide so as to extent the half-life even when the dose is unable to give a sufficient aimed physiological action by the use of the object peptide only. As a result, it has been shown that the method of use which is not a continuous injection is able to give the adaptability as a drug. Thus, it has been found that, when the half-life-extension peptide according to the present invention is added to the object peptide where a continuous intravenous or subcutaneous administration is necessary due to its short half-life, a bolus administration is now possible and, moreover, the aimed activity is able to be easily achieved in the chimeric peptide as compared with the object peptide of a native.

The present invention has been achieved based on the above finding and it relates to the followings.

Item 1:

A peptide of the following (I) or (II).

(I) a peptide represented by the formula B, A-B, B-C or A-B-C in which A, B and C each is represented by the following (1), (2) and (3) and, when it is bonded to other object peptide, it is able to extent the half-life in plasma as compared with the object peptide where the physiological activity of the object peptide is still retained.

(II) a peptide comprising a reversed sequence of the peptide of (I); a sequence which is represented by A-B in (I) and A or B is reversed; a sequence which is represented by B-C in (I) and B or C is reversed; or a sequence which is represented by A-B-C in (I) and A, B, C, A and B, B and C or A and C is reserved.

(1) A is a peptide comprising 1 to 14 of any amino acid(s)

(2) B is a peptide represented by the formula 1:

(Wk-Xl-Y-Zm-Wn)-(Wo-Xp-Y-Zq-Wr)s (In the formula 1, W is a basic amino acid; X and Z are any amino acids; Y is an acidic amino acid; k is 1 or 2; l is an integer of $4 \geq l \geq 0$; m is an integer of $2 \geq m \geq 0$; $4 \geq l+m \geq 0$; n is 1 or 2; o is 1 or 2; p is an integer of $4 \geq p \geq 0$; q is an integer of $2 \geq q \geq 0$; $4 \geq p+q \geq 0$; r is 1 or 2; and s is 0 or 1.)

(3) C is a peptide comprising 2 to 14 of any amino acids.

Item 2:

The peptide according to item 1, wherein B is a peptide where s is 1 in the formula 1.

Item 3:

The peptide according to item 2, wherein o is 0, p is 0, q is 0 and r is 2 in the formula 1.

Item 4:
The peptide according to item 1, wherein C contains 4 to 9 amino acid sequences being able to take α helix structure.

Item 5:
The peptide according to item 4, wherein C has a Pro sequence between its terminal and the amino acid sequence being able to take α helix structure.

Item 6:
A peptide represented by the formula B, A-B, B-C or A-B-C and, in the formula, A, B and C each is the following (1) or (2) and, when it is bonded to other peptide, its half-life is able to be extended where the physiological activity is still retained.

(1) A is an amino acid sequence of one or more amino acid numbers 1 to 4 continuing to B in SEQ ID No: 34 or an amino acid sequence where one or some amino acid(s) in the above amino acid sequence is/are deleted, substituted and/or added;

B is an amino acid sequence of amino acid numbers 5 to 9 in SEQ ID No: 34 or an amino acid sequence where one or some amino acid(s) in the above amino acid sequence is/are deleted, substituted and/or added; and C is an amino acid sequence of one or more amino acid numbers 10 to 17 continuing to B in SEQ ID No: 34 or an amino acid sequence where one or some amino acid(s) in the above amino acid sequence is/are deleted, substituted and/or added.

(2) A is an amino acid sequence of one or more amino acid numbers 1 to 8 continuing to B in SEQ ID No: 67 or an amino acid sequence where one or some amino acid(s) in the above amino acid sequence is/are deleted, substituted and/or added;

B is an amino acid sequence of amino acid numbers 9 to 13 in SEQ ID No: 67 or an amino acid sequence where one or some amino acid(s) in the above amino acid sequence is/are deleted, substituted and/or added; and C is an amino acid sequence of one or more amino acid numbers 14 to 17 continuing to B in SEQ ID No: 67 or an amino acid sequence where one or some amino acid(s) in the above amino acid sequence is/are deleted, substituted and/or added.

Item 7:
The peptide according to item 6, wherein it is represented by the formula: B in which B is a sequence selected from the group consisting of the amino acid numbers 5 to 9 in SEQ ID Nos: 34, 36, 39 to 41, 47, 48, 50 and 53 to 57; the amino acid numbers 4 to 8 in SEQ ID Nos: 35, 37, 38, 42 to 46, 49 and 52; the amino acid numbers 2 to 6 in SEQ ID Nos: 58 to 60; the amino acid numbers 3 to 6 in SEQ ID Nos: 61 and 62: the amino acid numbers 3 to 7 in SEQ ID Nos: 63 to 65; and the amino acid numbers 1 to 3 in SEQ ID No: 66.

Item 8:
The peptide according to item 6, wherein it is represented by the formula: A-B or B-C in which B is a sequence selected from the group consisting of the amino acid numbers 5 to 9 in SEQ ID Nos: 34, 36, 39 to 41, 47, 48, 50 and 53 to 57; the amino acid numbers 4 to 8 in SEQ ID Nos: 35, 37, 38, 42 to 46, 49 and 52; the amino acid numbers 2 to 6 in SEQ ID Nos: 58 to 60; the amino acid numbers 3 to 6 in SEQ ID Nos: 61 and 62: the amino acid numbers 3 to 7 in SEQ ID Nos: 63 to 65; and the amino acid numbers 1 to 3 in SEQ ID No: 66, A is a sequence selected from the group consisting of a sequence comprising at least one amino acid continuing from the C terminal side of amino acid numbers 1 to 4 in SEQ ID Nos: 34, 36, 39 to 41, 47, 48, 50 and 52 to 57; a sequence comprising at least one amino acid continuing from the C terminal side of amino acid numbers 1 to 3 in SEQ ID Nos: 35, 37, 38, 42 to 46, 49 and 52; a sequence of amino acid number 1 in SEQ ID Nos: 58 to 60; and a sequence comprising at least one amino acid continuing from the C terminal side of amino acid numbers 1 to 2 in SEQ ID Nos: 61 to 65, C is a sequence selected from the group consisting of a sequence comprising at least one amino acid continuing from N-terminal side of amino acid numbers 10 to 17 in SEQ ID Nos: 34, 36, 39 to 41, 47, 48, 50 and 53 to 54; a sequence comprising at least one amino acid continuing from N terminal side of amino acid numbers 9 to 16 in SEQ ID Nos: 35, 37, 38, 42 to 46, 49 and 52; a sequence comprising at least one amino acid continuing from N terminal side of amino acid numbers 10 to 16 in SEQ ID No: 57; a sequence comprising at least one amino acid continuing from N terminal side of amino acid numbers 7 to 20 in SEQ ID No: 58; a sequence comprising at least one amino acid continuing from N terminal side of amino acid numbers 7 to 13 in SEQ ID No: 61; a sequence comprising at least one amino acid continuing from N terminal side of amino acid numbers 8 to 14 in SEQ ID No: 63; and a sequence comprising at least one amino acid continuing from N terminal side of amino acid numbers 4 to 18 in SEQ ID No: 66.

Item 9:
The peptide according to item 6, wherein it is represented by the formula: A-B-C and, in the formula, A, B and C are the same as those in item 8.

Item 10:
The peptide according to item 6, wherein it is represented by the formula: B and, in the formula, B is a sequence selected from the group consisting of amino acid numbers 9 to 13 in SEQ ID Nos: 67 to 87; amino acid numbers 15 to 19 in SEQ ID No: 91; amino acid numbers 8 to 11 in SEQ ID No: 94; amino acid numbers 8 to 12 in SEQ ID No: 96; and amino acid numbers 16 to 18 in SEQ ID No: 99.

Item 11:
The peptide according to item 6, wherein it is represented by the formula: A-B or B-C and, in the formula, B is a sequence selected from the group consisting of amino acid numbers 9 to 13 in SEQ ID Nos: 67 to 87; amino acid numbers 8 to 12 in SEQ ID No: 90; amino acid numbers 15 to 19 in SEQ ID No: 91; amino acid numbers 8 to 11 in SEQ ID No: 94; amino acid numbers 8 to 12 in SEQ ID No: 96; and amino acid numbers 16 to 18 in SEQ ID No: 99, A is a sequence selected from the group consisting of a sequence comprising at least one amino acid continuing from the C terminal side of amino acid numbers 1 to 8 in SEQ ID Nos: 67 to 87; a sequence comprising at least one amino acid continuing from the C terminal side of amino acid numbers 1 to 7 in SEQ ID No: 90; a sequence comprising at least one amino acid continuing from the C terminal side of amino acid numbers 1 to 14 in SEQ ID No: 91; a sequence comprising at least one amino acid continuing from the C terminal side of amino acid numbers 1 to 7 in SEQ ID Nos: 94 and 96; a sequence comprising at least one amino acid continuing from the C terminal side of amino acid numbers 1 to 15 in SEQ ID No: 99 and C is a sequence selected from the group consisting of a sequence comprising at least one amino acid continuing from the N terminal side of amino acid numbers 14 to 17 in SEQ ID Nos: 67, 69, 72 to 74, 80, 81, 83 and 86 to 87; a sequence comprising at least one amino acid continuing from the N terminal side of amino acid numbers 14 to 16 in SEQ ID Nos: 68, 70, 71, 75 to 79, 82 and 85; a sequence comprising at least one amino acid continuing from the N terminal side of amino acid numbers 13 to 16 in SEQ ID No: 90; an amino acid number 20 in SEQ ID No: 91, a sequence comprising at least one amino acid continuing from the N terminal side of amino acid numbers 12 to 13 in SEQ ID No: 94; and a sequence comprising at least one amino acid continuing from the N terminal side of amino acid numbers 13 to 14 in SEQ ID No: 96.

Item 12:

The peptide according to item 6, wherein it is represented by the formula: A-B-C and, in the formula, A, B and C are the same as those in item 11.

Item 13:

The peptide according to item 6, wherein it is represented by the formula: B and, in the formula, B is a sequence selected from the group consisting of amino acid numbers 5 to 9 in SEQ ID Nos: 34, 36, 39 to 41, 47, 48, 50 and 53 to 57; amino acid numbers 4 to 8 in SEQ ID Nos: 35, 37, 38, 42 to 46, 49 and 52; and amino acid numbers 2 to 6 in SEQ ID Nos: 58 to 60.

Item 14:

The peptide according to item 6, wherein it is represented by the formula: A-B or B-C and, in the formula, B is a sequence selected from the group consisting of amino acid numbers 5 to 9 in SEQ ID Nos: 34, 36, 39 to 41, 47, 48, 50 and 53 to 57; amino acid numbers 4 to 8 in SEQ ID Nos: 35, 37, 38, 42 to 46, 49 and 52; and amino acid numbers 2 to 6 in SEQ ID Nos: 58 to 60, A is a sequence selected from the group consisting of a sequence comprising at least one amino acid continuing from the C terminal side of amino acid numbers 1 to 4 in SEQ ID Nos: 34, 36, 39 to 41, 47, 48, 50 and 53 to 57; a sequence comprising at least one amino acid continuing from the C terminal side of amino acid numbers 1 to 3 in SEQ ID Nos: 35, 37, 38, 42 to 46, 49 and 52; and an amino acid number 1 in SEQ ID Nos: 58 to 60 and C is a sequence selected from the group consisting of a sequence comprising at least one amino acid continuing from the N-terminal side of amino acid numbers 10 to 17 in SEQ ID Nos: 34, 36, 39 to 41, 47, 48, 50 and 53 to 54; a sequence comprising at least one amino acid continuing from the C-terminal side of amino acid numbers 9 to 16 in SEQ ID Nos: 35, 37, 38, 42 to 46, 49 and 52; a sequence comprising at least one amino acid continuing from the C-terminal side of amino acid numbers 10 to 16 in SEQ ID No: 57; and a sequence comprising at least one amino acid continuing from the C-terminal side of amino acid numbers 7 to 20 in SEQ ID No: 58.

Item 15:

The peptide according to item 14, wherein it is represented by the formula: A-B-C and, in the formula, A, B and C are the same as those in item 14.

Item 16:

The peptide according to item 6, wherein it is represented by the formula: B and, in the formula, B is a sequence selected from the group consisting of amino acid numbers 9 to 13 in SEQ ID Nos: 67 to 87; amino acid numbers 8 to 12 in SEQ ID No: 90; and amino acid numbers 15 to 19 in SEQ ID No: 91.

Item 17:

The peptide according to item 6, wherein it is represented by the formula: A-B or B-C and, in the formula, B is a sequence selected from the group consisting of amino acid numbers 9 to 13 in SEQ ID Nos: 67 to 87; amino acid numbers 8 to 12 in SEQ ID No: 90; and amino acid numbers 15 to 19 in SEQ ID No: 91, A is a sequence selected from the group consisting of a sequence comprising at least one amino acid continuing from C terminal side of amino acid numbers 1 to 8 in SEQ ID Nos: 67 to 87; a sequence comprising at least one amino acid continuing from C terminal side of amino acid numbers 1 to 7 in SEQ ID No: 90; and a sequence comprising at least one amino acid continuing from C terminal side of amino acid numbers 1 to 14 in SEQ ID No: 91 and C is a sequence selected from the group consisting of a sequence comprising at least one amino acid continuing from N terminal side of amino acid numbers 14 to 17 in SEQ ID Nos: 67, 68, 72 to 74, 80, 81, 83 and 86 to 87; a sequence comprising at least one amino acid continuing from N terminal side of amino acid numbers 14 to 16 in SEQ ID Nos: 68, 70, 71, 75 to 79, 82 and 85; a sequence comprising at least one amino acid continuing from N terminal side of amino acid numbers 13 to 16 in SEQ ID No: 90; and an amino acid number 20 in SEQ ID No: 91.

Item 18:

The peptide according to item 6, wherein it is represented by the formula: A-B-C and, in the formula, A, B and C are the same as those in item 17.

Item 19:

The peptide according to item 6, wherein it is represented by the formula: B and, in the formula, B is a sequence selected from the group consisting of amino acid numbers 5 to 9 in SEQ ID Nos: 34, 36, 39 to 41, 47, 48 and 50; and amino acid numbers 4 to 8 in SEQ ID Nos: 35, 37, 38, 42 to 46, 49 and 52.

Item 20:

The peptide according to item 6, wherein it is represented by the formula: A-B or B-C and, in the formula, B is a sequence selected from the group consisting of amino acid numbers 5 to 9 in SEQ ID Nos: 34, 36, 39 to 41, 47, 48 and 50; and amino acid numbers 4 to 8 in SEQ ID Nos: 35, 37, 38, 42 to 46, 49 and 52, A is a sequence selected from the group consisting of a sequence comprising at least one amino acid continuing from C terminal side of amino acid numbers 1 to 4 in SEQ ID Nos: 34, 36, 39 to 41, 47, 48 and 50; and a sequence comprising at least one amino acid continuing from C terminal side of amino acid numbers 1 to 3 in SEQ ID Nos: 35, 37, 38, 42 to 46, 49 and 52 and C is a sequence selected from the group consisting of a sequence comprising at least one amino acid continuing from N terminal side of amino acid numbers 10 to 17 in SEQ ID Nos: 34, 36, 39 to 41, 47, 48 and 50; and a sequence comprising at least one amino acid continuing from N terminal side of amino acid numbers 9 to 16 in SEQ ID Nos: 35, 37, 38, 42 to 46, 49 and 52.

Item 21:

The peptide according to item 6, where it is represented by the formula: A-B-C and, in the formula, A, B and C are the same as those in item 20.

Item 22:

The peptide according to item 6, where it is represented by the formula: B and, in the formula, B is a sequence selected from the group consisting of amino acid numbers 9 to 13 in SEQ ID Nos: 67 to 85.

Item 23:

The peptide according to item 6, where it is represented by the formula: A-B or B-C and, in the formula, B is a sequence selected from the group consisting of amino acid numbers 9 to 13 in SEQ ID Nos: 67 to 85, A is a sequence selected from the group consisting of a sequence comprising at least one amino acid continuing from C terminal side of amino acid numbers 1 to 8 in SEQ ID Nos: 67 to 85 and C is a sequence selected from the group consisting of a sequence comprising at least one amino acid continuing from N terminal side of amino acid numbers 14 to 17 in SEQ ID Nos: 67, 69, 72 to 74, 80, 81 and 83 and a sequence comprising at least one amino acid continuing from N terminal side of amino acid numbers 14 to 16 in SEQ ID Nos: 68, 70, 71, 75 to 79, 82 and 85.

Item 24:
The peptide according to item 6, wherein it is represented by the formula: A-B-C and, in the formula, A, B and C are the same as those in item 23.

Item 25:
The peptide according to item 6, wherein it is represented by the formula: B and, in the formula,
B is a sequence of amino acid numbers 5 to 9 in SEQ ID No: 34.

Item 26:
The peptide according to item 6, wherein it is represented by the formula: A-B or B-C and, in the formula,
B is a sequence of amino acid numbers 5 to 9 in SEQ ID No: 34,
A is a sequence comprising at least one amino acid continuing from C terminal side of amino acid numbers 1 to 4 in SEQ ID No: 34 and
C is a sequence comprising at least one amino acid continuing from N terminal side of amino acid numbers 10 to 17 in SEQ ID No: 34.

Item 27:
The peptide according to item 6, wherein it is represented by the formula: A-B-C and, in the formula, A, B and C are the same as those in item 26.

Item 28:
The peptide according to item 6, wherein it is represented by the formula: B and, in the formula,
B is a sequence of amino acid numbers 9 to 13 in SEQ ID No: 67.

Item 29:
The peptide according to item 6, wherein it is represented by the formula: A-B or B-C and, in the formula,
B is a sequence of amino acid numbers 9 to 13 in SEQ ID No: 67,
A is a sequence comprising at least one amino acid continuing from C terminal side of amino acid numbers 1 to 8 in SEQ ID No: 67 and
C is a sequence comprising at least one amino acid continuing from N terminal side of amino acid numbers 14 to 17 in SEQ ID No: 67.

Item 30:
The peptide according to item 6, wherein it is represented by the formula: A-B-C and, in the formula, A, B and C are the same as those in item 29.

Item 31:
A chimeric peptide where a peptide selected from the group consisting of the peptides mentioned in any of items 1 to 30 is bonded to N terminal, C terminal or both of the object peptide and its half-life in plasma is extended as compared with the object peptide while physiological activity of the object peptide is still retained.

Item 32:
The chimeric peptide according to item 31, wherein the peptide selected from the group consisting of the peptides mentioned in any of items 1 to 30 is bonded to N terminal of the object peptide.

Item 33:
The chimeric peptide according to item 31, wherein the peptide selected from the group consisting of the peptides mentioned in any of items 1 to 30 is bonded to C terminal of the object peptide.

Item 34:
The chimeric peptide according to item 31, wherein the peptide selected from the group consisting of the peptides mentioned in any of items 1 to 30 is bonded to both terminals of the object peptide.

Item 35:
The chimeric peptide according to any of items 31 to 34, wherein the object peptide is an atrial natriuretic peptide, a C type natriuretic peptide or motilin or derivatives thereof.

Item 36:
A pharmaceutical composition in which the chimeric peptide mentioned in any of items 31 to 35 or a pharmaceutically acceptable salt thereof is an effective ingredient.

Item 37:
The pharmaceutical composition according to item 36, wherein the chimeric peptide is the peptide mentioned in item 35.

Item 38:
The pharmaceutical composition according to item 37, wherein the object peptide in the chimeric peptide is an atrial natriuretic peptide or a derivative thereof.

Item 39:
The pharmaceutical composition according to item 38, wherein it is for the treatment of diseases selected from acute cardiac insufficiency, chronic cardiac insufficiency, obliterative arteriosclerosis, ischemic cardiac disease, hypertension, edema disease, myocardial disease, retinitis, diabetic renal disease, nephrosclerosis and myocardial infarction.

Item 40:
The pharmaceutical composition according to item 37, wherein the object peptide in the chimeric peptide is a C type natriuretic peptide or a derivative thereof.

Item 41:
The pharmaceutical composition according to item 40, wherein it is for the treatment of diseases selected from atypical chondrogenesis insufficiency, restenosis after PTCA after coronary artery stenosis, pulmonary hypertension, peripheral artery obliterative disease, osteoarthritis, rheumatoid arthritis, pulmonary fibrosis, hepatic fibrosis, renal fibrosis, myocardial infarction and myocarditis.

Item 42:
The pharmaceutical composition according to item 37, wherein the object peptide in the chimeric peptide is motilin or a derivative thereof.

Item 43:
The pharmaceutical composition according to item 42, wherein it is for the treatment of diseases selected from functional dyspepsia, reflux esophagitis, diabetic gastric motility paralysis, constipation-type irritable bowel syndrome, chronic peudoileus, postoperative ileus, chronic gastritis and atrophic gastritis.

Item 44:
A process for producing a chimeric peptide where half-life in plasma is extended as compared with the object peptide and a physiological activity of the object peptide is available, characterized in that, a peptide selected from the group consisting of the peptides mentioned in any of items 1 to 30 is bonded to N terminal, C terminal or both of the object peptide.

Item 45:
The process according to item 44, wherein a peptide selected from the group consisting of the peptides mentioned in any of items 1 to 30 is bonded to N terminal of the object peptide.

Item 46:
The process according to item 44, wherein a peptide selected from the group consisting of the peptides mentioned in any of items 1 to 30 is bonded to C terminal of the object peptide.

Item 47:
The process according to item 44, wherein a peptide selected from the group consisting of the peptides mentioned in any of items 1 to 30 is bonded to both terminals of the object peptide.

Item 48:
The process according to any of items 44 to 47, wherein the object peptide is a natriuretic peptide or motilin or derivatives thereof.

Item 49:
The process according to item 48, wherein the object peptide is an atrial natriuretic peptide or a derivative thereof.

Item 50:
The process according to item 48, wherein the object peptide is a C type natriuretic peptide or a derivative thereof.

Item 51:
The process according to item 48, wherein the object peptide is motilin or a derivative thereof.

Item 52:
A method for the treatment of a disease which is able to be treated by the object peptide contained in a pharmaceutical composition, comprising administration of the pharmaceutical composition selected from the pharmaceutical compositions mentioned in any of items 36 to 43 to an individual.

Item 53:
The method for the treatment according to item 52, wherein the pharmaceutical composition is the pharmaceutical composition mentioned in item 37.

Item 54:
The method for the treatment according to item 53, wherein the pharmaceutical composition is the pharmaceutical composition mentioned in item 38.

Item 55:
The method for the treatment according to item 54, wherein the disease is a disease selected from acute cardiac insufficiency, chronic cardiac insufficiency, obliterative arteriosclerosis, ischemic cardiac disease, hypertension, edema disease, myocardial disease, retinitis, diabetic renal disease, nephrosclerosis and myocardial infarction.

Item 56:
The method for the treatment according to item 53, wherein the pharmaceutical composition is the pharmaceutical composition mentioned in item 40.

Item 57:
The method for the treatment according to item 56, wherein the disease is a disease selected from atypical chondrogenesis insufficiency, restenosis after PTCA after coronary artery stenosis, pulmonary hypertension, peripheral artery obliterative disease, osteoarthritis, rheumatoid arthritis, pulmonary fibrosis, hepatic fibrosis, renal fibrosis, myocardial infarction and myocarditis.

Item 58:
The method for the treatment according to item 53, wherein the pharmaceutical composition is the pharmaceutical composition mentioned in item 42.

Item 59:
The method for the treatment according to item 58, wherein the disease is a disease selected from functional dyspepsia, reflux esophagitis, diabetic gastric motility paralysis, constipation-type irritable bowel syndrome, chronic peudoileus, postoperative ileus, chronic gastritis and atrophic gastritis.

Item 60:
A method for extension of half-life in plasma of the object peptide, characterized in that, the peptide selected from the peptides mentioned in any of items 1 to 30 is bonded to N terminal, C terminal or both of the object peptide.

Item 61:
The method according to item 60, wherein the peptide selected from the peptides mentioned in any of items 1 to 30 is bonded to N terminal of the object peptide.

Item 62:
The method according to item 60, wherein the peptide selected from the peptides mentioned in any of items 1 to 30 is bonded to C terminal of the object peptide.

Item 63:
The method according to item 60, wherein the peptide selected from the peptides mentioned in any of items 1 to 30 is bonded to both terminals of the object peptide.

Item 64:
The method according to any of items 60 to 63, wherein the object peptide is a natriuretic peptide or motilin or derivatives thereof.

Item 65:
The method according to item 64, wherein the object peptide is an atrial natriuretic peptide or a derivative thereof.

Item 66:
The method according to items 64, wherein the object peptide is a C type natriuretic peptide or a derivative thereof.

Item 67:
The process according to item 64, wherein the object peptide is motilin or a derivative thereof.

Advantageous Effects of Invention

When the peptide where half-life is extended according to the present invention is added to an object peptide having a short half-life, the pharmacokinetics in vivo are improved and a product having a half-life which is practical as a drug is achieved. Since its antigenic property is almost the same as those of the object peptide of a native, it has an excellent safety and shows resistance to enzymes which decompose a physiologically active peptide in vivo. When the peptide where the half-life is extended is used, it is now possible to greatly reduce the cost and time which have been necessary for the development of physiologically active peptides where the pharmacokinetics in vivo are improved. In addition, it is possible that an administering method for the physiologically active peptide used for the treatment by a continuous intravenous administration or a continuous subcutaneous administration is conducted in a single-time bolus administration whereby it is now expected to improve the compliance of the individual (patient) and of a medical field.

DESCRIPTION OF PREFERRED EMBODIMENTS

Figure 1:
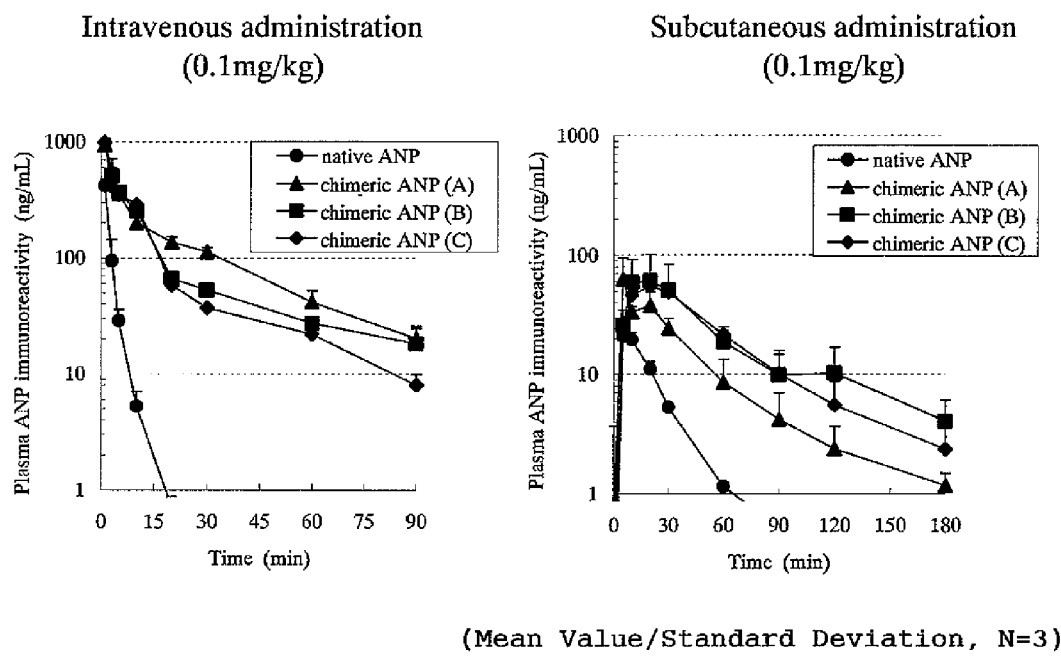
FIG. 1 This is a drawing which shows changes in an ANP immunoreactivity concentration in plasma when ANP or a chimeric ANP (A to C) thereof (0.1 mg/kg) is intravenously or subcutaneously administered to male rats.

The present invention will now be illustrated in detail as follows.

(1) Half-life-Extended Peptide

The half-life-extended peptide of the present invention is represented by B, A-B, B-C and A-B-C and, in the formulae, A, B and C are the following (1) to (3) and it is a peptide which is able to extent the half-life in plasma, when bonded to other object peptide (physiologically active peptide), as compared with the object peptide while the physiological activity of the object peptide is still retained.

(1) As shown by the amino acid sequence (14 amino acids: Table 5) in 1 to 14 positions in C terminal fragment (SEQ ID No: 91) derived from frog ghrelin, chimeric motilin (A to F and G to K) (they are in Table 14), MG-d12/14 (Table 16), chimeric CNP (J) and chimeric CNP (K) (Table 17), A may be absent or a sequence of amino acid in any number may be present. As to the length when the sequence is present, a sequence of about 1 to 14 amino acid(s) may be selected and it is preferably 3 to 10 amino acids and, more preferably, 3 amino acids. Specific examples include VQQ and AGSVDH-KGKQ (SEQ ID NO: 161).

(2) B is a part which corresponds to the structure (core sequence: RKESKK sequence part (SEQ ID NO: 162)) necessary for an action for extending the half-life of the peptide of the present invention derived from human ghrelin which will be mentioned later and examples for B of the peptide of the present invention derived from human ghrelin include the followings. The specific peptides mentioned below are described in Tables 16 and 17.

As chimeric motilin (T) (MG-17E/N), (U) (MG-17E/Q) and (W) (MG-dES) show, the E(Glu) in RKESKK (SEQ ID NO: 162) is an essential amino acid. Further, as chimeric motilin (V) (MG-ES/DS), (X) (MG-17E/D), chimeric CNP (J) and chimeric CNP (K) show, it may be D(Asp) as well. Thus, acidic amino acid will do for the amino acid at the position of the above E(Glu) and Glu is preferred.

As chimeric motilin (0) (MG-18S/F), (P) (MG-18S/T), (Q) (MG-18S/P), (R) (MG-18S/L) and (S) (MG-18S/A) show, the S(Ser) in RKESKK (SEQ ID NO: 162) is able to be substituted with amino acid having any side chain such as aromatic amino acid, hydrophobic amino acid and polar non-charged amino acid. Thus, the amino acid at the above position of S(Ser) may be an amino acid having any side chain structure. It is preferably Ser, Pro, Leu, Phe or Ala, more preferably Ser, Thr, Pro or Ala and, most preferably, Ser. Further, as shown the peptide MG-dS, the amino acid at the position or the above S (Ser) may be absent.

As shown by chimeric motilin (X) (MG-17E/D), R (Arg) and K (Lys) in RKESKK (SEQ ID NO: 162) are able to be substituted provided that it is a basic amino acid.

RKESKK (SEQ ID NO: 162) is characterized in containing a basic amino acid cluster (a continuous sequence of two basic amino acids) and an acidic amino acid and, as shown in chimeric motilin (Z) (MG-i17G), (I) (MG-i19G), (II) (MG-i17G2) and (III) (MG-i17G2-i19G), the distance between the clusters is able to be expanded by insertion of any amino acid.

Further, any amino acid may be present between the basic amino acid cluster and E (Glu) in RKESKK (SEQ ID NO: 162) as shown in chimeric motilin (Z) (MG-i17G), (I) (MG-i19G), (II) (MG-i17G2), (III) (MG-i17G2-19iG), (IV) (MG-dPP), (V) (MG-dPPH1), (VI) (MG-H1), (VII) (MG-H3), (VIII) (MGH4), (XI) (MG-d12114), (XII) (MGP1), (XIII) (MGP)$_2$ etc. and chimeric CNP (K). For example, G, A, Y, SP and/or V may be made to exit between the basic amino acid cluster (RK-corresponding part) and E and, between E and the basic amino acid cluster (KK-corresponding part), S, H and/or P may be made to exist.

In view of the above, the structure B (core sequence: RKESKK (SEQ ID NO: 162) part for human) necessary for an action of half-life-extension concerning the invention of the present application has, firstly, a sequence represented by the following formula 2.

Wk-Xl-Y-Zm-Wn        Formula 2:

In the formula, W is a basic amino acid; X and Z each is any amino acid; and Y is an acidic amino acid. Each k, l, m and n is 0 or a natural number, k is 1 or 2, 4≥l≥0, 2≥m≥0 (where l and m are 4≥l+m≥0) and n is 1 or 2.

As shown in chimeric motilin (Y) (MG-BR), the way of alignment of RKESKK SEQ ID NO: 162) may be reversed (KKSEKR) (SEQ ID NO: 163).

Further, as shown in chimeric motilin (XII) (MGP1) and (XIII) (MGP2), since a half-life-extension action is potentiated when the core sequence is aligned in two tandems (such as KKAYSPK (SEQ ID NO: 164)+ERK), it is also an effective means in achieving longer half-life extension that plural core sequences are available in a molecule as shown by the following formula.

Accordingly, the structure (core sequence: RKESKK part (SEQ ID NO: 162)) necessary for the half-life-extension action concerning the invention of the present application is expressed by the following formula 1:

$$(W_k\text{-}X_l\text{-}Y\text{-}Z_m\text{-}W_n)+(W_o\text{-}X_p\text{-}Y\text{-}Z_q\text{-}W_r)_s \quad \text{Formula 1:}$$

In the formula, W, X, Y, Z, K, l, m and n are the same as those in the above formula 2 and s is 0 or 1. Further, o, p, q and r each is 0 or a natural number, $2 \geq o \geq 0$, $4 \geq p \geq 0$, $2 \geq q \geq 0$ (where p and q are $4 \geq p+q \geq 0$) and r is 1 or 2.

The acidic amino acid is E(Glu) or D(Asp) and, preferably, E(Glu). With regard to X and Z which are any amino acids, X and Z may be same or different and, when there are plural ones, each of them may be same or different. Preferably, X and Z each is Ser, Pro, Leu, Phe or Ala, more preferably Ser, Thr, Pro or Ala and, most preferably, Ser. With regard to the basic amino acid W, both W may be same or different and, when there are plural ones, each, of them may be same or different. W is preferably R(Arg) or K(Lys).

Preferably, in the formula 1, s is 1; o, p and q each is 0; and r is 2.

C is able to select any sequence of amino acid numbers such as about 2 to 14 amino acids as shown in the amino acid sequence (two amino acids: Table 14) at 22 to 23 positions in chimeric motilin (J), the amino acid sequence (14 amino acids: Table 5) at 7 to 20 positions in C terminal fragment (SEQ ID No: 58) derived from frog ghrelin and the chimeric motilin (VI) (MG-H 1), (VII) (MG-H3) and (VIII) (MG-H4) aligned with a sequence (such as AK (or E) LAALK (or E) A) (SEQ ID NO: 165) predicted to form an α-helix structure by a known method for predicting the secondary structure (such as Chou-Fasman method: Biochemistry. 1974 Jan. 15; 13(2): 222-45 Prediction of protein conformation. Chou P Y, Fasman G D; or Garnier method: J Mol Biol. 1978 Mar. 25; 120(1):97-120. Analysis of the accuracy and implications of simple methods for predicting the secondary structure of globular proteins. Gamier J, Osguthorpe D J, Robseon B. etc.).

It is preferred to be any sequence comprising 3 to 11 amino acids being able to form an α helix structure, more preferably KKPPAKLQPR (SEQ ID NO: 166) (a sequence comprising amino acids at 22nd to 29th positions from N terminal in chimeric motilin (C)) or PPAELAALEA (SEQ ID NO: 167) (a sequence comprising amino acids at 22nd to 31st positions from N terminal in chimeric motilin (VII) (MG-H3)) and, still more preferably, PPAELAALEA (SEQ ID NO: 167). It is also possible to use any sequence which is able to form a sheet structure by the above prediction method.

Further, when no Pro is present between the amino acid sequence corresponding to the formula C of the half-life-extension peptide according to the invention of the present invention and the amino acid sequence corresponding to the formula B thereof, it is preferred that Pro sequence (Pro numbers within a range by which amino acid numbers of C become 2 to 14 or, preferably, Pro-Pro) is aligned at the terminal site of the amino acid sequence corresponding to the formula C as shown by a comparison of chimeric motilin (IV) (MG-dPP) with chimeric motilin (D), a comparison of chimeric motilin (V) (MG-dPPH1) with chimeric motilin (VI) (MG-H1) and a comparison of chimeric motilin (IX) (MG-dPPS) with chimeric motilin (X) (MG-S).

Further, since a chimeric CNP containing a sequence corresponding to B (core sequence) of the formula of the half-life-extension peptide concerning the invention of the present application also shows a half-life-extension action as shown in the chimeric CNP (J) and (K), it is easily able to be predicted by persons skilled in the art that the same half-life-extension action is able to be achieved when the requirements for A and C of the formula of the half-life-extension peptide concerning the invention of the present application introduced from the comparison in half-lives of chimeric motilin is applied to the chimeric CNP. It is also able to be easily predicted by persons skilled in the art that the same half-life-extension action is able to be achieved when the requirements for B and C of the formula of the half-life-extension peptide concerning the invention of the present application introduced from the comparison in half-lives of chimeric CNP is applied to the chimeric motilin.

Further, it is also able to be easily predicted by persons skilled in the art that the same half-life-extension action is able to be achieved when the requirements for A, B and C of the formula of the half-life-extension peptide concerning the invention of the present application is applied to the chimeric peptide of other object peptides.

A, B and/or C each may be in the normal direction or the reversed direction. Thus, A, B and C each independently may be in a normal direction or a reversed direction or A-B, B-C and A-B-C may be in the normal direction or the reversed direction as a whole. The normal direction and the reversed order used here mean that the sequence direction from N terminal and C terminal is reversed each other.

When the peptide of the present invention is a sole B, it includes the case where a sequence satisfying the requirements of A and/or C is present in the object peptide side.

In the half-life-extension peptide of the present invention, the preferred one is a peptide of the following (1) or (2).

(1) A is an amino acid sequence of one or more amino acid numbers 1 to 4 continuing to B in SEQ ID No: 34 or an amino acid sequence where one or some amino acid(s) in the above amino acid sequence is/are deleted, substituted and/or added;

B is an amino acid sequence of one or more amino acid numbers 5 to 9 in SEQ ID No: 34 or an amino acid sequence where one or some amino acid(s) in the above amino acid sequence is/are deleted, substituted and/or added; and C is an amino acid sequence of one or more amino acid numbers 10 to 17 continuing to B in SEQ ID No: 34 or an amino acid sequence where one or some amino acid(s) in the above amino acid sequence is/are deleted, substituted and/or added.

(2) A is an amino acid sequence of one or more amino acid numbers 1 to 8 continuing to B in SEQ ID No: 67 or an amino acid sequence where one or some amino acid(s) in the above amino acid sequence is/are deleted, substituted and/or added;

B is an amino acid sequence of amino acid numbers 9 to 13 in SEQ ID No: 67 or an amino acid sequence where one or some amino acid(s) in the above amino acid sequence is/are deleted, substituted and/or added; and C is an amino acid sequence of one or more amino acid numbers 14 to 17 continuing to B in SEQ ID No: 67 or an amino acid sequence where one or some amino acid(s) in the above amino acid sequence is/are deleted, substituted and/or added.

SEQ ID No: 67 is a reversed sequence of SEQ ID No: 34.

B is an essential core sequence.

In other words, the half—life-extension peptide according to the present invention is a peptide containing the amino acid sequence of amino acid numbers 5 to 9 in SEQ ID No: 34 or amino acid sequence of amino acid numbers 9 to 13 in SEQ ID No: 67 which is a reversed sequence of the above and comprising 17 or less amino acids or a peptide in which one or some amino acid(s) is/are deleted, substituted and/or added in the amino acid sequence. The term "one or some" used hereinabove means 1 to 35 for example, preferably 1 to 15, more preferably 1 to 10, still more preferably 1 to 8, still more preferably 1 to 6, still more preferably 1 to 5, still more preferably 1 to 4, still more preferably 1 to 3 and, still more preferably, 1 to 2.

The half-life-extension peptide of the present invention includes a half-life-extension peptide comprising a C terminal partial sequence of ghrelin of mammals such as human, monkey, cattle, horse, swine, dog, deer, sheep, goat, cat, rabbit, rat, Suncus (musk rat) or whale, birds such as turkey or domestic fowl, reptiles such as turtle, amphibians such as frog and fish such as eel, catfish or shark.

As to deletion, substitution and/or addition of one or some amino acid(s) in the amino acid sequence of A, B and C each of SEQ ID No: 34 or SEQ ID No: 67, persons skilled in the art are able to appropriately select the position and type of the suitable amino acid for conducting the modification as such by comparison among the amino acid sequences derived from various species.

Amino acid sequence of ghrelin derived from various organisms, half-life extending peptide of C terminal part thereof, full length of core sequence B, full length of sequence A which may be present in the N terminal side of the core sequence and full length of sequence C which may be present in the C terminal side of the core sequence are shown in the following Tables 1 to 7.

TABLE 1

| Species | Sequence No. of Ghrelin | Amino Acid No. of each Part of Sequence No. (Normal Direction) of Half-life-extension Peptide | Amino Acid No. of each Part of Sequence No. (Reversed Direction) of Half-life-extension Peptide |
|---|---|---|---|
| Human | SEQ ID No: 1 | SEQ ID No: 34<br>A: 1 to 4<br>B: 5 to 9<br>C: 10 to 17 | SEQ ID No: 67<br>A: 1 to 8<br>B: 9 to 13<br>C: 14 to 17 |
|  | SEQ ID No: 2 | SEQ ID No: 35<br>A: 1 to 3<br>B: 4 to 8<br>C: 9 to 16 | SEQ ID No: 68<br>A: 1 to 8<br>B: 9 to 13<br>C: 14 to 16 |
| Monkey | SEQ ID No: 3 | SEQ ID No: 36<br>A: 1 to 4<br>B: 5 to 9<br>C: 10 to 17 | SEQ ID No: 69<br>A: 1 to 8<br>B: 9 to 13<br>C: 14 to 17 |
| Cattle | SEQ ID No: 4 | SEQ ID No: 37<br>A: 1 to 3<br>B: 4 to 8<br>C: 9 to 16 | SEQ ID No: 70<br>A: 1 to 8<br>B: 9 to 13<br>C: 14 to 16 |
|  | SEQ ID No: 5 | SEQ ID No: 38<br>A: 1 to 3<br>B: 4 to 8<br>C: 9 to 16 | SEQ ID No: 71<br>A: 1 to 8<br>B: 9 to 13<br>C: 14 to 16 |
| Horse | SEQ ID No: 6 | SEQ ID No: 39<br>A: 1 to 4<br>B: 5 to 9<br>C: 10 to 17 | SEQ ID No: 72<br>A: 1 to 8<br>B: 9 to 13<br>C: 14 to 17 |
| Swine | SEQ ID No: 7 | SEQ ID No: 40<br>A: 1 to 4<br>B: 5 to 9<br>C: 10 to 17 | SEQ ID No: 73<br>A: 1 to 8<br>B: 9 to 13<br>C: 14 to 17 |

TABLE 2

| Species | Sequence No. of Ghrelin | Amino Acid No. of each Part of Sequence No. (Normal Direction) of Half-life-extension Peptide | Amino Acid No. of each Part of Sequence No. (Reversed Direction) of Half-life-extension Peptide |
|---|---|---|---|
| Dog | SEQ ID No: 8 | SEQ ID No: 41<br>A: 1 to 4<br>B: 5 to 9<br>C: 10 to 17 | SEQ ID No: 74<br>A: 1 to 8<br>B: 9 to 13<br>C: 14 to 17 |
| Deer | SEQ ID No: 9 | SEQ ID No: 42<br>A: 1 to 3<br>B: 4 to 8<br>C: 9 to 16 | SEQ ID No: 75<br>A: 1 to 8<br>B: 9 to 13<br>C: 14 to 16 |
|  | SEQ ID No: 10 | SEQ ID No: 43<br>A: 1 to 3<br>B: 4 to 8<br>C: 9 to 16 | SEQ ID No: 76<br>A: 1 to 8<br>B: 9 to 13<br>C: 14 to 16 |
| Sheep | SEQ ID No: 11 | SEQ ID No: 44<br>A: 1 to 3<br>B: 4 to 8<br>C: 9 to 16 | SEQ ID No: 77<br>A: 1 to 8<br>B: 9 to 13<br>C: 14 to 16 |
| Goat | SEQ ID No: 12 | SEQ ID No: 45<br>A: 1 to 3<br>B: 4 to 8<br>C: 9 to 16 | SEQ ID No: 78<br>A: 1 to 8<br>B: 9 to 13<br>C: 14 to 16 |
| Cat | SEQ ID No: 13 | SEQ ID No: 46<br>A: 1 to 3<br>B: 4 to 8<br>C: 9 to 16 | SEQ ID No: 79<br>A: 1 to 8<br>B: 9 to 13<br>C: 14 to 16 |
| Rabbit | SEQ ID No: 14 | SEQ ID No: 47<br>A: 1 to 4<br>B: 5 to 9<br>C: 10 to 17 | SEQ ID No: 80<br>A: 1 to 8<br>B: 9 to 13<br>C: 14 to 17 |

TABLE 3

| Species | Sequence No. of Ghrelin | Amino Acid No. of each Part of Sequence No. (Normal Direction) of Half-life-extension Peptide | Amino Acid No. of each Part of Sequence No. (Reversed Direction) of Half-life-extension Peptide |
|---|---|---|---|
| Rat | SEQ ID No: 15 | SEQ ID No: 48<br>A: 1 to 4<br>B: 5 to 9<br>C: 10 to 17 | SEQ ID No: 81<br>A: 1 to 8<br>B: 9 to 13<br>C: 14 to 17 |
|  | SEQ ID No: 16 | SEQ ID No: 49<br>A: 1 to 3<br>B: 4 to 8<br>C: 9 to 16 | SEQ ID No: 82<br>A: 1 to 8<br>B: 9 to 13<br>C: 14 to 16 |
|  | SEQ ID No: 17 | SEQ ID No: 50<br>A: 1 to 4<br>B: 5 to 9<br>C: 10 to 17 | SEQ ID No: 83<br>A: 1 to 8<br>B: 9 to 13<br>C: 14 to 17 |
| Suncus | SEQ ID No: 18 | SEQ ID No: 51<br>A: 1 to 2<br>B: 3 to 8<br>C: 9 to 15 | SEQ ID No: 84<br>A: 1 to 7<br>B: 8 to 13<br>C: 14 to 15 |
| Whale | SEQ ID No: 19 | SEQ ID No: 52<br>A: 1 to 3<br>B: 4 to 8<br>C: 9 to 16 | SEQ ID No: 85<br>A: 1 to 8<br>B: 9 to 13<br>C: 14 to 16 |
| Turkey | SEQ ID No: 20 | SEQ ID No: 53<br>A: 1 to 4<br>B: 5 to 9<br>C: 10 to 17 | SEQ ID No: 86<br>A: 1 to 8<br>B: 9 to 13<br>C: 14 to 17 |

TABLE 4

| Species | Sequence No. of Ghrelin | Amino Acid No. of each Part of Sequence No. (Normal Direction) of Half-life-extension Peptide | Amino Acid No. of each Part of Sequence No. (Reversed Direction) of Half-life-extension Peptide |
|---|---|---|---|
| Domestic Fowl | SEQ ID No: 21 | SEQ ID No: 54<br>A: 1 to 4<br>B: 5 to 9<br>C: 10 to 17 | SEQ ID No: 87<br>A: 1 to 8<br>B: 9 to 13<br>C: 14 to 17 |
|  | SEQ ID No: 22 | SEQ ID No: 55<br>A: 1 to 4<br>B: 5 to 9<br>C: 10 to 15 | SEQ ID No: 88<br>A: 1 to 6<br>B: 7 to 11<br>C: 12 to 15 |
|  | SEQ ID No: 23 | SEQ ID No: 56<br>A: 1 to 4<br>B: 5 to 9<br>C: 10 to 13 | SEQ ID No: 89<br>A: 1 to 4<br>B: 5 to 9<br>C: 10 to 13 |
| Turtle | SEQ ID No: 24 | SEQ ID No: 57<br>A: 1 to 4<br>B: 5 to 9<br>C: 10 to 16 | SEQ ID No: 90<br>A: 1 to 7<br>B: 8 to 12<br>C: 13 to 16 |

TABLE 5

| Species | Sequence No. of Ghrelin | Amino Acid No. of each Part of Sequence No. (Normal Direction) of Half-life-extension Peptide | Amino Acid No. of each Part of Sequence No. (Reversed Direction) of Half-life-extension Peptide |
|---|---|---|---|
| Frog | SEQ ID No: 25 | SEQ ID No: 58<br>A: 1<br>B: 2 to 6<br>C: 7 to 20 | SEQ ID No: 91<br>A: 1 to 14<br>B: 15 to 19<br>C: 20 |
|  | SEQ ID No: 26 | SEQ ID No: 59<br>A: 1<br>B: 2 to 6<br>C: 7 to 18 | SEQ ID No: 92<br>A: 1 to 12<br>B: 13 to 17<br>C: 18 |
|  | SEQ ID No: 27 | SEQ ID No: 60<br>A: 1<br>B: 2 to 6<br>C: 7 to 17 | SEQ ID No: 93<br>A: 1 to 11<br>B: 12 to 16<br>C: 17 |

TABLE 6

| Species | Sequence No. of Ghrelin | Amino Acid No. of each Part of Sequence No. (Normal Direction) of Half-life-extension Peptide | Amino Acid No. of each Part of Sequence No. (Reversed Direction) of Half-life-extension Peptide |
|---|---|---|---|
| Eel | SEQ ID No: 28 | SEQ ID No: 61<br>A: 1 to 2<br>B: 3 to 6<br>C: 7 to 13 | SEQ ID No: 94<br>A: 1 to 7<br>B: 8 to 11<br>C: 12 to 13 |
|  | SEQ ID No: 29 | SEQ ID No: 62<br>A: 1 to 2<br>B: 3 to 6<br>C: 7 to 10 | SEQ ID No: 95<br>A: 1 to 4<br>B: 5 to 8<br>C: 9 to 10 |

TABLE 7

| Species | Sequence No. of Ghrelin | Amino Acid No. of each Part of Sequence No. (Normal Direction) of Half-life-extension Peptide | Amino Acid No. of each Part of Sequence No. (Reversed Direction) of Half-life-extension Peptide |
|---|---|---|---|
| Catfish | SEQ ID No: 30 | SEQ ID No: 63<br>A: 1 to 2<br>B: 3 to 7<br>C: 8 to 14 | SEQ ID No: 96<br>A: 1 to 7<br>B: 8 to 12<br>C: 13 to 14 |
|  | SEQ ID No: 31 | SEQ ID No: 64<br>A: 1 to 2<br>B: 3 to 7<br>C: 8 to 12 | SEQ ID No: 97<br>A: 1 to 5<br>B: 6 to 10<br>C: 11 to 12 |
|  | SEQ ID No: 32 | SEQ ID No: 65<br>A: 1 to 2<br>B: 3 to 7<br>C: 8 to 11 | SEQ ID No: 98<br>A: 1 to 4<br>B: 5 to 9<br>C: 10 to 11 |
| Shark | SEQ ID No: 33 | SEQ ID No: 66<br>A: nil<br>B: 1 to 3<br>C: 4 to 18 | SEQ ID No: 99<br>A: 1 to 15<br>B: 16 to 18<br>C: nil |

Amino acid sequences of ghrelin derived from various organisms in Tables 1 to 7 are shown as hereunder. The underlined ones are the parts corresponding to the half-life extending peptide.

```
Human      GSSFLSPEHQRVQQRKESKKPPAKLQPR    (SEQ ID No: 1)
           GSSFLSPEHQRVQ-RKESKKPPAKLQPR    (SEQ ID No: 2)

Monkey     GSSFLSPEHQRAQQRKESKKPPAKLQPR    (SEQ ID No: 3)

Cattle     GSSFLSPEHQKLQ-RKEAKKPSGRLKPR    (SEQ ID No: 4)
           GSSFLSPEHQKLQ-RKEPKKPSGRLKPR    (SEQ ID No: 5)

Horse      GSSFLSPEHHKVQHRKESKKPPAKLKPR    (SEQ ID No: 6)

Swine      GSSFLSPEHQKVQQRKESKKPAAKLKPR    (SEQ ID No: 7)

Dog        GSSFLSPEHQKLQQRKESKKPPAKLQPR    (SEQ ID No: 8)

Deer       GSSFLSPEHQKLQ-RKEPKKPSGRLKPR    (SEQ ID No: 9)
           GSSFLSPDHQKLQ-RKEPKKPSGRLKPR    (SEQ ID No: 10)

Sheep      GSSFLSPEHQKLQ-RKEPKKPSGRLKPR    (SEQ ID No: 11)

Gout       GSSFLSPEHQKLQ-RKEPKKPSGRLKPR    (SEQ ID No: 12)

Cat        GSSFLSPEHQKVQ-RKESKKPPAKLQPR    (SEQ ID No: 13)

Rabbit     GSSFLSPEHQKVQQRKESKKPAAKLKPR    (SEQ ID No: 14)

Rat        GSSFLSPEHQKAQQRKESKKPPAKLQPR    (SEQ ID No: 15)
           GSSFLSPEHQKAQ-RKESKKPPAKLQPR    (SEQ ID No: 16)
           GSSFLSPEHQKTQQRKESKKPPAKLQPR    (SEQ ID No: 17)
```

-continued

```
Suncus      GSSFLSPEHQKGP-KKDPRKPPKLQPR    (SEQ ID No: 18)

Whale       GSSFLSPEHQKLQ-RKEAKKPSGRLKPR   (SEQ ID No: 19)

Turkey      GSSFLSPAYKNIQQQKDTRKPTARLHPR   (SEQ ID No: 20)

Dom. Fowl   GSSFLSPTYKNIQQQKDTRKPTARLHRR   (SEQ ID No: 21)
            GSSFLSPTYKNIQQQKDTRKPTARLH     (SEQ ID No: 22)
            GSSFLSPTYKNIQQQKDTRKPTAR       (SEQ ID No: 23)

Turtle      GSSFLSPEYQNTQQRKDPKKHTK-LNRR   (SEQ ID No: 24)

Frog        GLTFLSPADMQKIAERQSQNKLRHGNMNRR (SEQ ID No: 25)
            GLTFLSPADMQKIAERQSQNKLRHGNMN   (SEQ ID No: 26)
            GLTFLSPADMQKIAERQSQNKLRHGNM    (SEQ ID No: 27)

Eel         GSSFLSPS-QRPQG-KD-KKP-PRVGRR   (SEQ ID No: 28)
            GSSFLSPS-QRPQG-KD-KKP-PRV-NH₂  (SEQ ID No: 29)

Catfish     GSSFLSPT-QKPQNR-GDRKPP-RVGRR   (SEQ ID No: 30)
            GSSFLSPT-QKPQNR-GDRKPP-RVG     (SEQ ID No: 31)
            GSSFLSPT-QKPQNR-GDRKPP-RV-NH₂  (SEQ ID No: 32)

Shark       GVSFHPRLKEKDDNSSGNSRKSNPKR     (SEQ ID No: 33)
```

Amino acid sequences of the half-life-extension peptide (normal sequences) derived from various organisms in Tables 1 to 7 are shown as hereunder. The underlined ones are the parts corresponding to the core sequence B, the N terminal side of the core sequence B is the part corresponding to the sequence A and the C terminal side of the core sequence B is the part corresponding to the sequence C.

```
Human       VQQRKESKKPPAKLQPR        (SEQ ID No: 34)
            VQ-RKESKKPPAKLQPR        (SEQ ID No: 35)

Monkey      AQQRKESKKPPAKLQPR        (SEQ ID No: 36)

Cattle      LQ-RKEAKKPSGRLKPR        (SEQ ID No: 37)
            LQ-RKEPKKPSGRLKPR        (SEQ ID No: 38)

Horse       VQHRKESKKPPAKLQPR        (SEQ ID No: 39)

Swine       VQQRKESKKPAAKLKPR        (SEQ ID No: 40)

Dog         LQQRKESKKPPAKLQPR        (SEQ ID No: 41)

Deer        LQ-RKEPKKPSGRLKPR        (SEQ ID No: 42)
            LQ-RKEPKKPSGRLKPR        (SEQ ID No: 43)

Sheep       LQ-RKEPKKPSGRLKPR        (SEQ ID No: 44)

Goat        LQ-RKEPKKPSGRLKPR        (SEQ ID No: 45)

Cat         VQ-RKESKKPPAKLQPR        (SEQ ID No: 46)

Rabbit      VQQRKESKKPAAKLKPR        (SEQ ID No: 47)

Rat         AQQRKESKKPPAKLQPR        (SEQ ID No: 48)
            AQ-RKESKKPPAKLQPR        (SEQ ID No: 49)
            TQQRKESKKPPAKLQPR        (SEQ ID No: 50)

Suncus      GP-KKDPRKPPKLQPR         (SEQ ID No: 51)

Whale       LQ-RKEAKKPSGRLKPR        (SEQ ID No: 52)

Turkey      IQQQKDTRKPTARLHPR        (SEQ ID No: 53)

Dom. Fowl   IQQQKDTRKPTARLHRR        (SEQ ID No: 54)
            IQQQKDTRKPTARLH          (SEQ ID No: 55)
            IQQQKDTRKPTAR            (SEQ ID No: 56)

Turtle      TQQRKDPKKHTK-LNRR        (SEQ ID No: 57)

Frog        QKIAERQSQNKLRHGNMNRR     (SEQ ID No: 58)
            QKIAERQSQNKLRHGNMN       (SEQ ID No: 59)
            QKIAERQSQNKLRHGNM        (SEQ ID No: 60)

Eel         QK-KD-KKP-PRVGRR         (SEQ ID No: 61)
            QK-KD-KKP-PRV            (SEQ ID No: 62)

Catfish     QNR-GDRKPP-RVGRR         (SEQ ID No: 63)
            QNR-GDRKPP-RVG           (SEQ ID No: 64)
            QNR-GDRKPP-RV            (SEQ ID No: 65)

Shark       KEKDDNSSGNSRKSNPKR       (SEQ ID No: 66)
```

Amino acid sequences of the half-life-extension peptide (reversed sequences) derived from various organisms in Tables 1 to 7 are shown as hereunder. The underlined ones are the parts corresponding to the core sequence B, the N terminal side of the core sequence B is the part corresponding to the sequence A and the C terminal side of the core sequence B is the part corresponding to the sequence C.

```
Human       RPQLKAPPKKSEKRQQV        (SEQ ID No: 67)
            RPQLKAPPKKSEKR-QV        (SEQ ID No: 68)

Monkey      RPQLKAPPKKSEKRQQA        (SEQ ID No: 69)

Cattle      RPKLRGSPKKAEKR-QL        (SEQ ID No: 70)
            RPKLRGSPKKPEKR-QL        (SEQ ID No: 71)

Horse       RPKLKAPPKKSEKRHQV        (SEQ ID No: 72)

Swine       RPKLKAAPKKSEKRQQV        (SEQ ID No: 73)

Dog         RPQLKAPPKKSEKRQQL        (SEQ ID No: 74)

Deer        RPKLRGSPKKPEKR-QL        (SEQ ID No: 75)
            RPKLRGSPKKPEKR-QL        (SEQ ID No: 76)

Sheep       RPKLRGSPKKPEKR-QL        (SEQ ID No: 77)

Goat        RPKLRGSPKKPEKR-QL        (SEQ ID No: 78)

Cat         RPQLKAPPKKSEKR-QV        (SEQ ID No: 79)

Rabbit      RPKLKAAPKKSEKRQQV        (SEQ ID No: 80)

Rat         RPQLKAPPKKSEKRQQA        (SEQ ID No: 81)
            RPQLKAPPKKSEKR-QA        (SEQ ID No: 82)
            RPQLKAPPKKSEKRQQT        (SEQ ID No: 83)
```

-continued

| Suncus | RPQLKPP<u>KRPDKK</u>-PG | (SEQ ID No: 84) |
|---|---|---|
| Whale | RPKLRGSP<u>KKAEKR</u>-QL | (SEQ ID No: 85) |
| Turkey | RPHLRATP<u>KRTDK</u>QQQI | (SEQ ID No: 86) |
| Dom. Fowl | RRHLRATP<u>KRTDK</u>QQQI | (SEQ ID No: 87) |
|  | HLRATP<u>KRTDK</u>QQQI | (SEQ ID No: 88) |
|  | RATP<u>KRTDK</u>QQQI | (SEQ ID No: 89) |
| Turtle | RRNL-KTH<u>KKPDKR</u>QQT | (SEQ ID No: 90) |
| Frog | RRNMNGHRLKNQSQ<u>REAIKQ</u> | (SEQ ID No: 91) |
|  | NMNGHRLKNQSQ<u>REAIKQ</u> | (SEQ ID No: 92) |
|  | MNGHRLKNQSQ<u>REAIKQ</u> | (SEQ ID No: 93) |
| Eel | RRGVRP-P<u>KK-DK</u>-GQ | (SEQ ID No: 94) |
|  | VRP-P<u>KK-DK</u>-GQ | (SEQ ID No: 95) |
| Catfish | RRGVR-PP<u>KRDG-RNQ</u> | (SEQ ID No: 96) |
|  | GVR-PP<u>KRDG-RNQ</u> | (SEQ ID No: 97) |
|  | VR-PP<u>KRDG-RNQ</u> | (SEQ ID No: 98) |
| Shark | RKPNSKRSNGSSNDD<u>KEK</u> | (SEQ ID No: 99) |

The half-life-extension peptide as such is preferred to be used for the individual of the species wherefrom the peptide is derived. For human for example, it is preferred to use the C terminal sequence of ghrelin derived from human. When the half-life-extension peptide comprises the sequence of AB, BC or ABC, it is preferred to use the sequence A, B and C derived from the same organism species although it is also possible to use a chimera peptide in which the sequences A, B and C are derived from different species. In the chimera peptide, combination of sequences derived from mammals, birds, reptiles and amphibians is preferred, combination of sequences derived from mammals is more preferred and combination of sequences derived from human is still more preferred.

In the present invention, the expression reading that, when bonded to an object peptide, its physiological activity is retained means that, when bonded to any of N terminal, C terminal or both terminals of the object peptide, not less than 1% of the activity of the object peptide is still retained. The expression reading that the half-life of the object peptide is extended means that, when bonded to any of N terminal, C terminal or both terminals of the object peptide, the resulting half-life is extended as compared with the object peptide even a little.

(2) Chimeric Peptide

When the above-illustrated half-life-extension peptide of the present invention is bonded to N terminal side, C terminal side or both terminal sides of the peptide having a physiological activity, the chimeric peptide of the present invention having an improved pharmacokinetics in viva is prepared. When the half-life-extension peptide is bonded to both terminals, the both peptides may be same or different.

A and/or C may be bonded to N terminal and/or C terminal of the object peptide. Alternatively, addition of A and/or C to side chain of the amino acid contained in B such as amino group of lysine resin, carboxyl group of glutamic acid or aspartic acid, etc. is also an embodiment of the present invention. As to the embodiment for the addition, it is also possible to select a peptide bond or other appropriate bonding method if desired.

As to the object peptide, it is possible to use a derivative which is a peptide having an amino acid sequence where one or some amino acid(s) is/are deleted, substituted and/or added in the amino acid sequence concerning the natural physiologically active peptide or the peptide and having the physiological activity of the peptide. Unless otherwise specifically mentioned in the present specification, there is no particular limitation for the numbers of amino acid(s) which is/are substituted, etc. in "one or more is/are substituted, deleted, inserted and/or added" concerning the amino acid provided that the peptide comprising the amino acid sequence or a derivative thereof has a desired function and, for example, the numbers are about 1 to 4 or about 1 to 2 and selection of plural sites is also possible. In the case of substitution, etc. to amino acid having the similar property (charge and/or polarity), it is likely that the desired function is not lost even when many amino acids are substituted. "Amino acid" in the present specification includes all amino acids such as L-amino acid, D-amino acid, α-amino acid, β-amino acid, γ-amino acid, natural amino acid or synthetic amino acid.

When the object peptide is a derivative of natural physiologically active peptide, its amino acid has a homology of preferably not less than 70%, more preferably not less than 80%, still more preferably not less than 90%, particularly preferably not less than 95% and, most preferably, not less than 97% as compared with the native amino acid sequence.

B may be solely bonded provided that the structure of the object peptide to which the half-life-extension peptide fulfills the structure requirement of A and/or C.

Examples of the suitable object peptide include natriuretic peptide or, preferably, atrial natriuretic peptide (ANP; although its origin is not limited, an example is human ANP of SEQ ID No: 100), brain natriuretic peptide (BNP; although its origin is not limited, an example is human BNP of SEQ ID No: 160), C type natriuretic peptide (CNP; although its origin is not limited, an example is CNP-22 of SEQ ID No: 101), motilin (although its origin is not limited, an example is human motilin of SEQ ID No: 102), glucagonic peptide-1 (GLP-1; although its origin is not limited, an example is human GLP-1 (7-36) amide of SEQ ID No: 103), parathyroid hormone (PTH; although its origin is not limited, an example is human PTH (1-34) of SEQ ID No: 104) and calcitonin (CT; although its origin is not limited, an example is human CT of SEQ ID No: 105) which are physiologically active peptide having short half-life or a derivative thereof.

The derivative is able to be selected by such a means that it is made to act on the incubated cells expressing a receptor concerning the original physiologically active peptide and then a marker substance in the culture liquid is measured. In the case of ANP or CNP for example, selection is possible by such a means that it is made to act on the incubated cells expressing GC-A or GC-B which is a receptor thereof and then the cyclic GMP in the culture liquid is measured. In the case of the active peptide acting on the cells expressing GPC-R such as motilin or GLP-1, it is possible to select by measuring the activation of a signal transduction system such as measurement of cyclic AMP in the culture liquid or measurement of intracellular calcium.

The present invention also includes a salt of chimeric peptide. Although any salt may be used provided that the salt is non-toxic, a pharmaceutically acceptable salt is preferred and its example includes salt with inorganic base, salt with organic base, salt with inorganic acid, salt with organic acid and salt with basic or acidic amino acid.

Preferred examples of the salt with inorganic base include alkali metal salt such as sodium salt or potassium salt; alkali earth metal salt such as calcium salt or magnesium salt; and salt such as aluminum salt or ammonium salt.

Preferred examples of the salt with organic base include salt with trimethylamine, triethylamine, pyridine, picoline, ethanolamine, diethanolamine, triethanolamine, dicyclohexylamine or N,N'-dibenzylethylenediamine Preferred examples of the salt with inorganic acid include salt with hydrochloric acid, hydrobromic acid, nitric acid, sulfuric acid or phosphoric acid.

Preferred examples of the salt with organic acid include salt with formic acid, acetic acid, trifluoroacetic acid, fumaric acid, oxalic acid, tartaric acid, maleic acid, citric acid, succinic acid, malic acid, methanesulfonic acid, benzenesulfonic acid or p-toluenesulfonic acid.

Preferred examples of the salt with basic amino acid include salt with arginine, lysine or ornithine. Preferred examples of the salt with acidic amino acid include salt with aspartic acid or glutamic acid.

Among the above salts, preferred salts are those with inorganic base and sodium salt and potassium salt are most preferred.

A chimeric peptide or a pharmaceutically acceptable salt thereof where ANP and BNP are objects is effective for the treatment of acute cardiac insufficiency and acute worsening of chronic cardiac insufficiency based on a physiological action via NPRA (GCA) which is a receptor for ANP and BNP and, in recent years, its very high effect has been noted for an improvement of prognosis after myocardial infarction. Besides the above, it is able to be used as an effective ingredient of a treating agent for obliterative arteriosclerosis, ischemic cardiac disease, hypertension, edema disease, myocardial disease, retinitis, diabetic renal disease, nephrosclerosis, myocardial infarction, etc.

A chimeric peptide or a pharmaceutically acceptable salt thereof where CNP is an object peptide is effective for its application to prevent the restenosis after PTCA after coronary artery stenosis and atypical chondrogenesis insufficiency based on a physiological action via NPRB (GCB) which is a receptor for CNP and also to treat pulmonary hypertension, peripheral artery obliterative disease, osteoarthritis, rheumatoid arthritis, pulmonary fibrosis, hepatic fibrosis, renal fibrosis, myocardial infarction and myocarditis and it is able to be used as an effective ingredient for such a treating agent.

A chimeric peptide or a pharmaceutically acceptable salt thereof where motilin is an object peptide is effective for its application to functional dyspepsia, reflux esophagitis, diabetic gastric motility paralysis, constipation-type irritable bowel syndrome, chronic peudoileus, postoperative ileus, chronic gastritis and atrophic gastritis based on a physiological action via motilin-R which is a receptor for motilin and is able to be used as an effective ingredient of such a treating agent.

A chimeric peptide or a pharmaceutically acceptable salt thereof where GLP-1 is an object peptide is effective for its application to diabetes mellitus, etc. and is able to be used as an effective ingredient for such a treating agent. A chimeric peptide or a pharmaceutically acceptable salt thereof where PTH is an object peptide is effective for its application to hypoparathyroidism, etc. and is able to be used as an effective ingredient for such a treating agent.

(3) Process for Producing a Chimeric Peptide

The present invention also includes a process for producing a chimeric peptide where half-life in plasma is extended and the physiological activity of the object peptide is available in which the half-life-extension peptide of the present invention as mentioned above is bonded to N terminal side, C terminal side or both terminals of the object peptide.

The chimeric peptide according to the present invention is able to be produced by a conventional method (refer, for example, to J. Med. Chem., 43, pp 4370-4376, 2000). For example, it is able to be produced by a recombinant DNA technique and/or chemical synthesis. In a producing process using a recombinant DNA technique for example, host cells transformed by an expression vector having the DNA which codes for the chimeric peptide of the present invention are incubated and the aimed peptide is collected from the cultured product whereupon the chimeric peptide of the present invention is able to be produced.

Examples of the vector into which gene is integrated include vector of *Escherichia coli* (pBR 322, pUC18, pUC19, etc.), vector of *Bacillus subtilis* (pUB110, pTP5, pC194, etc.), vector of yeast (Yep type, YRp type, Yip type, etc.) and vector of animal cells (retrovirus, vaccinia virus, etc.) although any other vector may be used provided that it is able to stably hold the object gene in the host cells. The vector is transduced into an appropriate host cells. As to a method for integrating the aimed object gene into a plasmid or a method for introducing it into the host cells, a method mentioned in Molecular Cloning (Sambrook, et al., 1989) may be utilized for example.

In expressing the chimeric peptide gene in the above plasmid, a promoter is connected to the upstream region of the gene to function.

As to a promoter used in the present invention, anything may be used provided that it is an appropriate promoter corresponding to the host cells used for expression of the object gene. When, for example, the host cell to be transformed is genus *Escherichia*, there may be used lac promoter, trp promoter, 1pp promoter, λ PL promoter, recA promoter, etc. When it is genus *Bacillus*, there may be used SP01 promoter, SP02 promoter, etc. When it is yeast, there may be used GAP promoter, PH05 promoter, ADH promoter, etc. When it is animal cell, there may be used promoter derived from SV40, promoter derived from retrovirus, etc.

Host cells are transformed using a vector containing the object gene produced as above. As to the host cell, there may be used bacteria (such as genus *Escherichia* or genus *Bacillus*), yeast (such as genus *Saccharomyces*, genus *Pichia* or genus *Candida*), animal cell (such as CHO cell or COS cell), etc. As to a medium for the incubation, liquid medium is appropriate and it is particularly preferred that the medium contains carbon source, nitrogen source, etc. necessary for the growth of the transformed cells to be incubated. If desired, vitamins, growth promoting factor, serum, etc. may be added to the medium.

After the incubation, the chimeric peptide of the present invention is separated and purified by a conventional method from the incubated products. For example, in extracting the object substance from the incubated microbes or cells, the microbes or cells are collected after the incubation and suspended in a buffer containing a protein modifier (such as guanidine hydrochloride) and the microbes or cells are disintegrated by ultrasonic wave or the like followed by subjecting to centrifugal separation. In purifying the aimed substance from the supernatant liquid, separating and purifying means such as gel filtration, ultrafiltration, dialysis, SDS-PAGE or various chromatography are conducted by an appropriate combination thereof by taking molecular weight, solubility, charge (isotonic point), affinity, etc. of the object substance into consideration.

The chimeric peptide of the present invention is also able to be chemically synthesized by conventional methods. For example, amino acid having protective groups is condensed by a liquid phase method and/or a solid phase method to elongate the peptide chain, all protective groups are removed by an acid and the resulting crude product is purified to give the aimed product. With regard to a method which is able to be used for the production of the chimeric peptide, various methods have been known already and the chimeric peptide as the substance of the present invention is also able to be easily produced by known methods. For example, a classical peptide synthesis may be used or a solid phase method may be conducted whereby the product is able to be easily produced.

Further, a producing process in which a recombinant DNA technique and a chemical synthesis are combined may be used. Thus, when a half-life-extension peptide is added to side chain of an amino acid concerning the object peptide (such as amino group of lysine residue or carboxylic group of glutamic acid or aspartic acid), production is conducted by a chemical synthesis while, in other parts, production is conducted using a recombinant DNA technique and, after that, the fragments are fused to produce the product.

Such a method may also be grasped as a method where the half-life-extension peptide of the present invention mentioned hereinabove is bonded to N terminal side, C terminal side or both terminal sides of the object peptide whereby the half-life in plasma of the object peptide is elongated.

(4) Pharmaceutical Preparations

The chimeric peptide of the present invention is able to be used as a drug for animals (individuals) including human. The chimeric peptide of the present invention or a pharmaceutically acceptable salt thereof is compounded with a pharmaceutically acceptable carrier whereupon a pharmaceutical composition (pharmaceutical preparation) is able to be manufactured. There is no particular limitation for the dosage form and, for example, the preparation is used as solid preparation or liquid preparation for oral administration or as an injection preparation for parenteral use.

Examples of the solid preparation for oral administration include tablets, pills, capsules, diluted powder and granules while examples of the liquid preparation for oral administration include syrup.

As to a pharmaceutically acceptable carrier, various organic or inorganic carrier substances which have been commonly used as materials for the preparations may be used and examples thereof in the solid preparation include excipient, lubricant, binder and disintegrating agent while examples thereof in the liquid preparation include solvent, solubilizing aid, suspending agent, isotonizing agent, buffer and analgesic agent. If necessary, additives for the preparation such as antiseptic, antioxidant, coloring agent or sweetener may also be used.

Appropriate examples of the excipient include lactose, sugar, D-mannitol, starch, crystalline cellulose and light silicic acid anhydride.

Appropriate examples of the lubricant include magnesium stearate, calcium stearate, talc and colloidal silica.

Appropriate examples of the binder include crystalline cellulose, sugar, D-mannitol, dextrin, hydroxypropyl cellulose, hydroxypropyl methyl cellulose and polyvinylpyrrolidone.

Appropriate examples of the disintegrating agent include starch, carboxymethyl cellulose, carboxymethyl cellulose calcium, croscarmellose sodium and carboxymethyl starch sodium.

Appropriate examples of the solvent include water for injection, alcohol, propylene glycol, Macrogol, sesame oil and corn oil.

Appropriate examples of the solubilizing aid include polyethylene glycol, propylene glycol, D-mannitol, benzyl benzoate, ethanol, trisaminomethane, cholesterol, triethanolamine, sodium carbonate and sodium citrate.

Appropriate examples of the suspending agent include surfactant such as stearyl triethanolamine, sodium lauryl sulfate, laurylaminopropionic acid, lecithin, benzalkonium chloride, benzethonium chloride and glycerol monostearate; and hydrophilic polymer such as polyvinyl alcohol, polyvinylpyrrolidone, carboxymethyl cellulose sodium, methyl cellulose, hydroxymethyl cellulose, hydroxyethyl cellulose and hydroxypropyl cellulose.

Appropriate examples of the isotonizing agent include sodium chloride, glycerol and D-mannitol.

Appropriate examples of the buffer include a buffer liquid such as phosphate, acetate, carbonate or citrate.

Appropriate examples of the analgesic agent include benzyl alcohol.

Appropriate examples of the antiseptic include p-hydroxybenzoates, chlorobutanol, benzyl alcohol, phenethyl alcohol, dehydroacetic acid and sorbic acid.

Appropriate examples of the antioxidant include sulfite and ascorbic acid.

As to the dosage form of the drug of the present invention, a dosage form which is suitable for parenteral administration is preferred. Examples of the dosage form suitable for parenteral administration include injection preparation for intravenous administration, intracutaneous administration, subcutaneous administration or muscular administration, drip, suppository, percutaneous absorber, permucous absorber and inhaling agent. Among the above, the dosage form of an injection preparation is preferred and, particularly when the individual is human in the case of treatment at home, dosage form such as permucous absorber, inhaling agent or suppository is also preferred. Various dosage forms as such are known among persons skilled in the art whereby the persons skilled in the art are able to appropriately select the dosage form which is suitable for the desired administration route and use, if necessary, one or more pharmaceutical additive(s) being utilizable in the related field to manufacture the preparation in the form of a pharmaceutical composition.

For example, a drug in the form of injection or drip is able to be prepared and provided in such a manner that the chimeric peptide endowed with a long half-life which is an effective ingredient is dissolved in distilled water for injection together with one or more appropriate pharmaceutical additive(s) such as such as buffer, sugar solution, isotonizing agent, pH adjusting agent, analgesic agent or antiseptic agent, subjected to a sterilizing filtration (through a filter) and filled in ampoules or vials or the solution subjected to a sterilizing filtration is freeze-dried to prepare a freeze-dried preparation. Examples of the additive usable therefor include saccharide such as glucose, mannitol, xylitol or lactose; hydrophilic polymer such as polyethylene glycol; alcohol such as glycerol; amino acid such as glycine; protein such as serum albumin; salt such as NaCl and sodium citrate; acid such as acetic acid, tartaric acid, ascorbic acid or hyaluronic acid; surfactant such as Tween 80; and reducing agent such as sodium sulfite. The preparation as such is able to be used as injection preparation or drip preparation by addition of distilled water for injection or physiological saline solution thereto to dissolve in actual use. For a permucous administration, an intranasal preparation (preparation for administering via nose) such as intranasal drop or intranasal spray is also suitable. For a perpulmonary administration, inhaling agent is also suitable.

Amount of the chimeric peptide or a pharmaceutically acceptable salt thereof in the preparation varies depending upon the dosage form and it is usually about 0.001 to 1000 mg, preferably about 0.01 to 100 mg, more preferably about 0.1 to 100 mg and, particularly preferably, about 1 to 100 mg.

It is preferred that the above dose is administered one to three times a day or one to seven times a week and the period for the administration varies depending upon the type of the object peptide and is not particularly limited.

The dose of the chimeric peptide or a pharmaceutically acceptable salt thereof according to the present invention may be appropriately determined depending upon the type of the object peptide and also on the half-life of the chimeric peptide.

As such, the present invention includes a method for the treatment of the disease which is able to be treated by the object peptide contained in the pharmaceutical composition by, for example, administering the above-mentioned pharmaceutical composition of the present invention to individuals.

EXAMPLES

The present invention will now be illustrated in more detail by way of the following Examples.

Example 1

Changes in ANP Immunoreactivity Concentration of Native ANP or Chimeric ANP in Plasma Changes in ANP immunoreactivity concentration in plasma when a native ANP and a chimeric peptide (chimeric ANP) to which a half-life-extension peptide was bestowed were administered into vein of rats were investigated.

The experiment was conducted using rats into which polyethylene tube (PE-50; manufactured by Clay Adams) was previously inserted into thigh artery under an anesthetized condition with Nembutal. As a test system, male rats of an SD strain of 7 weeks age (provided from Nippon Charles River) were subjected to the experiment where one group comprised three rats. Native ANP ($\alpha$-hANP, SEQ ID No; 100) or a chimeric ANP (A, B and C) each was administered to the rat intravenously or subcutaneously (back) in a dose of 0.1 mg/kg and blood over the time from before the administration until 90 or 180 minutes after the administration was collected by a polyethylene tube inserted into thigh artery. A stabilizer and EDTA (manufactured by Dojin Laboratories) and aprotinin (manufactured by Bayer) as anti-coagulants were added to the collected blood, plasma was separated by means of centrifugal separation and concentration in plasma was measured by a competitive radioimmunoassay (RIA) (FIG. 1). At that time, a rabbit polyclonal antibody (#8) recognizing a ring part of ANP was used as an antibody and $^{125}$I-[Tyr$^{28}$]$\alpha$-hANP was used as a labeling compound.

Each amino acid sequence of the chimeric ANP (A, B and C) is as follows and all of them retained a human-type guanylate cyclase receptor A (GC-A receptor) agonist activity.

```
Chimeric ANP (A):
                                    (SEQ ID No: 106)
CFGGRMDRIGAQSGLGCNSFRYVQQRKESKKPPAKLQPR
(S-S bond between the underlined members)

Chimeric ANP (B):
                                    (SEQ ID No: 107)
VQQRKESKKPPAKLQPRCFGGRMDRIGAQSGLGCNSFRY
(S-S bond between the underlined members)

Chimeric ANP (C):
                                    (SEQ ID No: 108)
RPQLKAPPKKSEKRQQVCFGGRMDRIGAQSGLGCNSFRY
(S-S bond between the underlined members)
```

Pharmacokinetic parameters were calculated from the resulting changes in immunoreactivity concentrations in plasma. At that time, WinNonlin Professional Ver. 4.0.1 (manufactured by Pharsight Corporation, U.S.A.) was used as the analytical software. Method for the calculation of each parameter is mentioned as follows.

Concentration at time 0 (C0; extrapolated value, ng/mL), area under the curve for concentration in plasma vs. time (AUC; ng.min/mL) and quenching half-life (T½; minute(s)) were calculated as follows. C0 was calculated as a value at time by means of extrapolation from the changes in immunoreactivity concentration in plasma at each blood collection period. AUC was calculated by a trapezoidal method using the immunoreactivity concentrations in plasma at all measuring points (t) and an extrapolated value until the infinitive time was determined. T½ was calculated by means of a least-squares method from the inclination of a straight line connecting several points in a disappearing phase of the immunoreactivity concentration in plasma. In the case of a subcutaneous administration, C0 was not determined but the maximum concentration in plasma (Cmax; ng/mL) and the time reaching the maximum concentration in plasma (Tmax; min) were determined. Cmax was the highest value in the immunoreactivity concentration in plasma at each of the blood collecting stages and, as to Tmax, a blood collecting time where the plasma showed Cmax was adopted.

The result is shown in the following Tables 8 and 9.

TABLE 8

Pharmacokinetic parameters when native ANP and chimeric ANP (A, B and C) thereof were intravenously administered for one time (0.1 mg/kg) to male rats (N = 3)

| Peptide | Dose (mg/kg) | | C0 (ng/mL) | AUC0 → ∞ (ng·min/mL) | T½ (min) | P value |
|---|---|---|---|---|---|---|
| native ANP | 0.1 | Mean Value ± Standard Deviation | 993 ± 208 | 1498 ± 90 | 2.88 ± 0.13 | — |
| Chimeric ANP (A) | 0.1 | Mean Value ± Standard Deviation | 1235 ± 71* | 11777 ± 1374 | 24.0 ± 2.5* | [0.000] |
| Chimeric ANP (B) | 0.1 | Mean Value ± Standard Deviation | 1572 ± 361 | 10527 ± 969 | 40.0 ± 12.4* | [0.007] |
| Chimeric ANP (C) | 0.1 | Mean Value ± Standard Deviation | 1533 ± 442 | 8867 ± 930 | 27.2 ± 3.8* | [0.000] |

*Significant difference was noted from the disappearing half-life of native ANP in the T-test (P < 0.05)

TABLE 9

Pharmacokinetic parameters when native ANP and chimeric ANP (A, B and C) thereof were subcutaneously administered (0.1 mg/kg) to male rats (N = 3)

| Peptide | Dose (mg/kg) | | Cmax (ng/mL) | Tmax (min) | AUC0 → ∞ (ng/min/mL) | T½ (min) | P value |
|---|---|---|---|---|---|---|---|
| Native ANP | 0.1 | Mean Value ± Standard Deviation | 22.3 ± 5.3 | 8.3 ± 2.9 | 535 ± 157 | 11.2 ± 2.0 | — |
| Chimeric ANP (A) | 0.1 | Mean Value ± Standard Deviation | 63.3 ± 31.8 | 5.0 ± 0.0 | 2041 ± 535 | 46.4 ± 8.0* | [0.002] |
| Chimeric ANP (B) | 0.1 | Mean Value ± Standard Deviation | 64.5 ± 40.7 | 16.7 ± 5.8 | 3985 ± 2252 | 57.3 ± 7.1* | [0.000] |
| Chimeric ANP (C) | 0.1 | Mean Value ± Standard Deviation | 55.1 ± 10.3 | 20.0 ± 0.0 | 3402 ± 860 | 37.8 ± 7.8* | [0.007] |

*Significant difference was noted from the disappearing half-life of native ANP in the T-test ($P < 0.05$)

When the chimeric ANP (A, B and C) was intravenously administered, any of those derivatives showed a rising concentration in plasma as compared with the native ANP showing a sustaining property.

Further, when the chimeric ANP (A, B and C) each was subcutaneously administered, any of those derivatives showed a rising concentration in plasma as compared with the native ANP showing a sustaining property.

Example 2

Concentration Changes in Plasma and Biological Activity of Native CNP-22 and Chimeric CNP Changes in CNP immunoreactivity concentration in plasma of native CNP-22 and chimeric peptide (chimeric CNP) where a half-life-extension peptide was added to CNP were investigated.

The experiment was conducted in the same manner as in Example 1 that rats where polyethylene tube was previously inserted into thigh artery were used under an anesthetizing condition with Nembutal and male SD strain rats of 7 weeks age (purchased from Nippon Charles River) were used where one group comprised 3 rats. Native CNP-22 (SEQ ID No: 101) or a chimeric CNP (A and B) each was administered to the rat intravenously (tail) or subcutaneously (back) in a dose of 0.1 mg/kg and the blood over the time from before the administration until 90 or 180 minutes after the administration was collected by a polyethylene tube inserted into thigh artery. EDTA (manufactured by Dojin Laboratories) and aprotinin (manufactured by Bayer) were added as a stabilizer and an anti-coagulant, respectively to the collected blood, the plasma was separated by means of centrifugal separation and concentration in the plasma was measured by means of a competitive RIA. At that time, a rabbit polyclonal antibody (#2) recognizing a ring part of native CNP-22 was used as an antibody and $^{125}$I-[Tyr$^0$] CNP was used as a labeling compound. Pharmacokinetic analysis was carried out by the same method as in Example 1.

Amino acid sequences of the chimeric CNP (A and B) are as follows and both have a human type guanylate cyclase receptor B (GC-B receptor) agonist activity.

```
Chimeric CNP (A):
                                (SEQ ID No: 109)
RPQLKAPPKKSEKRQQVCFGLKLDRIGSMSGLGC
(S-S bond between the underlined members)

Chimeric CNP (B):
                                (SEQ ID No: 110)
CFGLKLDRIGSMSGLGCVQQRKESKKPPAKLQPR
(S-S bond between the underlined members)
```

Figure 2:
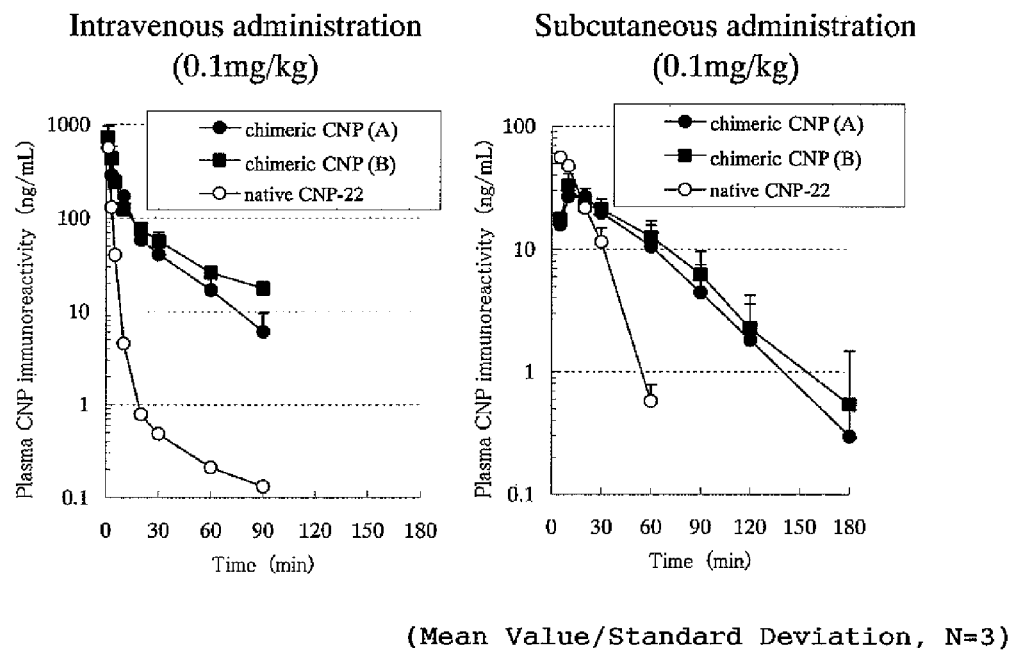
FIG. 2 This is a drawing which shows changes in a CNP immunoreactivity concentration in plasma when native CNP-22 or a chimeric CNP (A and B) thereof (0.1 mg/kg) is intravenously or subcutaneously administered at one time to male rats.

The results are shown in FIG. 2 and the following Tables 10 and 11.

TABLE 10

Pharmacokinetic parameters when native CNP-22 and chimeric CNP (A and B) thereof were intravenously administered (0.1 mg/kg) to male rats (N = 3)

| Peptide | Dose (mg/kg) | | C0 (ng/mL) | AUC0 → ∞ (ng/min/mL) | T½ (min) | P value |
|---|---|---|---|---|---|---|
| Native CNP-22 | 0.1 | Mean Value ± Standard Deviation | 1018 ± 273 | 1537 ± 602 | 2.93 ± 0.23 | — |
| Chimeric CNP (A) | 0.1 | Mean Value ± Standard Deviation | 1034 ± 358 | 6423 ± 553 | 21.7 ± 6.1* | [0.006] |
| Chimeric CNP (B) | 0.1 | Mean Value ± Standard Deviation | 1466 ± 749 | 9194 ± 557 | 36.2 ± 2.3* | [0.000] |

*Significant difference was noted from the disappearing half-life of native CNP-22 in the T-test ($P < 0.05$)

TABLE 11

Pharmacokinetic parameters when native CNP-22 and chimeric CNP (A and B) thereof were subcutaneously administered (0.1 mg/kg) to male rats (N = 3)

| Peptide | Dose (mg/kg) | | Cmax (ng/mL) | Tmax (min) | AUC0 → ∞ (ng/min/mL) | T½ (min) | P value |
|---|---|---|---|---|---|---|---|
| Native CNP-22 | 0.1 | Mean Value ± Standard Deviation | 55.6 ± 4.5 | 5.0 ± 0.0 | 1063 ± 75 | 7.8 ± 0.9* | — |
| Chimeric CNP (A) | 0.1 | Mean Value ± Standard Deviation | 27.9 ± 2.7 | 13.3 ± 5.8 | 1491 ± 493 | 20.7 ± 7.5* | [0.042] |
| Chimeric CNP (B) | 0.1 | Mean Value ± Standard Deviation | 32.8 ± 7.9 | 10.0 ± 0.0 | 1688 ± 617 | 24.0 ± 9.7* | [0.045] |

*Significant difference was noted from the disappearing half-life of native CNP-22 in the T-test ($P < 0.05$)

After the intravenous administration, the native CNP-22 quickly decreased from plasma in a short half-life while, in the chimeric CNP, about 100-fold higher concentration in plasma was retained as compared with the native CNP-22 even after 90 minutes from the administration.

On the other hand, when the native CNP-22 and the chimeric CNP were subcutaneously administered, the maximum concentration in plasma was about ½ in the administration of the chimeric CNP as compared with the native CNP-22 and disappearance from the plasma was slow. From the above result, it is now apparent that, in rats, the chimeric CNP shows along half-life both in the intravenous administration and the subcutaneous administration as compared with the native CNP-22.

Figure 3:
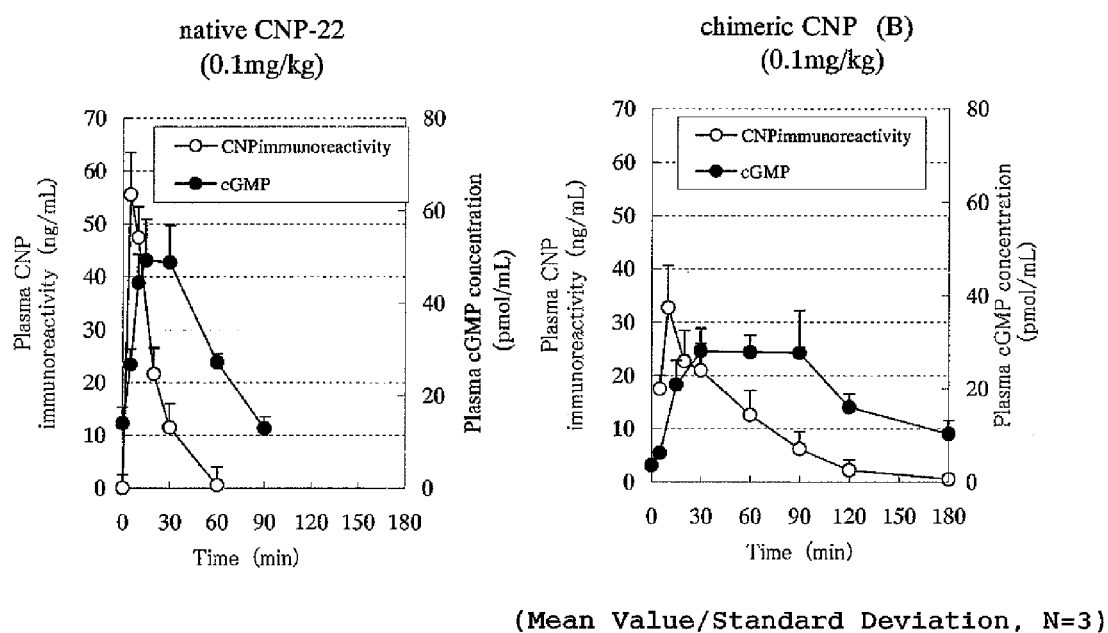
FIG. 3 This is a drawing which shows changes in a CNP immunoreactivity concentration in plasma and in cGMP concentration in plasma when native. CNP-22 or a chimeric CNP (B) thereof (0.1 mg/kg) is subcutaneously administered to male rats.

The native CNP-22 and the chimeric CNP (B) (structure was mentioned already) were subcutaneously administered and the cGMP concentration in plasma which reflects the biological activity of CNP was measured by a competitive RIA (documents). Administration of the drug and collection of the blood were made the same as those in the measurement of CNP immunoreactivity concentration in plasma. In measuring the cGMP concentration in plasma, Yamasa cGMP Assay Kit (manufactured by Yamasa Shoyu) was used as a measuring kit. The result is shown in FIG. 3.

CNP immunoreactivity concentration in plasma after subcutaneous administration of the native CNP-22 quickly rose followed by quick decreasing and it almost disappeared after 60 minutes from the administration. The cGMP concentration In plasma rose slightly slower than the CNP immunoreactivity concentration in plasma and, after reaching its peak after 15 to 30 minutes from the administration, it quickly decreased.

On the other hand, when the chimeric CNP was subcutaneously administered, the maximum value of the CNP immunoreactivity concentration in plasma was lower than the native CNP-22. The cGMP concentration in plasma was also about 60% of the case of the native CNP-22 and is retained in a predetermined level during 30 to 90 minutes after the administration.

Example 3

Resistance of Native CNP-22 and Chimeric CNP to Peptidase

Resistance of native CNP-22 and chimeric CNP to peptidase was investigated.

The experiment was conducted in N=2 for each sample. Native CNP-22, chimeric CNP (A, B) (structure mentioned already; final concentration: 0.5 μg/mL) and 100 μL of reaction solution (medium: 20 mM MES, pH 6.5) of human type recombinant neutral endopeptidase (hNEP, manufactured by R&D Systems, Inc., U.S.A.) were prepared. The initial value sample was boiled for 5 minutes immediately after preparation. Sample for the stability evaluation was subjected to an enzymatic reaction in a constant-temperature vessel set at 37° C. for 1 hour and then boiled for 5 minutes. Distilled water (100 μL) was added to the sample after boiling followed by well mixing and 50 μL thereof was analyzed in a water-acetonitrile system using a high-performance liquid chromatography system LC-10A (manufactured by Shimadzu). The analytical data were analyzed by a Chromato-Pack (CRA-10A, manufactured by Shimadzu) and area of the peak zone of unchanged substance was calculated. The area of average zone of unchanged substance when made to react at 37° C. was divided by the area of average zone of the boiled sample to calculate the residual rate of the unchanged substance after 1 hour. The result is shown in the following Table 12.

TABLE 12

Stability of native CNP-22 and its chimeric CNP (A, B) to hNEP (mean value of N = 2)

| Peptide | Initial Value (%) | Residual Rate (%) |
|---|---|---|
| Native CNP-22 | 100% | 16.7% |
| Chimeric CNP (A) | 100% | 84.3% |
| Chimeric CNP (B) | 100% | 83.8% |

The residual rate of the unchanged native CNP-22 in the sample after the reaction of 1 hour in a constant-temperature vessel set at 37° C. where hNEP was added to a native CNP-22 solution lowered to an extent of 16.7% of the initial value while the residual rates of the chimeric CNP (A and B) were 84.3% and 83.8%, respectively whereupon it was confirmed that each of them showed a resistance to metabolism to hNEP than the native CNP-22.

Further, NEP resistance in vivo of the native CNP-22 and chimeric CNP (B) was evaluated using the effect by the joint use with an NEP inhibitor affecting on changes in CNP immunoreactivity concentration in plasma after the intravenous administration as an index.

This test was also carried out using rats into which a polyethylene tube (PE-50, manufactured by Clay Adams, U.S.A.) was inserted into thigh artery for collection of blood and rats into which a polyethylene tube (PE-10, manufactured by Clay Adams, U.S.A.) was inserted into thigh vein for administration of an NEP inhibitor under an anesthetizing condition using Nembutal. As a test system, male SD strain rats of 7 weeks age (Nippon Charles River; body weight: ca. 250 g) were used for the experiment where one group comprised 3 rats. From the thigh vein, a medium (5% mannitol; 10 μL/min/body) or an NEP inhibitor (30 μg/100 μL/min/body) was intravenously administered at a constant speed. Time for the administration was from 10 minutes before the administration of the native CNP-22 or the chimeric CNP (B) to completion of blood collection which was 60 minutes after the administration. The native CNP-22 and the chimeric CNP (B) each was administered into the tail vein in a dose of 20 µg/kg and the blood before starting the administration of NEP inhibitor (−10 minutes), before the administration of CNP (0 minute) and until after 60 minutes from the administration was collected by a thigh artery cannula. After a stabilizer and an anticoagulant were added to the collected blood, it was centrifuged to give plasma and the immunoreactivity concentration in the plasma was measured by the above-mentioned competitive RIA. The pharmacokinetic analysis was carried out by the same method as in Example 1.

Figure 4:
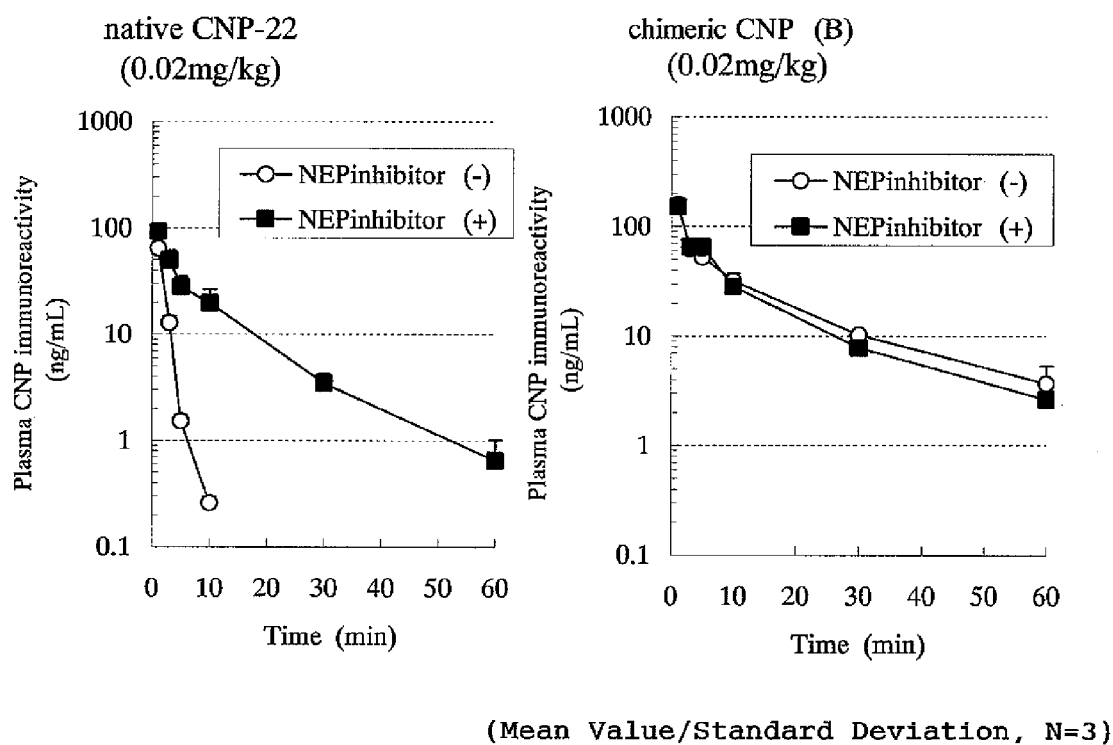
FIG. 4 This is a drawing which shows the influence of NEP inhibitor on changes in CNP immunoreactivity concentration in plasma when native CNP-22 and a chimeric CNP (B) thereof (0.02 mg/kg) are intravenously administered to male rats.

The result is shown in FIG. 4 and the following Table 13.

TABLE 13

Influence of an NEP inhibitor on pharmacokinetic parameters when native CNP-22 and chimeric CNP (B) (ca 0.02 mg/kg) each was intravenously administered to male rats (N = 3)

| Peptide | Dose (mg/kg) | | C0 (ng/mL) | AUC0→∞ (ng · min/mL) | T½ (min) |
|---|---|---|---|---|---|
| Native CNP-22 NEP Inhibitor (−) | 0.02 | Mean Value ± Standard Deviation | 145 ± 20 | 202 ± 24 | 1.96 ± 0.05 |
| Native CNP-22 NEP Inhibitor (+) | 0.02 | Mean Value ± Standard Deviation | 131 ± 32 | 758 ± 88 | 9.94 ± 1.40 |
| Chimeric CNP (B) NEP Inhibitor (−) | 0.02 | Mean Value ± Standard Deviation | 253 ± 15 | 1470 ± 3 | 14.9 ± 3.1 |
| Chimeric CNP (B) NEP Inhibitor (+) | 0.02 | Mean Value ± Standard Deviation | 203 ± 71 | 1342 ± 168 | 12.7 ± 1.2 |

The CNP immunoreactivity concentration in plasma when the native CNP-22 was intravenously administered significantly increased when an NEP inhibitor was used together. The AUC when an NEP inhibitor was used together was about 3.7-fold and a half-life was about 5-fold as compared with the case where the inhibitor was not used.

On the other hand, changes in the CNP immunoreactivity concentration in plasma when the chimeric CNP was administered did not change even when the NEP inhibitor was used together and it was confirmed that, in the body of the rat, the chimeric CNP (B) was hardly decomposed by NEP as compared with the native CNP-22 (Table 13).

Example 4

Extension-promoting Action of Native CNP-22 and Chimeric CNP (1)

An extension-promoting action of native CNP-22 and chimeric CNP was investigated using mice.

In the experiment, female S/VAF Crlj:CD1 (ICR) mice of three weeks age (Nippon Charles River) were used where one group comprised ten mice and 30 mice in total were used for the experiment. The animals (two weeks age) were purchased together with three mother mice and ten baby mice with one mother mouse were bred for one week as a group and then weaned. During the administering period, each group in 5 mice×two cages was bred in a see-through cage. As to water, tap water was made to freely drink and, as to a feed, a solid feed (CRF-1 manufactured by Oriental Yeast Industry) was made to freely ingest. Medium, native CNP-22 or chimeric CNP (B) (structure mentioned already) was repeatedly administered twice daily for 29 days subcutaneously from the back in a dose of 10 mL/kg, 0.25 mg/kg or 0.25 mg/kg, respectively and body length, tail length and body weight during the administered period were measured. The result is shown in FIG. 5.

Figure 5:
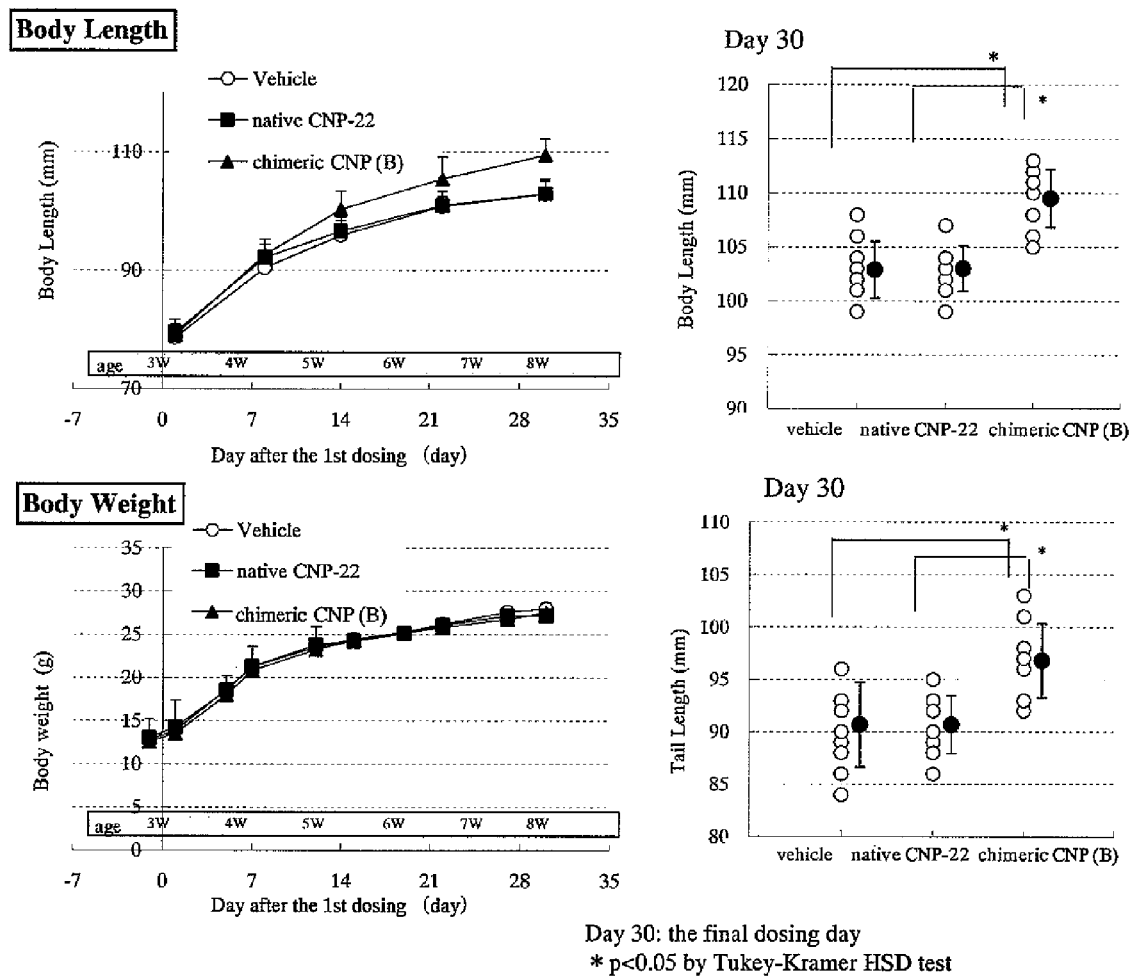
FIG. 5 This is a drawing which shows changes in body length, tail length and body weight when native CNP-22 or a chimeric CNP (B) thereof (0.25 mg/kg) are subcutaneously administered twice daily for 29 days to female mice repeatedly.

As shown in FIG. 5, the body length of the mice to which a chimeric CNP (B) where a half-life-extension peptide was bonded to CNP was repeatedly administered by subcutaneous route significantly increased as compared with a group to which the medium was administered while the body length of the group to which the native CNP-22 was administered showed no difference from the group to which the medium was administered.

On the other hand, with regard to body weight, there was no difference among all administered groups.

Example 5

Antigenicity of Native CNP-22 and Chimeric CNP

In order to investigate whether an antibody to native CNP-22 or chimeric CNP (B) was produced using serum collected from the mice after completion of repeated administration for four weeks in Example 4, antigenicity of each of them was evaluated by means of an indirect ELISA.

A peptide solution (100 µL) adjusted to 1.0 ng/µL using 50 mM of $NaCHO_3$ at pH 8.5 was added to a 96-well plate (manufactured by Nalge Nunc International; Denmark) treated with Maxisoap and subjected to a coating operation overnight at 4° C. A blocking was carried out at room temperature for 1 hour using a 2.0% Block Ace (manufactured by Snow Brand Milk). After the blocking, a serum sample diluted to an extent of $10^2$ to $10^5$ fold was added thereto and the mixture was subjected to an antigen-antibody reaction at room temperature for 1 hour. After washing the wells, an anti-mouse IgG HRPAb (manufactured by Zymed Laboratories, U.S.A.) was added thereto. The antigen-antibody reaction was conducted for 1 hour at room temperature, then the wells were washed and a substrate ABTS (manufactured by KPL, U.S.A.) was added thereto. After the reaction at room temperature for 1 hour, absorbance of 405 nm was measured by Spectra Max 190 (manufactured by Molecular Devices, U.S.A.) and the degree of coloration was analyzed as an antibody value.

As a result, even when the native CNP-22 or the chimeric CNP (B) was repeatedly administered subcutaneously (back) in a dose of 0.25 mg/kg twice daily for 29 days, no rise of the antibody value to native CNP-22 and to chimeric CNP (B) was noted.

Example 6

Half-life in Plasma of Native Motilin and Chimeric Motilin) (1)

Figure 6:
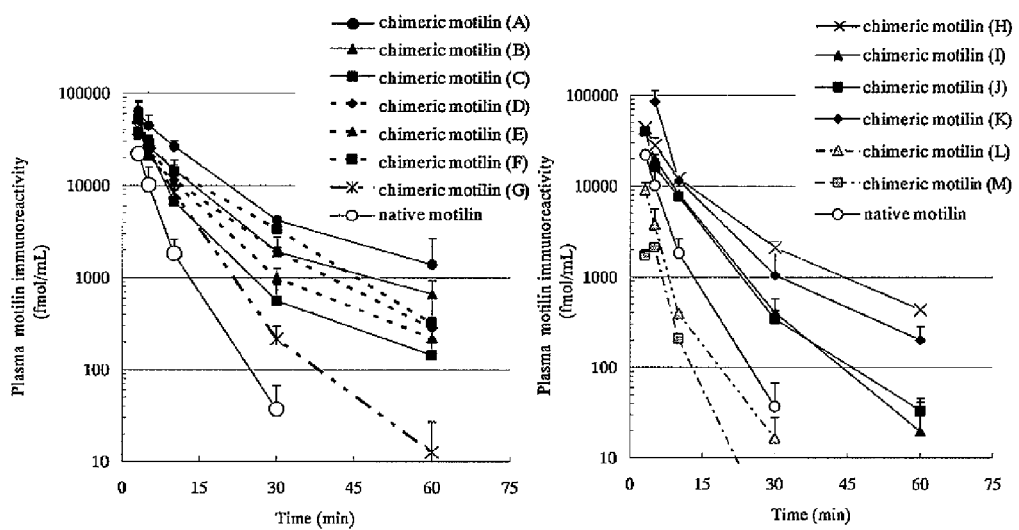
FIG. 6 This is a drawing which shows changes in amotilin immunoreactivity concentration in plasma when motilin or a chimeric motilin thereof (A to M) (10 nmol/kg) is intravenously administered to male rats.

Changes in motilin immunoreactivity concentrations in plasma when native motilin (SEQ ID No: 102) and 13 kinds of chimeric motilins A to M (SEQ ID Nos: 111 to 123) half-life-extension peptide in various half lives comprising 5 to 22 amino acid residues were bonded to an amino acid sequence of amino acid numbers 1 to 12 of SEQ ID No: 102 which was the active center of native motilin were intravenously administered were investigated. The experiment was carried out using rats into which polyethylene tube (PE-50 manufactured by Clay Adams) was previously inserted into thigh artery under an anesthetized condition with Nembutal. As to a test system, male SD strain rats (Nippon Charles River) of 7 weeks age were used where one group comprised 3 rats. Human type motilin or a derivative thereof in a dose of 10 nmol/kg was administered into tail vein of the rat and the blood before the administration and until 60 minutes after the administration was collected by a polyethylene tube inserted into the thigh artery. To the collected blood were added EDTA (manufactured by Dojin Laboratories) and aprotinin (manufactured by Bayer) as a stabilizer and an anti-coagulant, respectively and the plasma was separated therefrom by centrifugal separation. Motilin immunoreactivity concentration in the plasma was measured by a competitive radioimmunoassay (RIA) (FIG. 6). At that time, a rabbit polyclonal antibody (#870623) which specifically recognizes the amino acid numbers 1 to 12 of native motilin shown by SEQ ID No: 102 was used as an antibody and, as a labeled compound, $^{125}$I-[Tyr$^7$] human type motilin was used.

Amino acid sequences, molecular weights and half-time for disappearance from the plasma for the native motilin and chimeric motilin (A to M) are shown in the following Table 14.

TABLE 14

List of amino acid sequences, molecular weights and half-time for disappearance from the plasma for chimeric motilin upon intravenous administration to rats (Mean value ± standard deviation; N = 3)
$T^{1}/_{2}$ (min)

| Peptide | SEQ ID NO: | Amino Acid Sequence | Mol. Wt. | Mean Value | ±SD | P Value |
|---|---|---|---|---|---|---|
| Native Motilin | 102 | FVPIFTYGELQRMQEKERNKGQ | 2699.05 | 3.26 | ±0.95* | — |
| Chimeric motilin (A) | 111 | FVPIFTYGELQRSPEHQRVQQRKESKKPPAKLQPR | 4204.79 | 11.74 | ±3.36* | 0.014 |
| Chimeric motilin (B) | 112 | FVPIFTYGELQREHQRVQQRKESKKPPAKLQPR | 4020.60 | 11.14 | ±0.73* | 0.000 |
| Chimeric motilin (C) | 113 | FVPIFTYGELQRQRVQQRKESKKPPAKLQPR | 3754.35 | 8.90 | ±0.53* | 0.001 |
| Chimeric motilin (D) | 114 | FVPIFTYGELQRVQQRKESKKPPAKLQPR | 3470.03 | 8.90 | ±0.50* | 0.001 |
| Chimeric motilin (E) | 115 | FVPIFTYGELQRQRKESKKPPAKLQPR | 3242.77 | 8.03 | ±0.73* | 0.002 |
| Chimeric motilin (F) | 116 | FVPIFTYGELQRKESKKPPAKLQPR | 2958.46 | 9.37 | ±0.58* | 0.000 |
| Chimeric motilin (G) | 117 | FVPIFTYGELQRSKKPPAKLQPR | 2701.17 | 5.25 | ±1.32NS | 0.101 |
| Chimeric motilin (H) | 118 | FVPIFTYGELQRVQQRKESKKPPAKLQ | 3216.73 | 10.43 | ±0.14* | 0.000 |
| Chimeric motilin (I) | 119 | FVPIFTYGELQRVQQRKESKKPPAK | 2975.45 | 5.76 | ±0.66* | 0.018 |
| Chimeric motilin (J) | 120 | FVPIFTYGELQRVQQRKESKKPP | 2776.20 | 6.34 | ±0.48* | 0.008 |
| Chimeric motilin (K) | 121 | FVPIFTYGELQRVQQRKESKK | 2581.97 | 6.14 | ±2.37* | 0.032 |
| Chimeric motilin (L) | 122 | FVPIFTYGELQRVQQRKES | 2325.62 | 4.89 | ±4.26NS | 0.296 |
| Chimeric motilin (M) | 123 | FVPIFTYGELQRVQQRK | 2109.43 | 2.39 | ±2.37NS | 0.272 |

*In t-test, a significant difference was available from the disappearance half-time of native motilin (p < 0.05)
NS: In t-test, a significant difference was not available from the disappearance half-time of native motilin (p >0.05)

The result is shown in FIG. 6 as well.

All of the 13 types of chimeric motilins which were evaluated retained the human motilin receptor agonist activity. With regard to the chimeric motilin (G, L and M), more significant disappearance half-time extending action in vivo than native motilin was unable to be confirmed and it was confirmed that, when the structure of the amino acid sequence ESKK (SEQ ID NO: 168) was lost, the action disappeared. With regard to other motives, all of them had an action of extending the half-life in vivo as compared with the native motilin and, among them, the fact whether the structure of RKESKK (SEQ ID NO: 162) is held or not has the biggest influence on the extending action for the half-life.

Example 7

Half-life of Native CNP-22 and Chimeric CNP in Plasma (1)

Changes in CNP immunoreactivity concentration in plasma when the native CNP-22 shown in SEQ ID No: 101 and seven kinds of chimeric CNPs (C to I) (SEQ ID Nos: 124 to 130) in which a half-life-extension peptide comprising 17 amino acid residues was bonded to N terminal, C terminal or both terminals of the peptide comprising the 6th to 22nd amino acid sequence from N terminal in SEQ ID No: 101 which was the active center of the native CNP-22 were intravenously administered were investigated.

The experiment was carried out using rats into which polyethylene tube (PE-50 manufactured by Clay Adams) was previously inserted into thigh artery under an anesthetized condition with Nembutal. As to a test system, male SD strain rats (Nippon Charles River) of 7 weeks age were used where one group comprised 3 rats. Native CNP-22 or chimeric CNP in a dose of 10 nmol/kg was administered into tail vein of the rat and the blood before the administration and until 60 minutes after the administration was collected by a polyethylene tube inserted into the thigh artery. To the collected blood were added EDTA (manufactured by Dojin Laboratories) and aprotinin (manufactured by Bayer) as a stabilizer and an anti-coagulant, respectively and the plasma was separated therefrom by centrifugal separation. CNP immunoreactivity concentration in plasma was measured by a competitive radioimmunoassay (RIA). At that time, a rabbit polyclonal antibody (#2) which specifically recognizes the ring partial structure of the native CNP-22 was used as an antibody and, as a labeled compound, $^{125}$I-[Tyr$^0$] CNP was used.

Amino acid sequences, molecular weights and half-time for disappearance from the plasma for chimeric CNP are shown in the following Table 15.

TABLE 15

List of amino acid sequences, molecular weights and half-time for disappearance from the plasma for native CNP-22 and chimeric CNP (C to I) upon intravenous administration to rats in a dose of 10 nmmol/kg (Mean value ± standard deviation; N = 3)

| Peptide | SEQ ID NO: | Amino Acid Sequence | Mol Wt | T1/2 (min) Mean Value | ±SD | P Value |
|---|---|---|---|---|---|---|
| Native CNP-22 | 101 | GLSKG*C*FGLKLDRIGSMSGLG*C* | 2197.6 | 4.34 | ±0.20 | — |
| Chimeric CNP(C) | 110 | *C*FGLKLDRIGSMSGLG*C*VQQRKESKKPPAKLQPR | 3755.5 | 15.03 | ±4.31* | 0.013 |
| Chimeric CNP(D) | 125 | GLSKG*C*FGLKLDRIGSMSGLG*C*VQQRKESKKPPAKLQPR | 4198.0 | 20.30 | ±3.09* | 0.001 |
| Chimeric CNP(E) | 126 | VQQRKESKKPPAKLQPR*C*FGLKLDRIGSMSGLG*C*VQQRKESKKPPAKLQPR | 5755.9 | 18.40 | ±2.05* | 0.000 |
| Chimeric CNP(F) | 127 | RPQLKAPPKKSEKRQQV*C*FGLKLDRIGSMSGLG*C*VQQRKESKKPPAKLQPR | 5755.9 | 17.38 | ±1.00* | 0.000 |
| Chimeric CNP(G) | 128 | VQQRKESKKPPAKLQPR*C*FGLKLDRIGSMSGLG*C* | 3755.5 | 17.75 | ±3.99* | 0.004 |
| Chimeric CNP(H) | 129 | RPQLKAPPKKSEKRQQV*C*FGLKLDRIGSMSGLG*C* | 3755.5 | 14.86 | ±2.64* | 0.002 |
| Chimeric CNP(I) | 130 | *C*FGLKLDRIGSMSGLG*C*VQQRKESKKPPAKLQPR-amide | 3754.5 | 14.50 | ±0.85* | 0.000 |

In all of them, S-S bond was formed at the underlined italic cysteine residues to form a cyclic structure.
*In t-test, a significant difference was available from the disappearance half-time of native CNP-22 (p <0.05)

Figure 7:
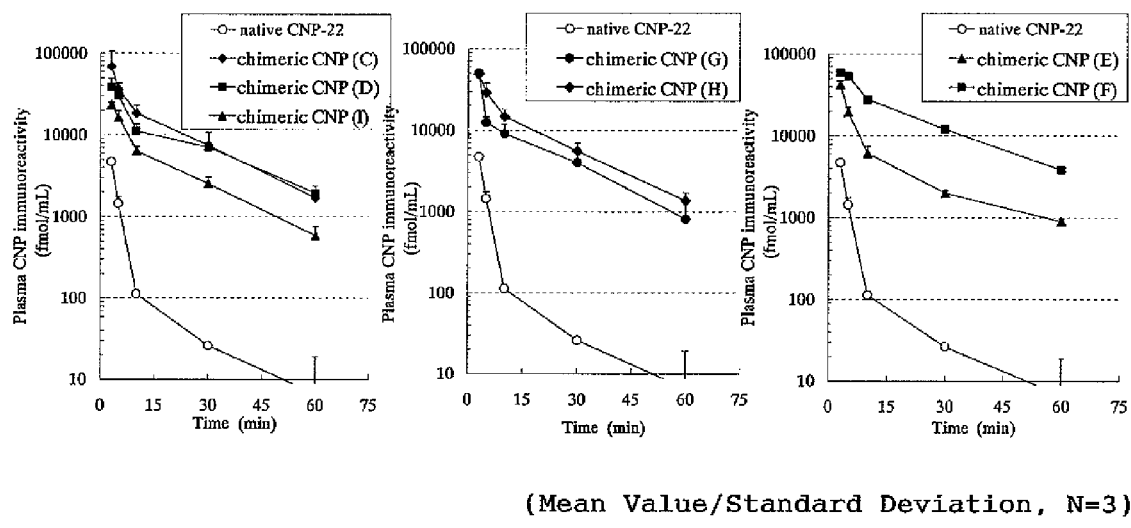
FIG. 7 This is a drawing which shows changes in a CNP immunoreactivity concentration in plasma when native CNP-22 or a chimeric CNP (C to I) (10 nmol/kg) is intravenously administered to male rats.

The result is shown in FIG. 7 as well.

All of the evaluated chimeric CNPs (C to I) retained the human CNP receptor agonist activity.

All of the chimeric CNPs evaluated at this time showed longer disappearance half-life than the native CNP-22. Therefore, it was found that the half-life extension peptide evaluated at this time showed an extending action for half-life when it was bonded to any of N terminal side and C terminal side or to both sides and that, even when the amino acid sequence was reversed, the property was not deteriorated. It was also found that, even when the C terminal structure was amidated, an extending action for the half-life was still available whereby, depending upon the structure of the aimed peptide, a bonding system was able to be selected.

Example 8

Half-life of Native Motilin and Chimeric Motilin in Plasma (2)

Changes in motilin immunoreactivity concentrations in plasma when native motilin (SEQ ID No: 102) and 26 kinds of chimeric motilins (N to Z and I to XIII) (SEQ ID Nos: 131 to 156) where half-life-extension peptide in various half lives comprising 14 to 22 amino acid residues were bonded to an amino acid sequence of amino acid numbers 1 to 12 of SEQ ID No: 102 which was the active center of native motilin were intravenously administered were investigated.

Figure 8:
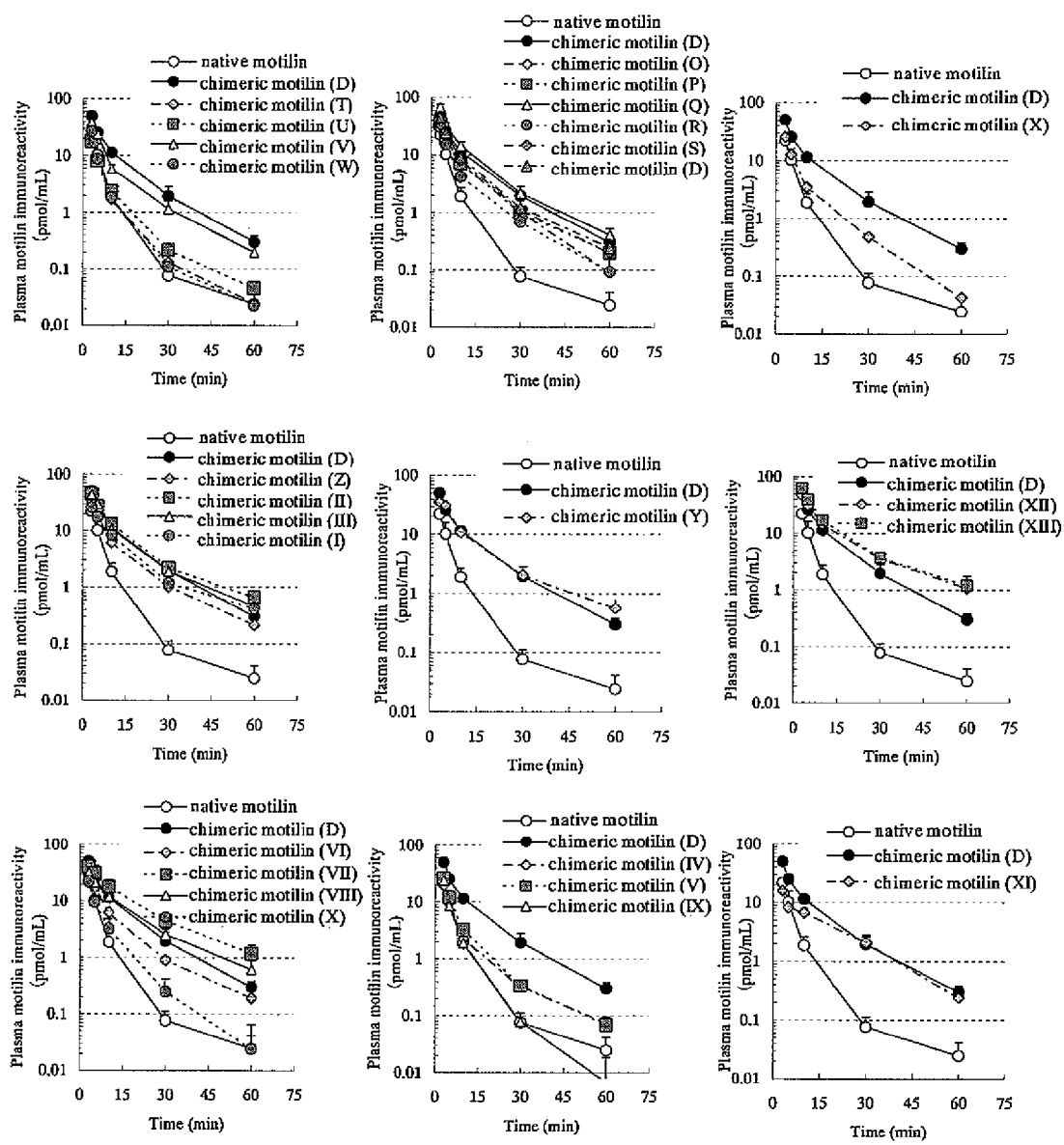
FIG. 8 This is a drawing which shows changes in a CNP immunoreactivity concentration in plasma when a chimeric motilin (N to V, X to Z and I to XIII) (10 nmol/kg) is intravenously administered.

The experiment was carried out using rats into which polyethylene tube (PE-50 manufactured by Clay Adams) was inserted into thigh artery under an anesthetized condition with Nembutal. As to a test system, male SD strain rats (Nippon Charles River) of 7 weeks age were used where one group comprised 3 rats. Human motilin or a derivative thereof in a dose of 10 nmol/kg was administered into tail vein of the rat and the blood before the administration and until 60 minutes after the administration was periodically collected by a polyethylene tube inserted into the thigh artery. To the collected blood were added EDTA (manufactured by Dojin Laboratories) and aprotinin (manufactured by Bayer) as a stabilizer and an anti-coagulant, respectively and the plasma was separated therefrom by centrifugal separation. Motilin immunoreactivity concentration in plasma was measured by a competitive radioimmunoassay (RIA) (FIG. 8). At that time, a rabbit polyclonal antibody (#870623) which specifically recognizes the amino acid numbers 1 to 12 of native motilin shown by SEQ ID No: 102 was used as an antibody and, as a labeled compound, $^{125}$I-[Tyr$^7$] human motilin was used.

Amino acid sequences, molecular weights and half-time for disappearance from the plasma for the native motilin and chimeric motilins (N to Z and I to XIII) are shown in the following Table 16 and FIG. 8.

TABLE 16

List of amino acid sequences, molecular weights and half-time for disappearance from the plasma for chimeric motilins upon intravenous administration to rats in a dose of 10 nmmol/kg

| | | | | (Mean value ± standard deviation; N = 3) $T^1/_2$ (min) | | |
|---|---|---|---|---|---|---|
| Peptide | SEQ ID NO: | Amino Acid Sequence | Mol Wt | Mean Value | ±SD | P Value |
| Native Motilin | 102 | FVPIFTYGELQRMQEKERNKGQ | 2699.1 | 3.26 | ±0.95 | — |
| Chimeric motilin (D) | 114 | FVPIFTYGELQRVQQRKESKKPPAKLQPR | 3470.0 | 8.90 | ±0.50* | 0.001 |
| Chimeric motilin (N) (MG-dS) | 131 | FVPIFTYGELQRVQQRKEKKPPAKLQPR | 3383.0 | 9.12 | ±1.22* | 0.003 |
| Chimeric motilin (O) (MG-18S/F) | 132 | FVPIFTYGELQRVQQRKEFKKPPAKLQPR | 3530.2 | 7.73 | ±1.14* | 0.007 |
| Chimeric motilin (P) (MG-18S/T) | 133 | FVPIFTYGELQRVQQRKETKKPPAKLQPR | 3484.1 | 9.67 | ±0.13* | 0.000 |
| Chimeric motilin (Q) (MG-18S/P) | 134 | FVPIFTYGELQRVQQRKEPKKPPAKLQPR | 3480.1 | 9.65 | ±0.96* | 0.001 |
| Chimeric motilin (R) (MG-18S/L) | 135 | FVPIFTYGELQRVQQRKELKKPPAKLQPR | 3496.2 | 9.13 | ±0.67* | 0.001 |
| Chimeric motilin (S) (MG-18S/A) | 136 | FVPIFTYGELQRVQQRKEAKKPPAKLQPR | 3454.1 | 9.29 | ±0.30* | 0.000 |
| Chimeric motilin (T) (MG-17E/N) | 137 | FVPIFTYGELQRVQQRKNSKKPPAKLQPR | 3455.1 | 5.47 | ±0.22* | 0.017 |
| Chimeric motilin (U) (MG-17E/Q) | 138 | FVPIFTYGELQRVQQRKQSKKPPAKLQPR | 3469.1 | 5.66 | ±0.66* | 0.023 |
| Chimeric motilin (V) (MG-ES/DS) | 139 | FVPIFTYGELQRVQQRKDSKKPPAKLQPR | 3456.1 | 10.14 | ±0.92* | 0.001 |
| Chimeric motilin (W) (MG-dES) | 140 | FVPIFTYGELQRVQQRKKKPPAKLQPR | 3253.9 | 5.39 | ±1.23$^{NS}$ | 0.077 |
| Chimeric motilin (X) (MG-17E/D) | 141 | FVPIFTYGELQRVQQRKDSRRPPAKLQPR | 3512.1 | 7.89 | ±0.34* | 0.001 |

TABLE 16-continued

List of amino acid sequences, molecular weights and half-time for disappearance from the plasma for chimeric motilins upon intravenous administration to rats in a dose of 10 nmmol/kg (Mean value ± standard deviation; N = 3)

| Peptide | SEQ ID NO: | Amino Acid Sequence | Mol Wt | $T^{1}/_{2}$ (min) Mean Value | ±SD | P Value |
|---|---|---|---|---|---|---|
| Chimeric motilin (Y) (MG-BR) | 142 | FVPIFTYGELQRVQQKKSEKRPPAKLQPR | 3470.1 | 11.60 | ±1.18* | 0.001 |
| Chimeric motilin (Z) (MG-i17G) | 143 | FVPIFTYGELQRVQQRKGESKKPPAKLQPR | 3527.1 | 10.53 | ±1.66* | 0.003 |
| Chimeric motilin (I) (MG-i19G) | 144 | FVPIFTYGELQRVQQRKESGKKPPAKLQPR | 3527.1 | 11.55 | ±2.00* | 0.003 |
| Chimeric motilin (II) (MG-i17G2) | 145 | FVPIFTYGELQRVQQRKGGESKKPPAKLQPR | 3584.2 | 11.50 | ±0.64* | 0.000 |
| Chimeric motilin (III) (MG-i17G2-19iG) | 146 | FVPIFTYGELQRVQQRKGGESGKKPPAKLQPR | 3641.2 | 10.65 | ±0.72* | 0.000 |
| Chimeric motilin (IV) (MG-dPP) | 147 | FVPIFTYGELQRVQQRKESKKAKLQPR | 3196.8 | 7.73 | ±0.52* | 0.002 |
| Chimeric motilin (V) (MG-dPPH1) | 148 | FVPIFTYGELQRVQQRKESKKAKLAALKA | 3349.0 | 8.94 | ±0.68* | 0.001 |
| Chimeric motilin (VI) (MG-H1) | 149 | FVPIFTYGELQRVQQRKESKKPPAKLAALKA | 3543.2 | 9.94 | ±0.30* | 0.000 |
| Chimeric motilin (VII) (MG-H3) | 150 | FVPIFTYGELQRVQQRKESKKPPAELAALEA | 3545.1 | 12.78 | ±0.27* | 0.000 |
| Chimeric motilin (VIII) (MG-H4) | 151 | FVPIFTYGELQRVQQRKESKKPPAELAALKA | 3544.2 | 11.56 | ±0.93* | 0.000 |
| Chimeric motilin (IX) (MG-dPPS) | 152 | FVPIFTYGELQRVQQRKESKKMITIR | 3196.8 | 4.39 | ±0.38[NS] | 0.170 |
| Chimeric motilin (X) (MG-S) | 153 | FVPIFTYGELQRVQQRKESKKPPMITIR | 3391.0 | 5.25 | ±0.45* | 0.031 |
| Chimeric motilin (XI) (MG-d12/14) | 154 | FVPIFTYGELQRKESKKPPAKLAALKA | 3031.6 | 10.29 | ±1.00* | 0.001 |
| Chimeric motilin (XII) (MGP1) | 155 | FVPIFTYGELQRVQQKKAYSPDKERKPPALQPR | 3916.5 | 13.03 | ±0.98* | 0.000 |
| Chimeric motilin (XIII) (MGP2) | 156 | FVPIFTYGELQRVQQKKAYSPDKERKPPAKLQPR | 4044.7 | 13.09 | ±2.90* | 0.005 |

*In t-test, a significant difference was available from the disappearance half-time of native motilin (p < 0.05)
[NS]In t-test, a significant difference was not available from the disappearance half-time of native motilin (p > 0.05)

From the result for the chimeric motilin (XI) (MG-d12/14) together with the result for the chimeric motilins (A to M) concerning Example 6, it was shown that, with regard to A in the formula of the half-life-extension peptide of the present invention, that may not be present or that may have a sequence of any amino acid numbers. As to the length when the sequence is present, it was shown to be the length of about 1 to 9 amino acid(s), preferably 3 to 9 amino acids, more preferably 3 amino acid and, most preferably, Val-Gln-Gln.

From the result for the chimeric motilins (T) (MG-17E/N), (U) (MG-17E/Q) and (W) (MG-Des), it was shown that E(Glu) in RKESKK (SEQ ID NO: 162) in the structure (core sequence: RKESKK sequence part (SEQ ID NO: 162)) necessary for extension of half-life concerning the present invention is an amino acid which is necessary for the action of half-life extension and that, from the result for the chimeric motilins (V) (MG-ES/DS) and (X) (MG-17E/D), the amino acid is able to be substituted with D(Asp). Thus, it was shown that the amino acid at the position of the above E(Glu) may be any acidic amino acid.

From the result for the chimeric motilins (O) (MG-18S/F), (P) (MG-18S/T), (Q) (MG-18S/P), (R) (MG-18S/L) and (S) (MG-18S/A), it was shown that S(Ser) in RKESKK (SEQ ID NO: 162) is able to be substituted with T(Thr), P(Pro), L(Leu), F(Phe) or A(Ala). Thus, it was shown that the amino acid at the position of the above S(Ser) is able to be substituted with an amino acid having any side-chain structure such as aromatic amino acid, hydrophobic amino acid or polar non-charged amino acid. It was also shown that, from the result for the chimeric motilin (N) (MG-dS), the amino acid at the position of the above S(Ser) may not be present.

From the result for the chimeric motilin (X) (MG-17E/D), it was shown that each of R(Arg) and K(Lys) in RKESKK (SEQ ID NO: 162) is able to be substituted with any basic amino acid.

It is characteristic that the RKESKK sequence part (SEQ ID NO: 162) contains a basic amino acid cluster (a continued sequence of two basic amino acids) and an acidic amino acid and, from the result for the chimeric motilins (Z) (MG-i17G), (I) (MG-i19G), (II) (MG-i17G2) and (III) (MG-i17G2-i19G), it was shown that the distance in the cluster is able to be expanded by insertion of any amino acid.

From the result for each chimeric peptide mentioned in Table 16, it was shown that the distance in the basic amino acid cluster is 1 to 5 amino acids.

From the result for the chimeric motilin (Y) (MG-BR), it was shown that the alignment of RKESKK (SEQ ID NO: 162) may be reversed (KKSEKR) (SEQ ID NO: 163).

From the result for the chimeric motilins (XII) (MGP1) and (XIII) (MGP2), it was shown that the action for extending the half-life is potentiated even when two sequences corresponding to the core sequence are aligned in tandem and it was shown that the presence of plural core sequences in a molecule is also an effective means for achieving the longer extension of half-life in blood.

The chimeric motilins (VI) (MG-H1), (VII) (MG-H3) and (VIII) (MG-H4) are peptides where, at the part concerning C in the formula of the half-life-extension peptide according to the present invention, a sequence which is able to be predicted to form an α-helix structure by a known method for predicting the secondary structure (Chou-Fasman method: Biochemistry. 1974 Jan. 15; 13(2):222-45 Prediction of protein conformation. Chou P Y, Fasman G D, or Garnier method: J Mol. Biol. 1978 Mar. 25; 120(1):97-120. Analysis of the accuracy and implications of simple methods for predicting the secondary structure of globular proteins. Garnier J, Osguthorpe D J, Robson B.) is aligned in connection to the two Pro's (Pro-Pro sequence). From the result for those chimeric peptides, it was shown that, as to C in the formula of the half-life-extension peptide of the present invention, it is preferred to align any amino acid sequence which is able to form an α-helix structure.

Further, as shown by the comparison of the chimeric motilin (IV) (MG-dPP) with the chimeric motilin D, the comparison of the chimeric motilin (V) (MG-dPPH1) with the chimeric motilin (VI) (MG-H1) and the comparison of the chimeric motilin (IX) (MG-dPPS) with the chimeric motilin (X) (MG-S), it was shown that, when no P(Pro) is present at the N terminal of the amino acid sequence corresponding to the formula C of the half-life-extension peptide concerning the present invention, it is preferred to align a P(Pro) sequence (in Pro numbers within such a range of making the amino acid numbers of C 2 to 14 or, preferably, Pro-Pro) at the site.

Example 9

Half-life of Native CNP-22 and Chimeric CNP in Plasma (2)

Changes in CNP immunoreactivity concentration in plasma when the native CNP-22 shown in SEQ ID No: 101 and chimeric CNPs (D, J and K) (J of the chimeric CNP is SEQ ID No: 157 and K of the chimeric CNP is SEQ ID No: 158) in which a half-life-extension peptide comprising 17 or 20 amino acid residues was bonded to C terminal of the peptide comprising the 6th to 22nd amino acid sequence from N terminal in SEQ ID No: 101 which was the active center of the native CNP-22 were intravenously administered were investigated.

The experiment was carried out using rats into which polyethylene tube (PE-50 manufactured by Clay Adams) was inserted into thigh artery under an anesthetized condition with Nembutal. As to a test system, male SD strain rats (Nippon Charles River) of 7 weeks age were used where one group comprised 3 rats. Native CNP-22 or chimeric CNP in a dose of 20 nmol/kg was administered into tail vein of the rat and the blood before the administration until 90 minutes after the administration was collected by a polyethylene tube inserted into the thigh artery. To the collected blood were added EDTA (manufactured by Dojin Laboratories) and aprotinin (manufactured by Bayer) as a stabilizer and an anti-coagulant, respectively and the plasma was separated therefrom by centrifugal separation. The concentration in plasma was measured by a competitive radioimmunoassay (RTA). At that time, a rabbit polyclonal antibody (#2) which specifically recognizes the ring partial structure of the native CNP-22 was used as an antibody and, as a labeled compound, $^{125}$I-[Tyr$^0$] CNP was used.

Figure 9:
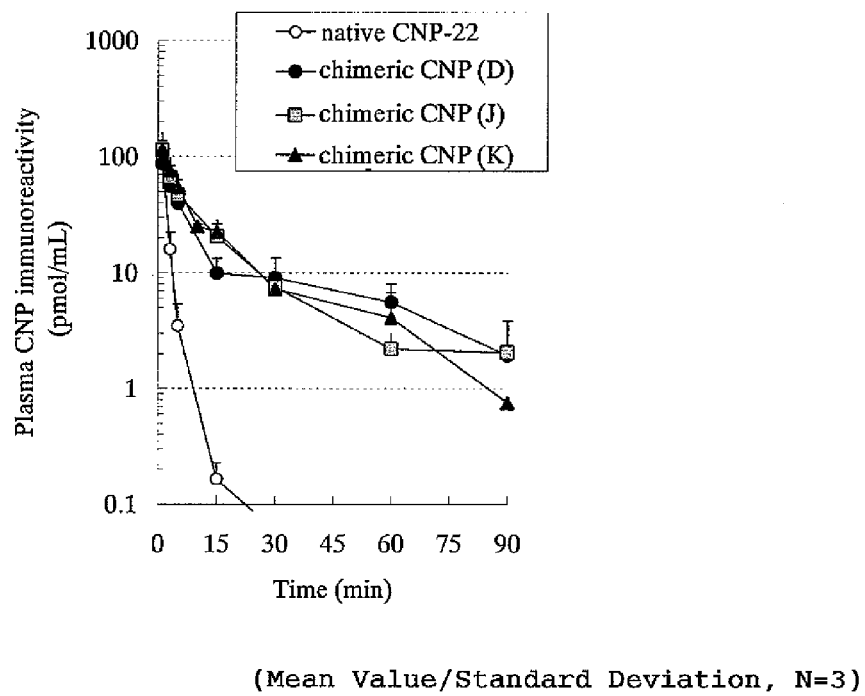
FIG. 9 This is a drawing which shows changes in a CNP immunoreactivity concentration in plasma when native CNP-22 or a chimeric CNP (D, J and K) (20 nmol/kg) is intravenously administered to male rats.

Amino acid sequences, molecular weights and half-time for disappearance from the plasma for chimeric CNP are shown in the following Table 17 and FIG. 9.

TABLE 17

List of amino acid sequences, molecular weights and half-time for disappearance from the plasma for native CNP-22 and chimeric CNPs (D, J and K) upon intravenous administration to rats in a dose of 20 nmmol/kg

| Peptide | SEQ ID NO: | Amino Acid Sequence | Mol Wt | Mean Value | ±S.D. | P Value |
|---|---|---|---|---|---|---|
| | | | | (Mean value ± standard deviation; N = 3) $T^1/_2$ (min) | | |
| Native CNP-22 | 101 | GLSKGCFGLKLDRIGSMSGLGC | 2198 | 1.60 | ±0.50 | — |
| Chimeric CNP (D) | 125 | GLSKGCFGLKLDRIGSMSGLGCVQQRKESKKPPAKLQPR | 4198 | 43.59 | ±10.58* | 0.002 |
| Chimeric CNP (J) (ED Substituted Product) | 171 | GLSKGCFGLKLDRIGSMSGLGCVQQRKDSKKPPAKLQPR | 4184 | 31.24 | ±4.79* | 0.000 |
| Chimeric CNP (K) (CO1-KR) | 158 | CFGLKLDRIGSMSGLGCAGSVDHKGKQRKVVDHPKR | 3880 | 18.03 | ±4.72* | 0.004 |

*In t-test, a significant difference was available from the disappearance half-time of native CNP-22 (p < 0.05)

All of the chimeric CNPs evaluated at this time showed a significantly longer half-life for disappearance than the native CNP-22.

From the result of the chimeric CNP (J), it was shown that, with regard to E(Glu) in RKESKK (SEQ ID NO: 162) concerning B (core sequence) of the formula of the half-life-extension peptide concerning the present invention, D(Asp) is acceptable instead of E.

Further, from the result of the chimeric CNP (K), it was shown that any amino acid (for example, Val (which may be in plural), H or P) may be present between E and basic amino acid cluster (RK, KK) in RKESKK (SEQ ID NO: 162) concerning B (core sequence) of the formula of the half-life-extension peptide of the present invention. Furthermore, it was shown that the part concerning A of the formula of the half-life-extension peptide of the present invention does not particularly require a specific amino acid sequence but any amino acid may be used. For example, the amino acid numbers for the part concerning A will be acceptable provided that they are within 10.

Example 10

Extension-promoting Action of Chimeric CNP (2)

Dose-dependency of the extension-elongation action of the chimeric CNPs (D, 3) was investigated using mice.

In the experiment, female S/VAF Crlj:CD1 (ICR) mice of three weeks age (Nippon Charles River) were used where one group comprised ten mice and 30 mice were used for the experiment in total. The animals (two weeks age) were purchased together with three mother mice and ten baby mice with one mother mouse were bred for one week as a group and then weaned. During the administering period, each group in 5 micextwo cages was bred in a see-through cage. As to water, tap water was made to freely drink and, as to a feed, a solid feed (CRF-1 manufactured by Oriental Yeast Industry) was made to freely ingest. Medium or the chimeric CNP (D, J) (structure mentioned already) was repeatedly administered once daily for 56 days subcutaneously from the back in a dose of 5 mL/kg, 50 nmol/kg or 200 nmol/kg, respectively and body length, tail length and body weight during the administered period were measured. The result is shown in FIG. 10 and the picture of full body length of the mice on the next day of the completion of the chimeric CNP J administration is shown in FIG. 11.

Figure 10:
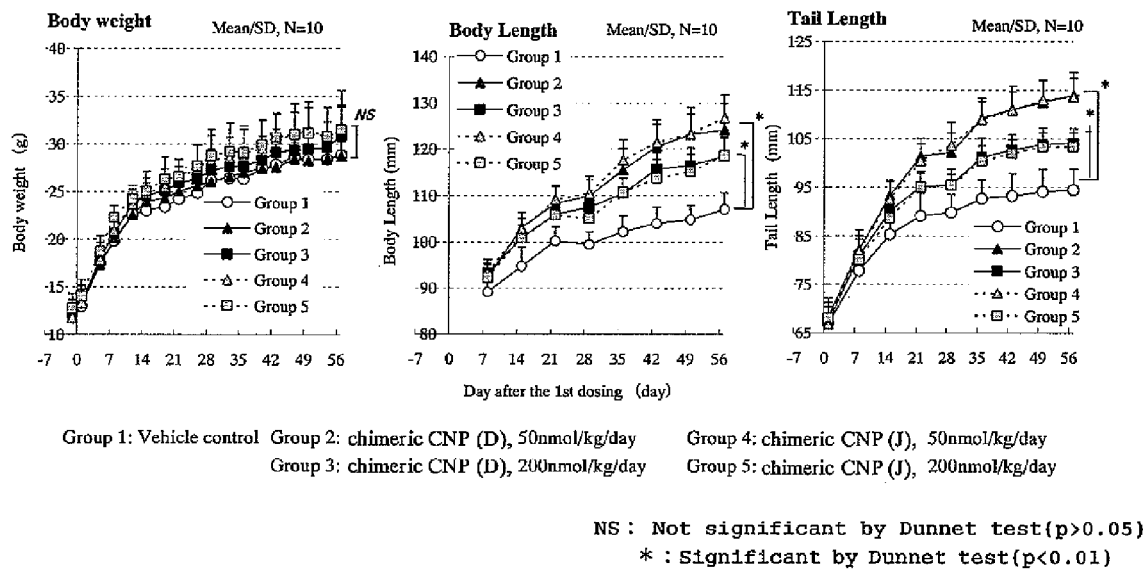
FIG. 10 This is a drawing which shows changes in body length, tail length and body weight when a chimeric CNP (D and J) (50 and 200 nmol/kg) is subcutaneously administered once daily for 56 days repeatedly to female mice.
Figure 11:
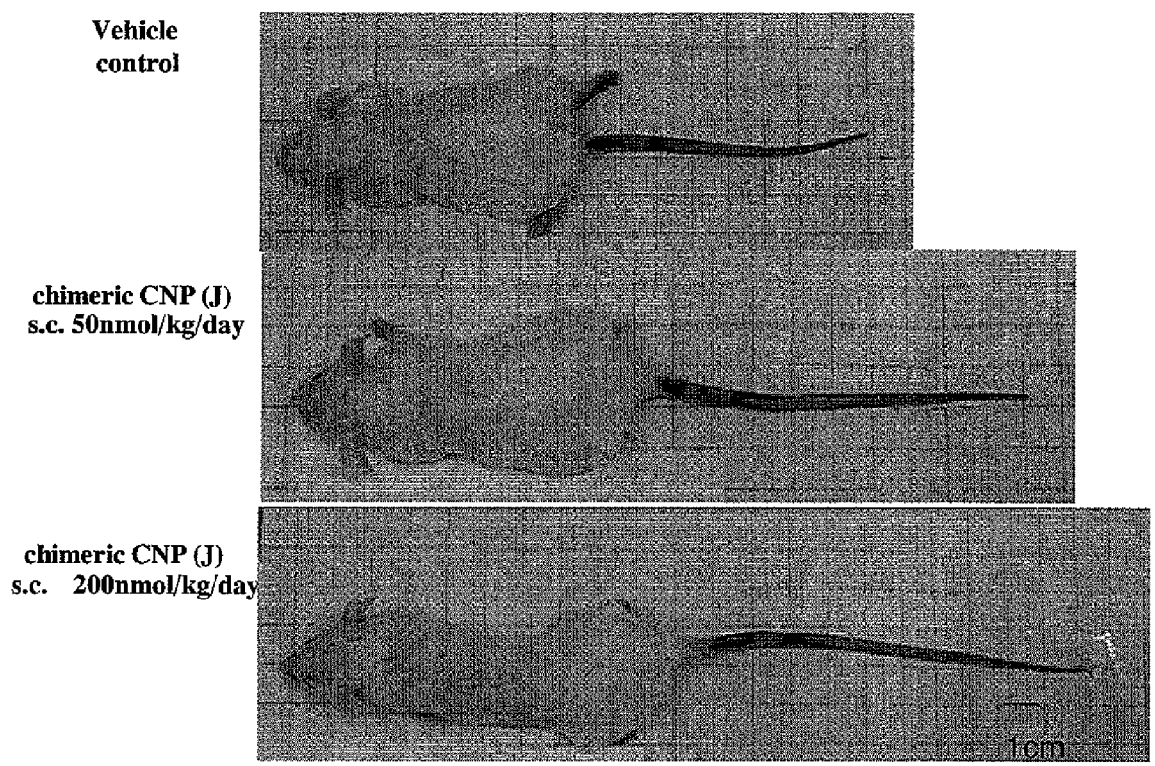
FIG. 11 This is a drawing which shows a total body image after a chimeric CNP (J) (50 and 200 nmol/kg) is subcutaneously administered once daily for 56 days repeatedly to female mice.

As shown in FIG. 10, when the chimeric CNPs (D, J) each where a half-life-extension peptide is bonded to native CNP-22 was repeatedly administered subcutaneously, body length and tail length of the mice significantly increased in a dose-dependent manner.

Example 11

Extension-promoting Action of Chimeric CNP (3)

Extension-promoting action of chimeric CNP was investigated using rats.

In the experiment, female SD (IGS) rats of three weeks age (Nippon Charles River) were used where one group comprised five rats and 20 rats in total were used for the experiment. The animals (17 days age) were purchased and ten baby rats with one mother rat were subjected to a preliminary breeding and then weaned. During the administering period, each group was bred in an aluminum hanging cage. As to water, tap water was made to freely drink and, as to a feed, a solid feed (CRF-1 manufactured by Oriental Yeast Industry) was made to freely ingest. Medium or the chimeric CNP (D) (structure mentioned already) was repeatedly administered once daily for 56 days subcutaneously from the back in a dose of 5 mL/kg, 50 nmol/kg or 200 nmol/kg, respectively and body length, tail length and body weight during the administered period were measured. The result is shown in FIG. 12.

Figure 12:
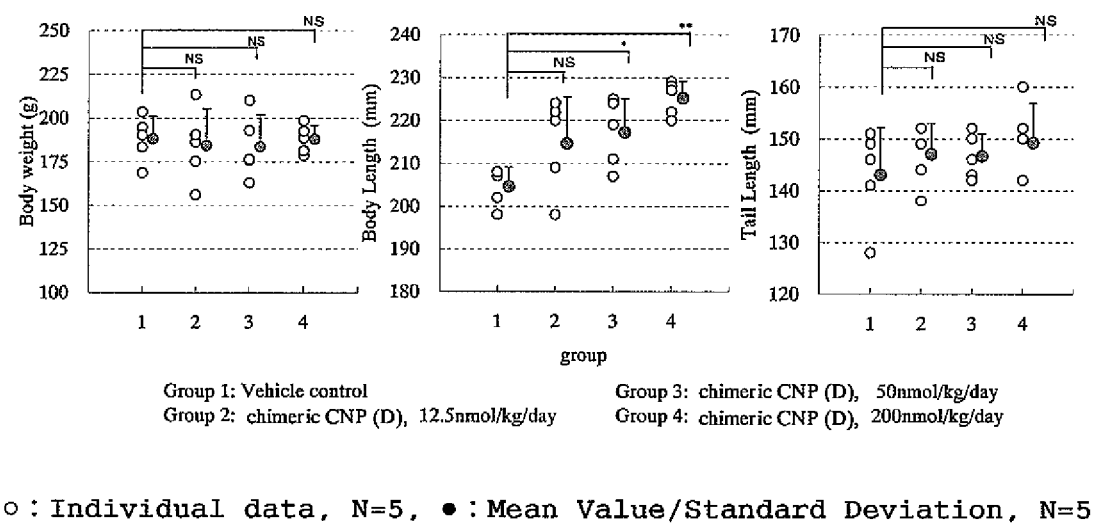
FIG. 12 This is a drawing which shows changes in body length, tail length and body weight when a chimeric CNP (D) (12.5, 50 and 200 nmol/kg) is subcutaneously administered once daily for 28 days repeatedly to female rats.

As shown in FIG. 12, body length of the rats to which a chimeric CNP (D) where a half-life-extension peptide was bonded to native CNP-22 was repeatedly administered subcutaneously in a dose of 12.5, 50 and 200 nmol/1 mL/kg significantly increased as compared with the group to which a medium was administered.

Example 12

Comparison of Half-life in Plasma of Native CNP-22 and Native CNP-53 and Chimeric CNP Changes in CNP immunoreactivity concentration in plasma when the native CNP-22 shown by SEQ ID No: 101 was administered either solely or jointly with neutral endopeptidase (NEP) inhibitor and compared with changes in CNP immunoreactivity concentration in plasma when native CNP-53 (SEQ ID No: 159) and the chimeric CNP (D) (structure mentioned already) were intravenously administered.

The experiment was conducted using rats where polyethylene tube (PE-50, manufactured by Clay Adams) was previously inserted into thigh artery under the anesthetized condition with Nembutal. In the group where the native CNP-22 was administered either solely or jointly with an NEP inhibitor, the polyethylene tube (PE-10, manufactured by Clay Adams) was also inserted into the thigh vein. As to a test system, male SD rats (Nippon Charles River) of 7 weeks age were used where one group comprised three rats. As to the NEP inhibitor, DL-Thiorphan (manufactured by Sigma) was used and, during the period from 10 minutes before the initiation of administration of the native CNP-22 until 60 minutes after the initiation of the administration where collection of the blood finished, 5% mannitol (100 μL/min/body) or NEP inhibitor (30 μg/100 μL/min/body) was subjected to a constant-speed intravenous administration for 70 minutes using an Infusion Pump (CFV 2100, manufactured by Nippon Koden K. K.). Native CNP-22, native CNP-53 or chimeric CNP (D) was administered into tail vein in a dose of 20 nmol/kg each and blood over the time from before administration and 60 minutes after administration was collected from a polyethylene tube inserted into the thigh artery. To the collected blood were added EDTA (Dojin Laboratories) and aprotinin (manufactured by Bayer) as a stabilizer and an anti-coagulant, respectively and the plasma was separated by means of centrifugal separation. CNP immunoreactivity concentration in the plasma was measured by a competitive radioimmunoassay (RIA). At that time, a rabbit polyclonal antibody (#2) which specifically recognizes a ring part structure which is the common structure for native CNP-22 and native CNP-53 was used as an antibody while, as a labeling compound, $^{125}$I-[Tyr$^0$] CNP-22 was used.

Figure 13:
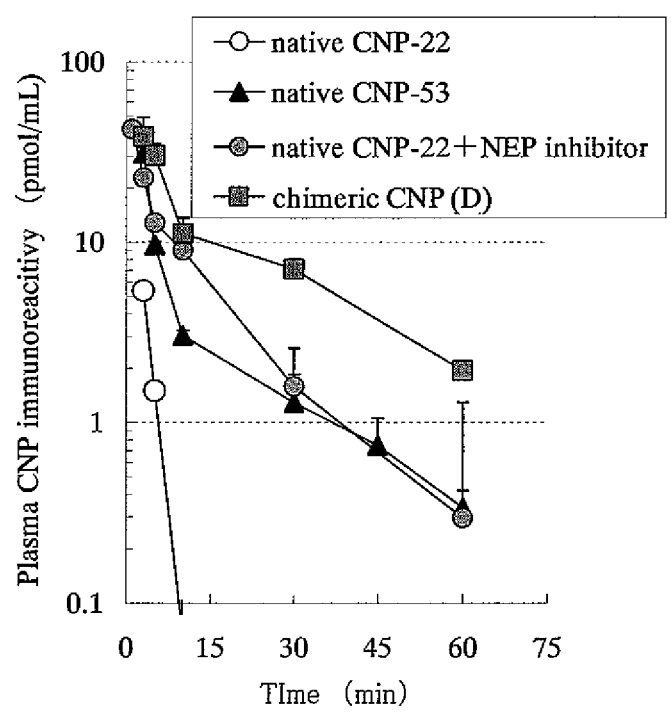
FIG. 13 This is a drawing which shows changes in a CNP immunoreactivity concentration in plasma when native CNP-22, native CNP-53 or a chimeric CNP (D) (10 nmol/kg) are intravenously administered to male rats.

Amino acid sequence, molecular weight and half-life for disappearance from the plasma for the native CNP-22, the native CNP-53 and the chimeric CNP (D) are shown in Table 18 and FIG. 13.

TABLE 18

List of amino acid sequence of native CNP-22, native CNP-53 and chimeric CNP (D) and half-life for disappearance from plasma when they were intravenously administered in a dose of 10 nmmol/kg (mean value ± standard devision, N = 3)

| Peptide | SEQ ID NO: | Amino Acid Sequence | Mol. Wt. | Joint Use with NEP Inhibitor | T½ (min) Mean Value | ± S.D. | P Value |
|---|---|---|---|---|---|---|---|
| Native CNP-22 | 101 | GLSKG*C*FGLKLDRIGSMSGLG*C* | 2198 | no | 1.11 | ±0.16 | — |
|  |  |  |  | yes | 16.25 | ±2.22* | 0.000 |
| Native CNP-53 | 169 | DLRVDTKSRAAWARLLQEHPNARKYKGANKKGL SKGGLSKG*C*FGLKLDRIGSMSGLG*C* | 5802 | no | 15.72 | ±1.49* | 0.000 |
| Chimeric CNP(D) | 125 | GLSKG*C*FGLKLDRIGSMSGLG*C*VQQRKESKKPP AKLQPR | 4198 | no | 20.30 | ±3.09* | 0.000 |

In all of them, S-S bond was formed at the underlined italic cysteine residues to form a cyclic structure.
*In t-test, a significant difference was available from the disappearance half-time of native CNP (without NEP inhibitor) (p < 0.05)

From Table 18 and FIG. 13, it was shown that the chimeric CNP (D) had longer half-life than any of the native CNP-22, the native CNP-22 together with NEP inhibitor and the native CNP-53. Since the native CNP-53 has a NEP resistance, its half-life is longer than the native CNP-22 and, since the pharmacokinetic pattern when the native CNP-22 was used together with the NEP inhibitor was nearly the same in both, it is likely that an amino acid sequence resulting in an NEP resistance is present in 1 to 21 positions of the native CNP-53. In addition, in the 1 to 21 positions of the native CNP-53, there is a sequence (RKYKGANKK) (SEQ ID NO: 170) similar to the formula B (corresponding to a core sequence) of the present invention.

Since the chimeric CNP (D) showed better pharmacokinetic pattern than the native CNP-53, it was shown that the alignment of acidic amino acid between the basic amino acid clusters represented by the formula B is necessary for exhibiting the characteristic of longer half-life.

Industrial Applicability

When the half-life-extension peptide according to the present invention is added to the object peptide having a short half-life, the pharmacokinetics in vivo is improved and the product has a practical half-life as a drug.

The invention claimed is:

1. An isolated chimeric peptide consisting of one or two added peptides and an object peptide wherein the added peptide is bonded to the N-terminus, the C-terminus or both of the object peptide, wherein if the added peptides are bound to both terminals, the two added peptides may be the same or different;
the added peptide is (I),
(I) a peptide represented by the formula B, A-B, B-C or A-B-C in which A, B and C each is represented by the following (1), (2) and (3);
(1) A is a peptide selected from the group consisting of a peptide consisting of an amino acid sequence of amino acid numbers 1 to 4 in SEQ ID No: 34, a peptide consisting of an amino acid sequence of amino acid numbers 1 to 8 in SEQ ID No.: 67, and a peptide consisting of an amino acid sequence where 1 to 6 amino acid(s) in the above amino acid sequence is/are deleted, substituted, and/or added;
(2) B is a peptide represented by the formula 1: (Wk-Xl-Y-Zm-Wn)-(Wo-Xp-Y-Zq-Wr)s,
wherein in the formula 1, W is a basic amino acid selected from Arg Lys; X and Z are the same or different and selected from the group consisting of Ser, Pro, Leu, Phe, Ala, Thr, Gly, Val, Tyr, and His; Y is Glu or Asp; k is 1 or 2; l is an integer of 4≥l≥0; m is an integer of 2≥m≥0; 4≥l+m≥0; n is 1 or 2; o is an integer of 2≥o≥0; p is an integer of 4≥p≥0; q is an integer of 2≥q≥0; 4≥p+q≥0; r is 1 or 2; and s is 0 or 1; and
(3) C is a peptide selected from the group consisting of a peptide consisting of amino acid numbers 10 to 17 in SEQ ID No: 34, a peptide consisting of amino acid numbers 14 to 17 in SEQ ID No: 67, a peptide consisting of an amino acid sequence where 1 to 6 amino acid(s)in the above amino acid sequence is/are deleted, and/or added, and/or 1 to 4 amino acid(s) in the above amino acid sequence is/are substituted, and the peptide contains 4 to 9 amino acid sequences being able to form a helix structure,
and physiological activity of the object peptide is still retained, wherein the object peptide is a natural physiologically active peptide selected from the group consisting of an atrial natriuretic peptide, a brain natriuretic peptide, a C type natriuretic peptide, motilin, glucagon like peptide 1, parathyroid hormone, and calcitonin, or a derivative thereof, wherein the derivative has one or more amino acid(s) deleted from the amino acid sequence of a natural physiologically active peptide and has the desired physiological activity.

2. The chimeric peptide according to claim 1, wherein the added peptide is bonded to the N-terminus of the object peptide.

3. The chimeric peptide according to claim 1, wherein the added peptide is bonded to the C-terminus of the object peptide.

4. The chimeric peptide according to claim 1, wherein the added peptide is bonded to both termini of the object peptide.

5. The chimeric peptide according of claim 1, wherein the object peptide is an atrial natriuretic peptide, a C type natriuretic peptide, or motilin, or derivatives thereof, wherein the derivative has one or more amino acid(s) deleted from the amino acid sequence of natural physiologically active peptide and has the desired physiological activity.

6. The chimeric peptide according to claim 1, wherein s is 1, o is 0, p is 0, q is 0, and r is 2 in the formula 1.

7. The chimeric peptide according to claim 1, wherein C has a Pro sequence between its terminal and the amino acid sequence being able to form a helix structure.

8. The chimeric peptide according to claim 1, wherein A is selected from the group consisting of SPEHQRVQQR, EHQRVQQR, QRVQQR, VQQR, VQQ, QR, and RPQLKAPP.

9. The chimeric peptide according to claim 1, wherein C is selected from the group consisting of PPAKLQPR, RQQV, PPAKLQ, PPAK, AKLQPR, AKLAALKA, PPAKLAALKA, PPAELAALEA, PPAELAALKA, and PPALQPR.

10. The chimeric peptide according to claim 1, wherein B is selected from the group consisting of KESKK, KKSEK, KEKK, KEFKK, KETKK, KEPKK, KELKK, KEAKK, KDSKK, KRDSRR, KGESKK, KESGKK, KGGESKK, KGGESGKK, KKAYSPDKERK, and KVVDHPKR.

11. The chimeric peptide according to claim 1, wherein the added peptide consists of amino acid sequence selected from the group consisting of amino numbers 23 to 39 of SEQ ID No: 106 (VQQRKESKKPPAKLQPR), amino acid numbers 1 to 17 in SEQ ID No: 108 (RPQLKAPPKKSEKRQQV), amino acid numbers 13 to 35 in SEQ ID No: 111 (SPEHQRVQQRKESKKPPAKLQPR), amino acid numbers 13 to 33 in SEQ ID No: 112 (EHQRVQQRKESKKPPAKLQPR), amino acid numbers 13 to 31 in SEQ ID No: 113 (QRVQQRKESKKPPAKLQPR), amino acid numbers 13 to 27 in SEQ ID No: 115 (QRKESKKPPAKLQPR), amino acid numbers 13 to 25 in SEQ ID No: 116 (KESKKPPAKLQPR), amino acid numbers 13 to 27 in SEQ ID No: 118 (VQQRKESIKKPPAKLQ), amino acid numbers 13 to 25 in SEQ ID No: 119 (VQQRKESKKPPAK), amino acid numbers 13 to 23 in SEQ ID No: 120 (VQQRKESKKPP), amino acid numbers 13 to 21 in SEQ ID No: 121 (VQQRKESKK), amino acid numbers 13 to 28 in SEQ ID No: 131 (VQQRKEKKPPAKLQPR), amino acid numbers 13 to 29 in SEQ ID No: 132 (VQQRKEFKKPPAKLQPR), amino acid numbers 13 to 29 in SEQ ID No: 133 (VQQRKETKKPPAKLQPR), amino acid numbers 13 to 29 in SEQ ID No: 134

(VQQRKEPKKPPAKLQPR), amino acid numbers 13 to 29 in SEQ ID No: 135 (VQQRKELKKPPAKLQPR), amino acid numbers 13 to 29 in SEQ ID No: 136 (VQQRKEAKKP-PAKLQPR), amino acid numbers 13 to 29 in SEQ ID No: 139 (VQQRKDSKIKPPAKLQPR), amino acid numbers 13 to 29 in SEQ ID No: 141 (VQQKRDSRRPPAKLQPR), amino acid numbers 13 to 29 in SEQ ID No: 142 (VQQKKSEKRP-PAKLQPR), amino acid numbers 13 to 30 in SEQ ID No: 143 (VQQRKGESKKPPAKLQPR), amino acid numbers 13 to 30 in SEQ ID No: 144 (VQQRKESGKKPPAKLQPR), amino acid numbers 13 to 31 in SEQ ID No: 145 (VQQRKG-GESKKPPAKLQPR), amino acid numbers 13 to 32 in SEQ ID No: 146 (VQQRKGGESGKKPPAKLQPR), amino acid numbers 13 to 27 in SEQ ID No: 147 (VQQRKESKKAK-LQPR), amino acid numbers 13 to 29 in SEQ ID No: 148 (VQQRKESKKAKLAALKA), amino acid numbers 13 to 31 in SEQ ID No: 149 (VQQRKESKKPPAKLAALKA), amino acid numbers 13 to 31 in SEQ ID No: 150 (VQQRKESKKP-PAELAALEA), amino acid numbers 13 to 31 in SEQ ID No: 151 (VQQRKESKKPPAELAALKA), amino acid numbers 13 to 27 in SEQ ID No: 154 (KESKKPPAKLAALKA), amino acid numbers 13 to 33 in SEQ ID No: 155 (VQQKKAYSPDKERKPPALQPR), amino acid numbers 13 to 34 in SEQ ID No: 156 (VQQKKAYSPDKERKPPAK-LQPR), and amino acid numbers 27 to 36 min SEQ ID No: 158 (QRKVVDHPKR).

12. An isolated chimeric peptide comprising an amino acid sequence shown in SEQ ID Nos: 106, 107, 108, 109, 110, 111, 112, 113, 114, 115, 116, 118, 119, 120, 121, 124, 125, 126, 127, 128, 129, 130, 131, 132, 133, 134, 135, 136, 139, 141, 142, 143, 144, 145, 146, 147, 148, 149, 150, 151, 154, 155, 156, or 157.

13. The isolated chimeric peptide consisting of an amino acid sequence shown in SEQ ID Nos: 106, 107, 108, 109, 110, 111, 1.12, 113, 114, 115, 116, 118, 119, 120, 121, 124, 125, 126, 127, 128, 129, 130, 131, 132, 133, 134, 135, 136, 139, 141, 142, 143, 144, 145, 146, 147, 148, 149, 150, 151, 154, 155, 156, 157, or 158.

14. The chimeric peptide according to claim 13, consisting of an amino acid sequence shown in SEQ ID NO: 125 or 157.

15. A pharmaceutical composition in which the chimeric peptide of claim 1 or a pharmaceutically acceptable salt thereof is an effective ingredient.

16. A pharmaceutical composition comprising a. chimeric peptide or a pharmaceutically acceptable salt thereof as an effective ingredient, wherein the chimeric peptide is the peptide of claim 5.

17. The pharmaceutical composition according to claim 16, wherein the object peptide in the chimeric peptide is an atrial natriuretic peptide or a derivative thereof, wherein the derivative has one or more amino acid(s) deleted from the amino acid sequence of national physiologically active peptide and has the desired physiological activity.

18. The pharmaceutical composition according to claim 17, wherein it is for the treatment of diseases selected from acute cardiac insufficiency, chronic cardiac insufficiency, obliterative arteriosclerosis, ischemic cardiac disease, hypertension, edema disease, myocardial disease, retinitis, diabetic renal disease, nephrosclerosis, and myocardial infarction.

19. The pharmaceutical composition according to claim 16, wherein the object peptide in the chimeric peptide is a C type natriuretic peptide or a derivative thereof, wherein the derivative has one or more amino acid(s) deleted from the amino acid sequence of national physiologically active peptide and has the desired physiological activity.

20. The pharmaceutical composition according to claim 19, wherein it is for the treatment of diseases selected from atypical chondrodysplasia, restenosis after PTCA after coronary artery stenosis, pulmonary hypertension, peripheral artery obliterative disease, osteoarthritis, rheumatoid arthritis, pulmonary fibrosis, hepatic fibrosis, renal fibrosis, myocardial infarction, and myocarditis.

21. The pharmaceutical composition according to claim 16, wherein the object peptide in the chimeric peptide is motilin or a derivative thereof, wherein the derivative has one or more amino acid(s) deleted from the amino acid sequence of a natural physiologically active peptide and has the desired physiological activity.

22. The pharmaceutical composition according to claim 21, wherein it is for the treatment of diseases selected from functional dyspepsia, reflux esophagitis, diabetic gastroparesis, constipation-type irritable bowel syndrome, chronic pseudoileus, postoperative ileus, chronic gastritis, and atrophic gastritis.

23. A process for producing a chimeric peptide consisting of one or two added peptides and an object peptide as defined in claim 1, characterized by a step of bonding the added peptide to the N-terminus, the C-terminus, or both of the object peptide, wherein if the added peptides are bound to both terminals, the added peptides may be the same or different;

wherein the added peptide is (I),
(I) a peptide represented by the formula B, A-B, B-C or A-B-C in which A, B and C each is represented by the following (1), (2) and (3);
(1) A is a peptide selected from the group consisting of a peptide consisting of an amino acid sequence of amino acid numbers 1 to 4 in SEQ ID No. 34, a peptide consisting of an amino acid sequence of amino acid numbers 1 to 8 in SEQ ID No.: 67, and a peptide consisting of an amino acid sequence where 1 to 6 amino acid(s) in the above amino acid sequence is/are deleted, substituted, and/or added;
(2) B is a peptide represented by the formula 1: (Wk-Xl-Y-Zm-Wn)-(Wo-Xp-Y-Zq-Wr)s,
wherein in the formula 1, W is a basic amino acid selected from Arg and Lys; X and Z are the same or different and selected from the group consisting of Ser, Pro, Leu, Phe, Ala, Thr, Gly, Val, Tyr, and His; Y is Glu or Asp; k is 1 or 2; l is an integer of $4 \geq l \geq 0$; m is an integer of $2 \geq m \geq 0$; $4 \geq l+m \geq 0$; n is 1 or 2; o is an integer of $2 \geq o \geq 0$; p is an integer of $4 \geq p \geq 0$; q is an integer of $2 \geq q \geq 0$; $4 \geq p+q \geq 0$; r is 1 or 2; and s is 0 or 1; and
(3) C is a peptide selected from the group consisting of a peptide consisting of amino acid numbers 10 to 17 in SEQ ID No: 34, a peptide consisting of amino acid numbers 14 to 17 in SEQ ID No: 67, a peptide consisting of an amino acid sequence where 1 to 6 amino acid(s)in the above amino acid sequence is/are deleted, and/or added, and/or 1 to 4 amino acid(s) in the above amino acid sequence is/are substituted, and the peptide contains 4 to 9 amino acid sequences being able to form a helix structure.

24. The process according to claim 23, wherein the added peptide is bonded to the N-terminus of the object peptide.

25. The process according to claim 23, wherein the added peptide is bonded to the C-terminus of the object peptide.

26. The process according to claim 23, wherein the added peptide is bonded to both termini of the object peptide.

27. The process according of claim 23, wherein the object peptide is a natriuretic peptide, motilin, or a derivative thereof, wherein the derivative has one or more amino acid(s deleted from the amino acid sequence of a natural physiologically active peptide and has the desired physiological activity.

28. The process according to claim 27, wherein the object peptide is an atrial natriuretic peptide or a derivative thereof, wherein the derivative has one or more amino acid(s) deleted from the acid sequence of a natural physiologically active peptide and has the desired physiological activity.

29. The process according to claim 27, wherein the object peptide is a C type natriuretic peptide or a derivative thereof, wherein the derivative has one or more amino acid(s) deleted from the amino acid sequence of a natural physiologically active peptide and has the desired physiological activity.

30. The process according to claim 27, wherein the object peptide is motilin or a derivative thereof, wherein the derivative has one or more amino acid(s) deleted from the amino acid sequence of a natural physiologically active peptide and has the desired physiological activity.

31. A method for the treatment of a disease that is able to be treated by the object peptide contained in a pharmaceutical composition according to claim 18, comprising administration of the pharmaceutical composition to an individual, wherein the disease is a disease selected from acute cardiac insufficiency, chronic cardiac insufficiency, obliterative arteriosclerosis, ischemic cardiac disease, hypertension, edema disease, myocardial disease, retinitis, diabetic renal disease, nephrosclerosis, and myocardial infarction.

32. A method for the treatment of a disease that is able to be treated by the object peptide contained in a pharmaceutical compostion, comprising administration of the pharmaceutical composition to an individual, wherein the pharmaceutical compostion is the composition of claim 19, and, wherein the disease is a disease selected from atypical chondrodysplasia, restenosis after PTCA after coronary artery stenosis, pulmonary hypertension, peripheral artery obliterative disease, osteoarthritis, rheumatoid arthritis, pulmonary fibrosis, hepatic fibrosis, renal fibrosis, myocardial infarction and myocarditis.

33. A method for the treatment of a disease that is able to be treated by the object peptide contained in a pharmaceutical composition, comprising administration of the pharmaceutical composition to an individual, wherein the pharmaceutical composition is the pharmaceutical composition of claim 21, and, wherein the disease is a disease selected from functional dyspepsia, reflux esophagitis, diabetic gastroparesis, constipation-type irritable bowel syndrome, chronic pseudoileus, postoperative ileus, chronic gastritis and atrophic gastritis.

\* \* \* \* \*

UNITED STATES PATENT AND TRADEMARK OFFICE
CERTIFICATE OF CORRECTION

PATENT NO.         : 8,551,937 B2
APPLICATION NO.    : 12/675961
DATED              : October 8, 2013
INVENTOR(S)        : Wakabayashi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 240 days.

Signed and Sealed this

Fifteenth Day of September, 2015

Michelle K. Lee
*Director of the United States Patent and Trademark Office*